(12) United States Patent
Thayumanavan

(10) Patent No.: US 9,795,689 B2
(45) Date of Patent: Oct. 24, 2017

(54) CROSSLINKED POLYMER NANO-ASSEMBLIES AND USES THEREOF

(71) Applicant: University of Massachusetts, Boston, MA (US)

(72) Inventor: Sankaran Thayumanavan, Amherst, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/421,882

(22) PCT Filed: Sep. 10, 2013

(86) PCT No.: PCT/US2013/059010
§ 371 (c)(1),
(2) Date: Feb. 16, 2015

(87) PCT Pub. No.: WO2014/043110
PCT Pub. Date: Mar. 20, 2014

(65) Prior Publication Data
US 2015/0209447 A1    Jul. 30, 2015

Related U.S. Application Data

(60) Provisional application No. 61/699,770, filed on Sep. 11, 2012.

(51) Int. Cl.
| | | |
|---|---|---|
| *A61K 47/48* | (2006.01) |
| *A61K 9/06* | (2006.01) |
| *A61K 47/42* | (2017.01) |
| *C08F 220/28* | (2006.01) |
| *A61K 31/485* | (2006.01) |
| *C08F 20/68* | (2006.01) |
| *C08L 33/14* | (2006.01) |
| *C08F 120/24* | (2006.01) |

(52) U.S. Cl.
CPC .......... *A61K 47/48961* (2013.01); *A61K 9/06* (2013.01); *A61K 31/485* (2013.01); *A61K 47/42* (2013.01); *C08F 20/68* (2013.01); *C08F 220/28* (2013.01); *C08L 33/14* (2013.01); *C08F 120/24* (2013.01); *C08F 2438/03* (2013.01)

(58) Field of Classification Search
USPC ...................................... 514/772.1, 44, 772.3
See application file for complete search history.

(56) References Cited

U.S. PATENT DOCUMENTS

2007/0059373 A1*  3/2007  Oberg ................. A61K 9/1617
                                                          424/489
2008/0299177 A1* 12/2008  Hardy ................. A61K 9/0009
                                                          424/427

OTHER PUBLICATIONS

Wu; Journal of Pharmacy and pharmaceutical sciences; 11(4), 2008, 32-45.*
Ryu (Journal of the American Chemical Society; 2010, 132, 17227-17235).*
Sawyer (The Journal of Biological Chemistry; 1973, 248, 24, 8429-8433).*

* cited by examiner

*Primary Examiner* — Pancham Bakshi
(74) *Attorney, Agent, or Firm* — Milstein Zhang & Wu LLC

(57) ABSTRACT

The invention provides powerful methods and compositions for designing, selecting, fine-tuning and optimizing polymer nanogel and other supramolecular assemblies for various properties including, for example, particle size, density and morphology, guest loading capacity and encapsulation stability, and dynamic release control.

19 Claims, 37 Drawing Sheets

| | Monomer | Polymer |
|---|---|---|
|  | 8.4 | 7.4 |
|  | 9.2 | 7.4 |
|  | 8.5 | 6.3 |
|  | 6.9 | 5.1 |
|  | 9.1 | 7.6 |
|  | 8.9 | 6.9 |
|  | 8.6 | 6.7 |

…

CROSSLINKED POLYMER NANO-ASSEMBLIES AND USES THEREOF

PRIORITY CLAIMS AND RELATED PATENT APPLICATIONS

This application is the U.S. national phase of and claims the benefit of priority from PCT/US13/59010, filed Sep. 10, 2013, which claims the benefit of priority from U.S. Provisional Application Ser. No. 61/699,770, filed on Sep. 11, 2012, the entire content of each of which is incorporated herein by reference in its entirety.

GOVERNMENT RIGHTS

The United States Government has certain rights to the invention pursuant to Grant No. W911NF1010313 from U.S. Army Research Office, Grant No. GM-065255 from the National Institutes of Health, Grant No. DMR-0820506 from the National Science Foundation (MRSEC) to the University of Massachusetts.

TECHNICAL FIELDS OF THE INVENTION

The invention generally relates to polymer nano-structures and drug delivery. In particular, the invention particularly relates to novel, functionalized polymer nano-assemblies that are useful as drug delivery vehicles and related methods for making the nano-assemblies and for controlled and targeted delivery of therapeutic, diagnostic or imaging agents. More particularly, the invention relates to compositions and methods for modifying various properties of the polymer nano-assemblies to achieve desired characteristics.

BACKGROUND OF THE INVENTION

Although tremendous progress has been made in the field of drug delivery, major challenges remain in controlled administration of insoluble and toxic hydrophobic drugs to target sites. A goal that continues to elude researchers is a functional system wherein a water-soluble container non-covalently binds hydrophobic guest molecules and releases them in a controlled manner in response to a specific trigger. Issues of encapsulation stability and versatility of the delivery vehicles continue to present major difficulties. When such a container is based on a nano-sized host, there is an even greater interest because of the potential in passive targeting of tumor tissue through the so-called enhanced permeability and retention (EPR) effect. (Peer, et al. 2007 Nat. Nanotechnol. 2, 751-760; Haag 2004 Angew. Chem. Int. Ed. 43, 278-282; Ganta, et al. 2008 J. Control. Release 126, 187-204; Allen, et al. 2004 Science 303, 1818-1822; Maeda, et al. 2000 J. Control. Release 65, 271-284.)

Water-soluble cross-linked polymer nanoparticles or nanogels that can sequester hydrophobic guest molecules within their interiors is of great interest in various applications ranging from delivery vehicles for therapeutics, to diagnostics to theranostics, among others. However, the classical preparative methods including microemulsion or inverse microemulsion ones do not conveniently allow the nanogels to be water-soluble and encapsulate hydrophobic guest molecules simultaneously. (Bachelder, et al. 2008 J. Am. Chem. Soc. 130, 10494; Oh, et al. 2007 J. Am. Chem. Soc. 129, 5939.)

Micellar assemblies are capable of non-covalently sequestering hydrophobic guest molecules in aqueous solution and solubilizing water-insoluble drug compounds within hydrophobic cores. These polymer micelles offer advantages in their nanoscopic sizes, which allow for passive targeting of certain disease sites through the enhanced permeability and retention effect. (Matsumura, et al. 1986 Cancer Res. 46, 6387-6392; Baban, et al. 1998 Adv. Drug Delivery Rev. 34, 109-119; Maeda, et al. 2000 J. Controlled Release, 65, 271-284; Duncan 2003 Nat. Rev. Drug Discovery, 2, 347-360.)

Micellar assemblies formed from small molecule surfactants, however, have inherent stability issues. Assemblies formed from amphiphilic polymers tend to exhibit enhanced stabilities, although they face significant complications because of a requisite concentration for assembly formation, which drastically limits the practicality of in vivo micelle utilization. Large dilution of injected micelles into the body can destabilize the self-assembling systems and cause uncontrolled and undesirable release of the encapsulated drug payload before arrival at the target site. Therefore, alternate strategies are desired to overcome such premature release. Moreover, the interaction between micelles and biological components, such as cellular membranes and blood components, can lead to premature release of the payload from the micelle core. (Bae, et al. 2008 J. Control. Release 131, 2-4; Chen, et al. 2008 Proc. Natl. Acad. Sci. U.S.A. 105, 6596-6601; Chen, et al. 2008 Langmuir 24, 5213-5217.)

Cross-linked polymer nanogels potentially provide both high encapsulation stability and potential for triggered release. Current synthetic methods for nanogel preparation are based on water-in-oil emulsion, in which inverse micelles, formed from surfactants in non-polar solvent, provide an aqueous interior as a reaction template for polymerization. These methods are complex and require multiple purification steps to remove unreacted monomers and surfactant materials that were used to stabilize the emulsion. (Bachelder, et al. 2008 J. Am. Chem. Soc. 130, 10494-10495; Sission, et al. 2009 Angew. Chem. Int. Ed. 48, 7540-7545; Kriwet, et al. 1998 J. Controlled Release 56, 149-158; Oh, et al. 2008 Prog. Polym. Sci. 33, 448-477.)

When a water-soluble polymer nanoparticle is targeted, inverse microemulsion-based synthesis is a preferred method. The continuous phase in the inverse microemulsion (water-in-oil emulsion) method is based on a hydrophobic solvent and, therefore, cannot be used to encapsulate hydrophobic guest molecules during nanoparticle formation.

A new emulsion-free method was recently developed for synthesis of cross-linked nanogels in aqueous media that allows facile hydrophobic guest encapsulation. This one pot synthesis is faster and easier than previous methods to achieve uniformly sized nanogels. (Ryu, et al. 2010 J. Am. Chem. Soc. 132, 8246-8247; Jiwpanich, et al. 2010 J. Am. Chem. Soc. 132, 10683-10685; Ryu, et al. 2010 J. Am. Chem. Soc. 132, 1722 7-17235.)

Improved polymer nano-assemblies and methods that allow systematic evaluation and fine-tuning of a broad range of properties and functionalities of nano-delivery vehicles are required to overcome the limitations and shortcomings of the existing technologies.

SUMMARY OF THE INVENTION

The invention provides nano-scale assemblies such as polymer nanogels as drug delivery vehicles that encapsulate therapeutic or diagnostic agents as payloads and release them in response to a pre-selected and specific trigger in situ. More particularly, the invention provides compositions and methods for modifying and transforming a diverse set of properties of the polymer nano-assemblies to achieve desired characteristics and functionalities.

Methods disclosed herein are powerful tools for designing, selecting, fine-tuning and optimizing polymer nanogels and other supramolecular assemblies to achieve various desirabilities including in, for example, particle size, density and morphology, guest loading capacity, encapsulation stability and dynamic release control.

In one aspect, the invention generally relates to a method for varying a property of polymer nanogel. The method includes preparing a polymer nanogel in an aqueous environment that has one or more kosmotropic or chaotropic agents, wherein the one or more kosmotropic or chaotropic agents are present at a concentration suitable for achieving the desired property. The properties of polymer nanogel that may be modified may be any relevant property to a particular application including, for example, the particle size, morphology and encapsulation stability of the polymer nanogel.

In another aspect, the invention generally relates to a method for modifying the release rate of encapsulated guests in a polymer nanogel host. The method includes preparing a polymer nanogel host in an aqueous environment having a kosmotropic or chaotropic agent, wherein the kosmotropic or chaotropic agent is present at a concentration suitable for achieving the desired guest release rate.

In yet another aspect, the invention generally relates to a method for affecting a characteristic of guest encapsulation in a polymer nanogel host particle. The method includes varying the hydrophobicity of the crosslinked polymer. The characteristic may be any characteristic associated with the polymer nanogel including, for example, guest loading capacity, guest encapsulation stability, host particle size and host particle morphology. In certain preferred embodiments, varying the hydrophobicity of a crosslinked polymer is by varying the hydrophobicity of a monomer of the polymer.

In yet another aspect, the invention generally relates to a charge-neutral nanogel capable of transforming to a positively charged nanogel at acidic pH. The charge-neutral nanogel includes: a crosslinked copolymer and a non-covalently encapsulated guest stably encapsulated, wherein the nanogel attains a positive charge at a pH characteristic of acidic tumor extracellular environment and is effectively taken up without leakage of guest molecules.

In yet another aspect, the invention generally relates to a nano-assembly for delivering a non-covalently encapsulated guest. The nano-assembly includes: a nanogel-polyelectrolyte complex of a positively charged nanogel with the guest non-covalently encapsulated therein; and a negatively charged polyelectrolyte. The polyelectrolyte undergoes a charge conversion at a pre-selected acidic pH stimulus, triggering dissociation of nanogel-polyelectrolyte complex without causing release of the non-covalently encapsulated guest. Upon contacting a pre-selected redox stimulus the nanogel is partially or completely de-crosslinked causing release of the encapsulated guest therefrom.

In yet another aspect, the invention generally relates to a crosslinked polymer network of a block or random co-polymer having the structural formula:

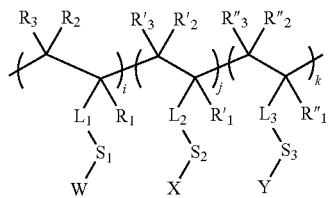

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;
W is a hydrophilic group;
X is a group comprising a crosslinking moiety;
Y is a hydrophobic group; and
each of i, j and k is independently a positive number.

In certain embodiments, each of $R_2$, $R'_2$, $R''_2$, $R_3$, $R'_3$ and $R''_3$ is a hydrogen, and each of $R_1$, $R'_1$ and $R''_1$ is a methyl group. In certain embodiments, each of $L_1$, $L_2$ and $L_3$ is

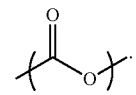

In certain embodiments, W comprises

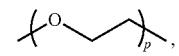

wherein p is an integer from about 1 to about 40.

In yet another aspect, the invention generally relates to a delivery vehicle for controlled delivery of a drug. The delivery vehicle includes: a water-soluble polymer host comprising a crosslinked network of polymer; and a guest comprising a drug non-covalently associated with the polymer host, wherein the drug is releasable upon partial or complete de-crosslinking of the crosslinked network of polymer molecules at or near the biological site in response to an in situ stimuli indicative of a biological need for the drug.

DEFINITIONS

Figure 1:
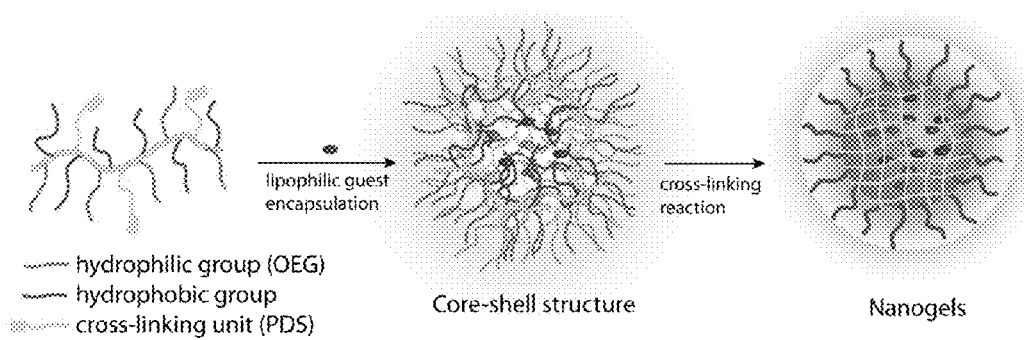
FIG. 1. Schematic illustration of guest loaded nanogel formation from random copolymer precursors modified with alkyl chain derived monomers.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999. It will be appreciated that the compounds, as described herein, may be substituted with any number of substituents or functional moieties.

As used herein, "$C_x$-$C_y$," refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{20}$" and the likes similarly encompass the various combinations between 1 and 20 (inclusive) carbon atoms, such as $C_1$-$C_6$, $C_1$-$C_{12}$ and $C_3$-$C_{12}$.

As used herein, the term "$C_x$-$C_y$ alkyl" refers to a saturated linear or branched free radical consisting essentially of x to y carbon atoms, wherein x is an integer from 1 to about 10 and y is an integer from about 2 to about 20. Exemplary $C_x$-$C_y$ alkyl groups include "$C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc.

As used herein, the term, "$C_x$-$C_y$ alkoxy" refers to a straight or branched chain alkyl group consisting essentially of from x to y carbon atoms that is attached to the main structure via an oxygen atom, wherein x is an integer from 1 to about 10 and y is an integer from about 2 to about 20. For example, "$C_1$-$C_{20}$ alkoxy" refers to a straight or branched chain alkyl group having 1-20 carbon atoms that is attached to the main structure via an oxygen atom, thus having the general formula alkyl-O—, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

As used herein, the term "halogen" refers to fluorine, chlorine, bromine, or iodine.

DETAILED DESCRIPTION OF THE INVENTION

The invention provides powerful methods and compositions for designing, selecting, fine-tuning and optimizing polymer nanogel and other supramolecular assemblies for various properties including, for example, particle size, density and morphology, guest loading capacity and encapsulation stability, and dynamic release control.

As previously disclosed in PCT International Application No. PCT/US2012/038972 (titled "CROSSLINKED POLYMER NANO-ASSEMBLIES AND USES THEREOF", filed May 22, 2012, the entire content of which is expressly incorporated herein by reference for all purposes), delivery systems of the invention are of great interest in therapeutic applications, especially for cancer, arthritis and related diseases with inflamed organs, tissues, or cells.

Micellar systems, due to their capacity to bind hydrophobic guest molecules non-covalently, are promising delivery vehicles to overcome the bottlenecks of traditional chemotherapies. However, the drug encapsulation stability of selfassembled systems during blood circulation continues to be a major obstacle. Thus, deliberate molecular design and selection is required for stable encapsulation, targeting and triggered release.

The primary basis for encapsulation of hydrophobic guest molecules within an amphiphilic assembly is miscibility with the hydrophobic interior. Increasing the hydrophobicity of the assembly interior provides a greater thermodynamic driving force for hydrophobic encapsulation. This driving force defines the distribution coefficient of hydrophobic guest molecules between the assembly interior and the bulk aqueous phase, which in turn dictates the loading capacity of the nanoassembly. (Lavasanifar, et al. 2002 *Adv. Drug Delivery Rev.* 54, 169-190; Savić, et al. 2006 *J. Drug. Target.* 14, 343-355; Letchford, et al. 2008 *J. Pharm. Sci.* 97, 1179-1190; Kim, et al. 2010 *Expert Opin. Drug Deliv.* 7, 49-62.)

Complementing loading capacity, encapsulation stability is an additional critical factor for a nanoassembly to serve effectively as a delivery scaffold for biological applications. Encapsulation stability can be defined as a measure of the dynamic exchange of guest molecules between the assembly interior and the bulk solvent, and is thus an indicator of potential guest molecule leakage. (Bae, et al. 2008 *J. Controlled Release* 131, 2-4; Chen, et al. 2008 *Langmuir* 24, 5213-5217.)

Inorganic salts have the ability to enhance the solubilization or precipitation of proteins in an aqueous solution, based on a phenomenon observed by Hofmeister the late 19th century. It has been shown that that addition of salts can significantly alter the lower critical solution temperature (LCST) of water-soluble polymers and that the effect is dependent on the nature of the salt, i.e. they follow the Hofmeister series. The LCST behavior, or the macroscopic phase separation of the polymer from the aqueous phase, is attributed to the reduced hydrogen bonding driven interaction between water and the polymer at elevated temperatures. (Hofmeister 1888 *Arch. Exp. Pathol. Pharmocol.* 24, 247; Hippel, et al. 1964 *Science* 145, 577; Baldwin 1996 *Biophys. J.* 71, 2056; Zhang, et al. 2005 *J. Am. Chem. Soc.* 127, 14505; Magnusson, et al. 2008 *J. Am. Chem. Soc.* 130, 10852.)

Another important feature desirable in the next generation targeted and responsive delivery is the utilization of dual or multiple stimuli to maximize selectivity and specificity of delivery. Toward this goal, single and dual responsive polymeric nanogel systems are disclosed here that incorporate novel cross-linking functionalities. One such system involves a pH/$CO_2$ responsive nanogel degradation and concurrent guest release. A second system utilizes an overexpressed enzyme in the tumor extracellular matrix, MMP9, with the purpose of facilitating tumor specific drug release. Third, a pH responsive charge conversional nanogel is developed that increases cellular uptake at the tumor specific pH but remains in circulation under normal physiological pH.

While multi-stimuli systems provide selectivity, introduction of a diverse single stimulus (e.g., other than the glutathione-sensitive system), broadens the scope of the nanogel technology. For example, in applications where intracellular delivery is not the target, it is essential that a stimulus other than the glutathione-sensitive system is used, such as pH, $CO_2$ and enzyme-based (e.g., matrix metalloproteinases-based) stimuli systems developed here.

Morphine antidote serves as an interesting example of an application for drug delivery systems of the invention. Morphine is an extremely potent opiate analgesic drug, which relieves pain when used in appropriate amounts. However, an overdose of morphine can lead to hypoventilation, resulting in an increase in blood $CO_2$ levels and a decrease in blood pH. This pH depression can lead to serious health complications, including death. In order to avoid this potentially fatal situation, a $CO_2$/pH-responsive nanogel, loaded with a morphine antidote can be developed. It may be administered concurrently with morphine. The nanogel stably encapsulates the antidote (e.g., naloxone) under normal physiological pH of 7.4. If the pH of the blood were to decrease below a certain threshold, the gel would degrade and release its payload. The antidote would block further morphine activity and prevent or stop hypoventilation before it became fatal.

Stimuli responsive guest release and cellular uptake via charge conversion can be systematically controlled by the incorporation of pH, $CO_2$, and enzyme responsive functional groups in the nanogels.

In one aspect, the invention generally relates to a method for varying a property of polymer nanogel. The method includes preparing a polymer nanogel in an aqueous environment that has one or more kosmotropic or chaotropic agents, wherein the one or more kosmotropic or chaotropic agents are present at a concentration suitable for achieving the desired property. The properties of polymer nanogel that may be modified may be any relevant property to a particular application including, for example, the particle size, morphology and stability of the polymer nanogel.

In another aspect, the invention generally relates to a method for modifying the release rate of encapsulated guest in a polymer nanogel host. The method includes preparing a polymer nanogel host in an aqueous environment having a kosmotropic or chaotropic agent, wherein the kosmotropic or chaotropic agent is present at a concentration suitable for achieving the desired guest release rate.

In certain preferred embodiments, preparation of a polymer nanogel is conducted in an aqueous environment having one or more kosmotropic agents at a concentration suitable for desired property.

In certain preferred embodiments, preparation of a polymer nanogel is conducted in an aqueous environment having one or more chaotropic agents at a concentration suitable for desired property.

The one or more kosmotropic agents may be any suitable kosmotropuc agents including, for example, sulfates ($SO_4^{2-}$), phosphates ($PO_4^{3-}$), hydrogenphosphates ($HPO_4^{2-}$), hydroxides ($OH^-$), magnesium ($Mg^{2+}$) calcium ($Ca^{2+}$) sodium ($Na^+$), lithium ($Li^+$), proton ($H^+$), trialkylamine oxide ($R_3N^+O^-$), proline, ectoine, glycine betaine, and trehalose. The one or more kosmotropic agents are present at a concentration from about 1 mM to about 5 M. In certain preferred embodiments, the kosmotropic agent is a sulfate ($SO_4^{2-}$).

The one or more chaotropic agents may be any suitable chaotropic agents including, for example, thiocyanates ($SCN^-$), dihydrogenphosphates ($H_2PO_4^-$), bisulfates ($HSO_4^-$), bicarbonates ($HCO_3^-$), iodides ($I^-$), bromides ($Br^-$), chlorides ($Cl^-$), nitrates ($NO_3^-$), ammonium ($NH_4^+$), cesium ($Cs^+$), potassium ($K^+$), guanidinium (($NH_2)_3C^+$), tetraalkylammonium ($R_4N^+$), and urea. The one or more chaotropic agents are present at a concentration from about 1 mM to about 5M. In certain preferred embodiments, the chaotropic agent is a thiocyanate ($SCN^-$).

In certain preferred embodiments, the polymer nanogel is a nano-assembly that includes a water-soluble polymer host comprising a crosslinked network of polymer; and a guest molecule non-covalently associated with the polymer host, wherein the guest is releasable upon partial or complete de-crosslinking of the crosslinked network of polymer molecules. In certain embodiments, the polymer is a random co-polymer. In certain embodiments, the polymer is a bock co-polymer.

In certain preferred embodiments, the nano-assembly is capable of crossing cellular membrane. In certain preferred embodiments, the nano-assembly further includes a guiding (e.g., targeting) moiety that is capable of bringing or transporting the nano-assembly to the vicinity of or inside the biological site, wherein the guiding moiety is covalently bound to the polymer host network. In certain preferred embodiments, the guiding moiety is an antibody or an antibody fragment.

The random co-polymer may include one or more hydrophilic co-monomers, for example, functionalized with a hydrophilic side chain such as a side chain having an oligoethylene glycol moiety.

The guest may be any suitable payload, for example, a therapeutic, diagnostic, or imaging agent encapsulated in the crosslinked polymer host.

In yet another aspect, the invention generally relates to a method for affecting a characteristic of guest encapsulation in a polymer nanogel host particle. The method includes varying the hydrophobicity of the crosslinked polymer. The characteristic may be any characteristic associated with the polymer nanogel including, for example, guest loading capacity, guest encapsulation stability, host particle size and host particle morphology.

In certain preferred embodiments, varying the hydrophobicity of a crosslinked polymer is by varying the hydrophobicity of a monomer of the polymer. In certain embodiments, varying the hydrophobicity of a crosslinked random co-polymer is by varying the hydrophobicity of a co-monomer of the co-polymer, for example, by including a co-monomer having a hydrophobic side chain and/or a co-monomer having a hydrophilic side chain. The hydrophobic side chain may be a hydrocarbon chain such as a $C_1$-$C_{40}$ alkyl chain (linear or branched).

In yet another aspect, the invention generally relates to a charge-neutral nanogel capable of transforming to a positively charged nanogel at acidic pH. The charge-neutral nanogel includes: a crosslinked copolymer and a non-covalently encapsulated guest stably encapsulated, wherein the nanogel attains a positive charge at a pH characteristic of acidic tumor extracellular environment and is effectively taken up without leakage of guest molecules.

Figure 63:
FIG. 63. pKa of exemplary monomers having amino groups and corresponding polymers.
Figure 63:
Figure 63:
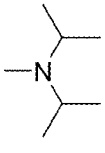
Figure 63:
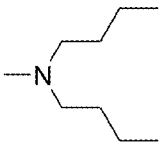
Figure 63:
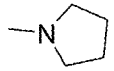
Figure 63:
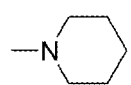
Figure 63:
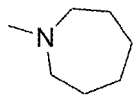

In certain preferred embodiments, the copolymer is a copolymer of a tertiary-amino methacrylate (e.g., a (trialkylamino)alkyl methacrylate) and an oligoethylene glycol. FIG. 63 lists various tertiaryamino moieties that may be used to fine tune the pKa and the pH for a nanogel to attain a positive charge.

In certain preferred embodiments, the copolymer is a copolymer of 2-(diisopropylamino)ethyl methacrylate and oligoethylene glycol.

In certain preferred embodiments, the nanogel transforms from a neutral nanogel to a positively charged nanogel at acidic pH from about 6.0 to about 7.5.

In yet another aspect, the invention generally relates to a nano-assembly for delivering a non-covalently encapsulated guest. The nano-assembly includes: a nanogel-polyelectrolyte complex of a positively charged nanogel with the guest non-covalently encapsulated therein; and a negatively charged polyelectrolyte. The polyelectrolyte undergoes a charge conversion at a pre-selected acidic pH stimulus, triggering dissociation of nanogel-polyelectrolyte complex without causing release of the non-covalently encapsulated guest. Upon contacting a pre-selected redox stimulus the nanogel is partially or completely de-crosslinked causing release of the encapsulated guest therefrom.

In yet another aspect, the invention generally relates to a crosslinked polymer network of a block or random co-polymer having the structural formula:

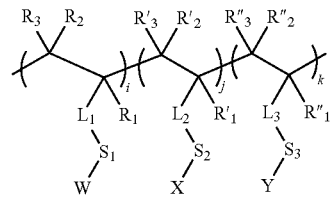

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;
W is a hydrophilic group;
X is a group comprising a crosslinking moiety;
Y is a hydrophobic group; and
each of i, j and k is independently a positive number.

In certain embodiments, each of $R_2$, $R'_2$, $R''_2$, $R_3$, $R'_3$ and $R''_3$ is a hydrogen, and each of $R_1$, $R'_1$ and $R''_1$ is a methyl group. In certain embodiments, each of $L_1$, $L_2$ and $L_3$ is

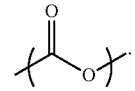

In certain embodiments, W comprises

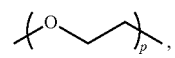

wherein p is an integer from about 1 to about 40 (e.g., from about 1 to about 36, from about 1 to about 24, from about 1 to about 12, from about 1 to about 6, from about 3 to about 36, from about 3 to about 24, from about 3 to about 12, from about 6 to about 36, from about 6 to about 24, from about 6 to about 12). W may include a charged group, a zwitterionic group.

Y may include any hydrophobic moiety including a hydrocarbon chain, such as a $C_1$-$C_{40}$ alkyl chain (e.g., linear or branched a $C_1$-$C_{36}$ alkyl chain, a $C_1$-$C_{24}$ alkyl chain, a $C_1$-$C_{12}$ alkyl chain, a $C_1$-$C_6$ alkyl chain, a $C_3$-$C_{36}$ alkyl chain, a $C_3$-$C_{24}$ alkyl chain, a $C_3$-$C_{12}$ alkyl chain a $C_6$-$C_{36}$ alkyl chain, a $C_6$-$C_{24}$ alkyl chain, a $C_6$-$C_{12}$ alkyl chain).

In certain preferred embodiments, X comprises a disulfide moiety.

In yet another aspect, the invention generally relates to a delivery vehicle for controlled delivery of a drug. The delivery vehicle includes: a water-soluble polymer host comprising a crosslinked network of polymer; and a guest comprising an antidote agent non-covalently associated with the polymer host, wherein the drug is releasable upon partial or complete de-crosslinking of the crosslinked network of polymer molecules at or near the biological site in response to an in situ stimuli indicative of a biological need for the drug.

In certain preferred embodiments, the delivery vehicle is a nanoscale particulate assembly of the crosslinked network of polymer with the guest having the drug encapsulated therein. In certain preferred embodiments, the delivery vehicle is prepared by an emulsion-free process.

In certain preferred embodiments, the in situ stimuli include a blood pH level below the normal physiological pH and/or a blood $CO_2$ level.

Syntheses of the nano-assemblies of the invention can be readily achieved in aqueous phase from a water-soluble precursor polymer. Incorporation of surface functionalities and non-covalent encapsulation of hydrophobic guest molecules can be achieved under mild conditions. In some embodiments, the co-polymer has a molecular weight from about 1,000 to about 100,000 (e.g., from about 2,000 to about 100,000, from about 5,000 to about 100,000, from about 10,000 to about 100,000, from about 20,000 to about 100,000, from about 50,000 to about 100,000, from about 1,000 to about 10,000, from about 1,000 to about 10,000, from about 1,000 to about 20,000, from about 1,000 to about 50,000).

In some embodiments, the ratio of i:j:k may be any ratios suitable to a particular application, for example, in the range for j:k from about 1:19 to about 19:1 and the relative ratio of 'i' to the sum of 'j' and 'k' to range from about 10:1 to 1:10.

Each of i, j and k may constitute a pre-selected % of the total monomers, e.g., from about 1% to about 95%, for example, from about 2% to about 95%, from about 5% to about 95%, from about 10% to about 95%, from about 20% to about 95%, from about 30% to about 95%, from about 40% to about 95%, from about 1% to about 90%, from about 1% to about 85%, from about 1% to about 80%, from about 1% to about 75%, from about 1% to about 70%, from about 1% to about 60%.

The crosslinked network of polymer molecules may be crosslinked inter-molecularly, intra-molecularly, or both. In certain preferred embodiments, the crosslinked polymer molecules are crosslinked via disulfide bonds.

The crosslinked network of polymer molecules may have a crosslinking density from about 2% to about 80%, relative to the total number of structural units in the polymer. For example, the crosslinked network of polymer molecules may have a crosslinking density from about 2% to about 70%, from about 2% to about 60%, from about 2% to about 50%, from about 2% to about 40%, from about 2% to about 30%, from about 2% to about 20%, from about 2% to about 10%, from about 5% to about 80%, from about 10% to about 80%, from about 20% to about 80%, from about 30% to about 80%, from about 40% to about 80%, relative to the total number of structural units in the polymer.

Any suitable therapeutic, diagnostic or imaging agents may be employed according to the compositions, systems and methods disclosed herein. In some embodiments, the therapeutic agent is an anti-tumor agent, for example, an anti-tumor agent is selected from doxorubicin, paclitaxel, camptothecin, rapamycin, and related chemotherapeutic drugs.

In certain preferred embodiments, the drug is an antidote to an opioid drug (e.g., morphine, fentanyl, alfentanil, heroin, hyrocodone, oxycodone, and opium). In certain preferred embodiments, the drug is an antidote to another drug molecule that causes toxicity at certain concentrations. In certain preferred embodiments, the drug is naloxone.

The loading weight percentage of the guest may be from about 0.5% to about 70% (e.g., from about 0.5% to about 60%, from about 0.5% to about 50%, from about 0.5% to about 40%, from about 0.5% to about 30%, from about 1% to about 70%, from about 2% to about 70%, from about 5% to about 70%, from about 10% to about 70%, from about 20% to about 70%, from about 30% to about 70%).

The biological site of delivery may be present on the surface of or within an organ or tissue, such as lungs or tumor tissue, of a subject.

The biological site of delivery may be on the surface of or inside a cell, such as the interstitial spaces or the interiors of a tumor cell of a subject.

In addition, nanogels of the invention are capable of encapsulating hydrophobic small molecules within its crosslinked interiors and binding proteins on its surface through electrostatic interactions. The nanogels may be functionalized with cell penetrating peptides efficiently. The nanogels bind oppositely charged proteins and that the charge density on the nanogel surface affects the efficiency of binding of the complementarily charged proteins. Complexation of the protein with the nanogel does not alter the activity of the protein, and both the hydrophobic small molecule and the protein are concurrently taken up by cells. The enzymatic activity remains intact even upon cellular entry. The protein may also be covalently attached to the nanogel. Such design strategy outlined herein can have been applied in a variety of areas including therapeutics, diagnostics, and a combination of the two by way of nano-theranostics.

Ligand functionalization may be utilized to decorate nanogels with cell targeting ligands. The ligand-decorated nanogels exhibit facilitated receptor-dependent cellular uptake. The selective internalization capability can be used to delivering chemotherapeutic drugs to a specific receptor-rich cells. The versatile one-pot synthetic method for synthesizing the ligand-decorated nanogels, combined with the intrinsic encapsulation stability and targeting capabilities of the formed T-NGs, open up new avenues in targeted drug delivery for crosslinked polymer nanogels.

Polymeric nano-assemblies selected, modified, fine-tuned according to methods disclosed herein have the desired properties and characteristics such as proper particle side distribution and morphology, encapsulation stability, desired loading capacity and release profile, etc.

Effect of Hydrophobicity on Guest Loading and Encapsulation Stability

To probe the effect of hydrophobic variations on encapsulation and the dynamics of guest exchange, the hydrophilic-lipophilic balance (HLB) was varied in the assembled polymer architecture of the nanogel system. Modifying the oligoethylene glycol (OEG)-pyridyldisulfide (PDS) copolymer to include hydrophobic alkyl chains (FIG. 1) allowed changes in HLB of the precursor polymer and the variations in lipophilic loading parameters. Also investigated were the consequences of such alterations on the dynamic exchange of sequestered guest molecules between the nanogel container and the surrounding aqueous environment.

Dynamics of Guest Exchange

Figure 2:
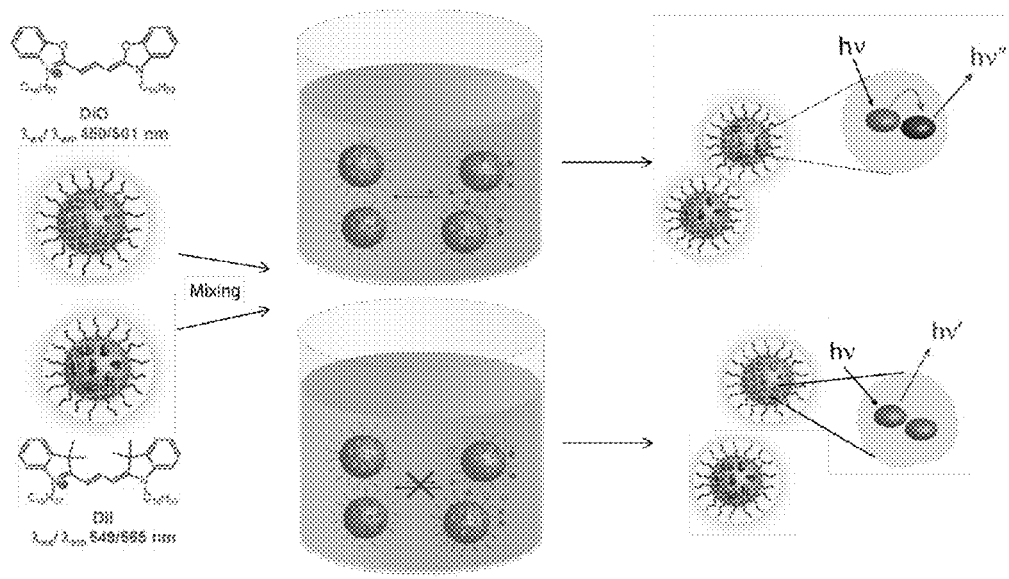
FIG. 2. Schematic illustration of potential FRET outcomes upon mixing solutions of DiI/DiO encapsulating nanocarriers. Low encapsulation stability (top) permits dye leakage, equilibration and causes FRET development. High encapsulation stability (bottom) prevents dye exchange and negates FRET development.

A FRET-based assay was used to monitor the dynamics of guest exchange. (Jiwpanich, et al. 2010 *J. Am. Chem. Soc.* 132, 10683-10685.) According to this method, nanogels separately encapsulating the lipophilic FRET pair dyes, $DiOC_{18(3)}$ (DiO) and $DiIC_{18(3)}$ (DiI), are prepared. When solutions of these dye-containing carriers are mixed, two distinct outcomes (FIG. 2) are possible. If the dye molecules are stably encapsulated within the nanogel interior, they will not exchange with the bulk solvent environment and will remain within their original carriers; therefore, no FRET development will be observed in the mixed solution. If encapsulation stability is compromised, guest exchange will occur when the two solutions are mixed, causing time-dependent equilibration of the dye molecules among all the indistinguishable nanogel carriers in solution. This equilibration will cause DiI and DiO molecules to occupy the same interior, placing them within range of the Förster radius and leading to an increase in observed FRET. Thus, tracing the evolution of FRET in the mixed solutions, as measured by concomitant decrease in donor (DiO) emission intensity and increase in acceptor (DiI) emission intensity, provides insight into the stability of guest molecule encapsulation, the dynamics of guest exchange with the bulk environment and potential nanocarrier leakage.

Design and Syntheses of Polymers and Nanogels

To test the effects of varying hydrophobicity, amphiphilic random copolymer precursors of varying hydrophobic content were synthesized (Chart 1). Drawing from the OEG-PDS copolymer, which uses the PDS side chains as handles for chemically cross-linking the nanogel structure, the polymer precursors were designed to have a constant amount of the PDS functionality. To develop a fundamental correlation between nanogel hydrophobicity and encapsulation stability, it was deemed necessary to keep crosslinking density low in these nanogels so that guest exchange would likely be observed and trends could be drawn from the data. Thus, the PDS-derived methacrylate monomer was selected to comprise only 20% of all the studied precursor polymers. The OEG methacrylate monomer was incorporated to provide a water soluble, charge-neutral side chain and constitute the hydrophilic content of the precursor polymers. To achieve polymers with varied hydrophobic content, lipophilic alkyl chain-derived monomers were added to this OEG-PDS composition. The relative hydrophobicities of the precursor polymers were varied by altering the percent composition of this comonomer containing an alkyl chain of constant length.

For the series, three polymers (P1-P3) were prepared with varying percentages of incorporated decyl methacrylate comonomer. The feed ratio of this hydrophobic unit to OEG was varied, while keeping the PDS unit at a constant 20%. In synthesizing P1-P3, a polymer series was generated in which the targeted ratios of OEG methacrylate to decyl methacrylate to PDS methacrylate were made to equal 5:3:2, 4:4:2 and 3:5:2, respectively. The incorporated ratios of these monomers, as determined by integration of the $^1$H NMR spectra, were observed to closely match these feed ratios (Chart 1). All precursor polymers were prepared by reversible addition-fragmentation chain transfer (RAFT) polymerization.

Chart 1. Structures and characterizations of the precursor polymers P1-P3.

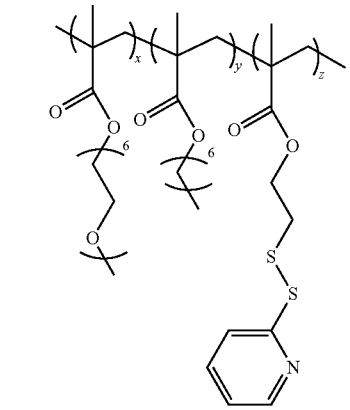

P1; x:y:z = 0.50n:0.33n:0.17n; Mn: 49K; PDI: 2.1
P2; x:y:z = 0.42n:0.43n:0.15n; Mn: 42K; PDI: 2.0
P3; x:y:z = 0.34n:0.50n:0.16n; Mn: 52K; PDI: 2.2

Polymer precursors P1-P3 were observed to form nanoscale aggregates upon self-assembly in aqueous solution. Aggregation of the amphiphilic copolymers generated assemblies with hydrophobic cores that could accommodate the sequestration of hydrophobic guest molecules in water. The nanogel samples were prepared by in situ loading of hydrophobic dyes into the polymer aggregates. Dye encapsulation, initiated by addition from a dye stock solution to the polymer solution (both in acetone), was promoted by dilution with deionized water and gradual removal of acetone from the mixture. Subsequent addition of the reducing agent, dithiothreitol (DTT, 50 mol % with respect to the PDS groups in the precursor polymer), activated the intra/interchain disulfide bond formation that has been shown to generate the crosslinked polymer nanogel structure. (Ryu, et al. 2010 *J. Am. Chem. Soc.*, 132, 17227-17235; Ryu, et al. 2010 *J. Am. Chem. Soc.*, 132, 8246-8247.) The progress of this reaction was monitored by tracking the production of the pyridothione byproduct through its characteristic absorption at 343 nm. With the formation of each crosslinking disulfide bond requiring two PDS groups, addition of 50 mol % DTT was observed to remove nearly all the PDS groups during the crosslinking procedure. From this reaction, dye loaded polymer nanogels NG1-NG3 were prepared from polymer precursors P1-P3 (Scheme 1), achieving noncovalent hydrophobic guest encapsulation within the obtained crosslinked, water soluble nanogels.

Scheme 1. Synthesis of self-crosslinked polymer nanogels (NG1-NG3)

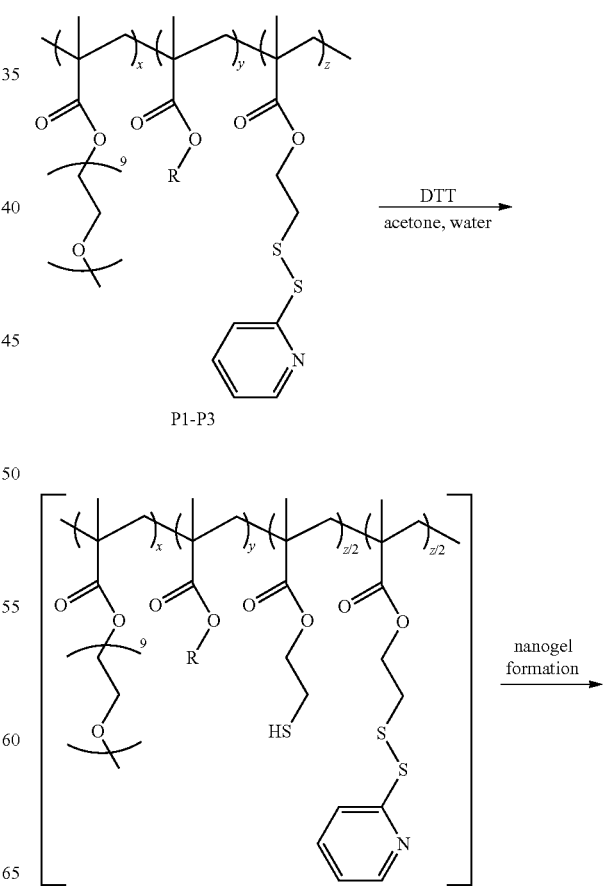

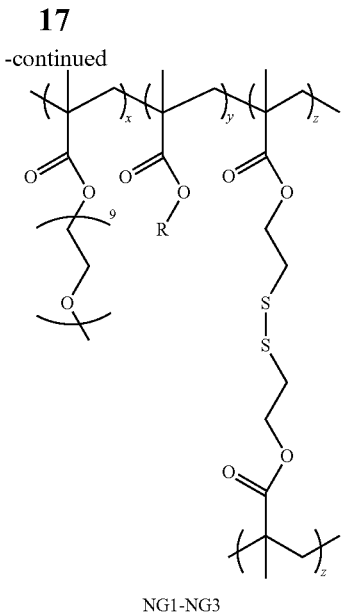

NG1-NG3

R = Decyl Chain

Figure 3:
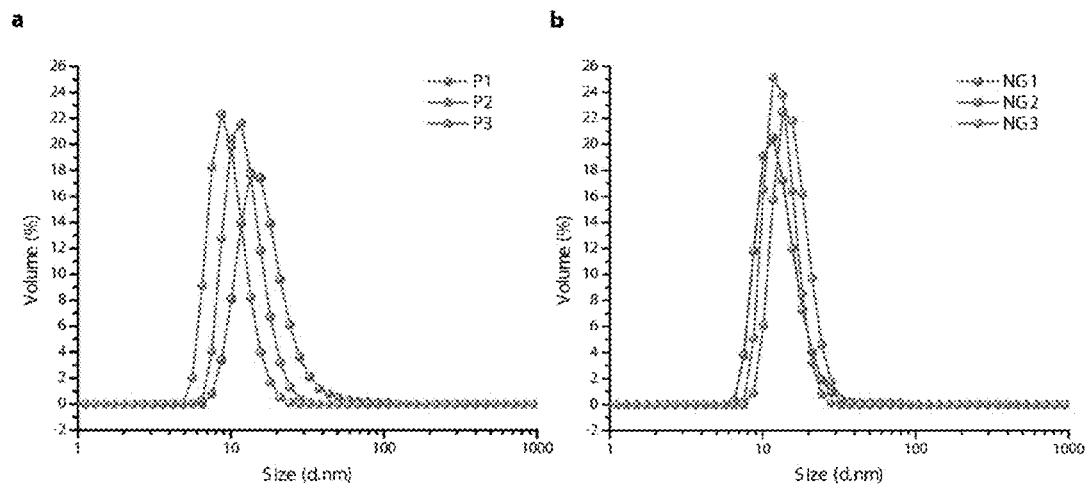
FIG. 3. Size distributions as measured by volume based DLS for aqueous solutions (1 mg $mL^{-1}$) of a) polymer aggregates of P1-P3 and b) self-crosslinked polymer nanogels NG1-NG3.

The aggregation sizes of polymers P1-P3 in water prior to cross-linking were investigated by dynamic light scattering (DLS). Aqueous solutions of P1-P3 (1 mg mL$^{-1}$) exhibited aggregate sizes with diameters centered at 9-14 nm (FIG. 3a). The nanogels NG1-NG3 (1 mg mL$^{-1}$) formed from these polymers were observed to have more narrow size distributions, with average diameters centered at 12-14 nm by DLS measurement (FIG. 3b).

Non-covalent Encapsulation of Hydrophobic Guest Molecules

Figure 4:
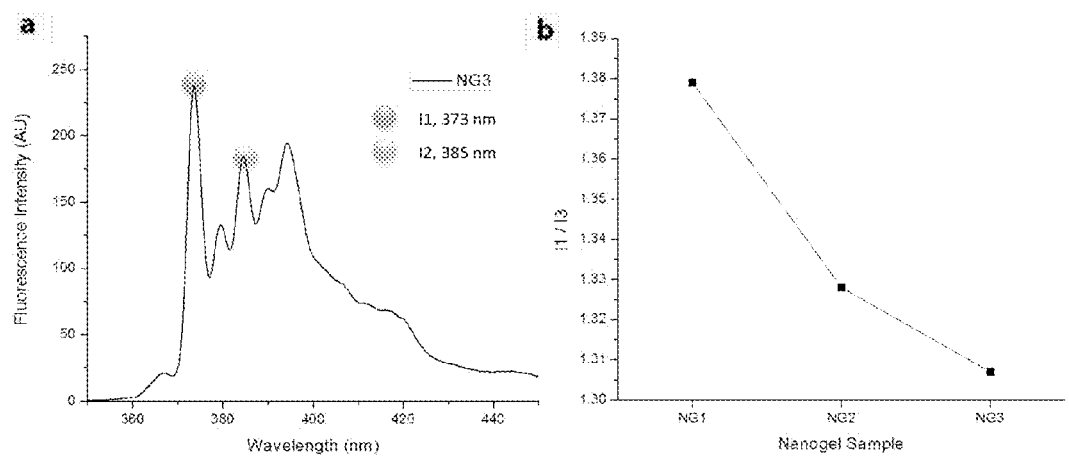
FIG. 4. (a) Fluorescence emission spectrum recorded for NG3 prepared with 10 wt % pyrene feeding; (b) Calculated $I_1/I_3$ ratios for pyrene encapsulated in the NG1-NG3 samples.

Nanogels NG1-NG3 were prepared in the presence of 10 wt % pyrene. After purification of the nanogel samples by filtering off unencapsulated dye and dialysis against deionized water, the fluorescence emission spectra of the samples were recorded. A sample fluorescence spectrum of NG3 is shown in FIG. 4a (the first and third emission maxima highlighted in red and blue, respectively). The ratio of the first and third emission intensities of pyrene, commonly referred to as the $I_1/I_3$ ratio, has been shown to correlate with the polarity of the dye's environment, with values ranging from 1.9 in polar solvents to 0.6 in certain hydrocarbon solvents. (Kalyanasundaram, et al. 1977 J. Am. Chem. Soc. 99, 2039.) Thus, the $I_1/I_3$ values for pyrene encapsulated in NG1-NG3 were calculated to probe the relative polarities of the nanogel carriers. Going through NG1-NG3, a trend of decreasing value in the pyrene $I_1/I_3$ ratio was observed, indicating the dye's encapsulation in an increasingly nonpolar environment (FIG. 4b). Thus, as the percentage of decyl chain component in the precursor polymer is increased, the resulting nanogel container becomes more hydrophobic. The $I_1/I_3$ values of the nanogel samples range from 1.38 (NG1) to 1.31 (NG3).

Figure 15:
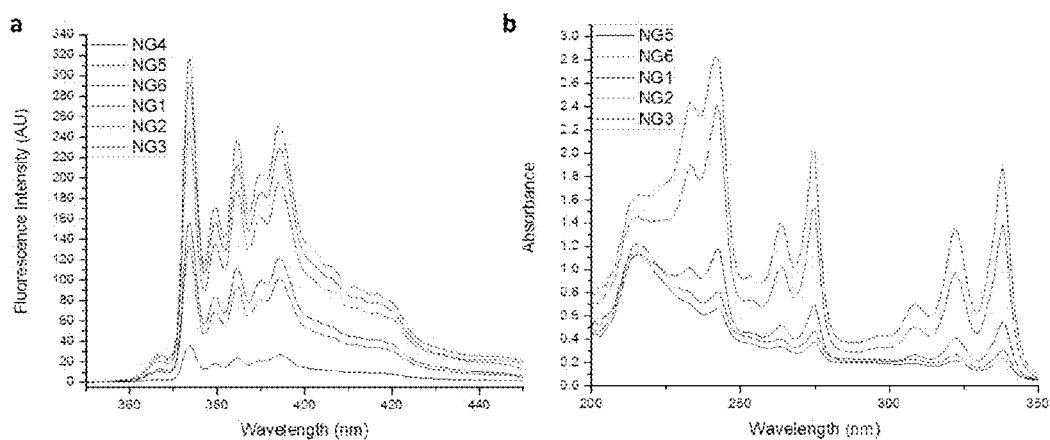
FIG. 15. (a) Fluorescence spectra of NG1-NG6 samples prepared with 10 wt % pyrene from which the reported $I_1/I_3$ values were calculated; (b) UV-Vis spectra of NG1-NG3 and NG5-NG6 samples (1 mg mL$^{-1}$) prepared with 10 wt % pyrene reveal a trend of enhanced pyrene loading with increased nanogel hydrophobicity.

Analyses of the pyrene absorbance spectra (FIG. 15) show that the increasing hydrophobicities of the containers from NG1-NG3 may generate more favorable environments for hydrophobic guest encapsulation and afford enhanced loading capacities. To investigate the extent of guest loading in these nanogels, samples of NG1-NG3 were prepared by the DTT-initiated crosslinking reaction in the presence of both 10 wt % DiI and 10 wt % DiO to afford noncovalent encapsulation of the FRET pair dyes within the nanogel interiors. After filtering off excess dye and removing water-soluble byproducts of the crosslinking reaction by dialysis, guest encapsulation in these nanogels was measured by UV-visible spectroscopy. The absorption spectra of the dye loaded nanogels, shown in FIG. 5, reveal a trend of increasing dye encapsulation as the hydrophobic content of the nanogel is increased from NG1-NG3.

Effect of Hydrophobicity on Encapsulation Stability

To investigate encapsulation stability of the guest-loaded nanocarriers, the FRET-based assay (FIG. 2) was used to compare the encapsulation stabilities exhibited by DiI/DiO loaded NG1-NG3. Nanogel samples having encapsulated DiI were mixed with those having encapsulated DiO, with both nanogels having equal concentrations of 0.1 mg mL$^{-1}$ in the resulting mixture. The evolution of FRET between the dye pair in mixed solutions of NG1-NG3, indicated by concomitant decrease in donor (DiO) emission intensity at 506 nm and increase in acceptor (DiI) emission intensity at 569 nm, was recorded over a six hour period.

Figure 6:
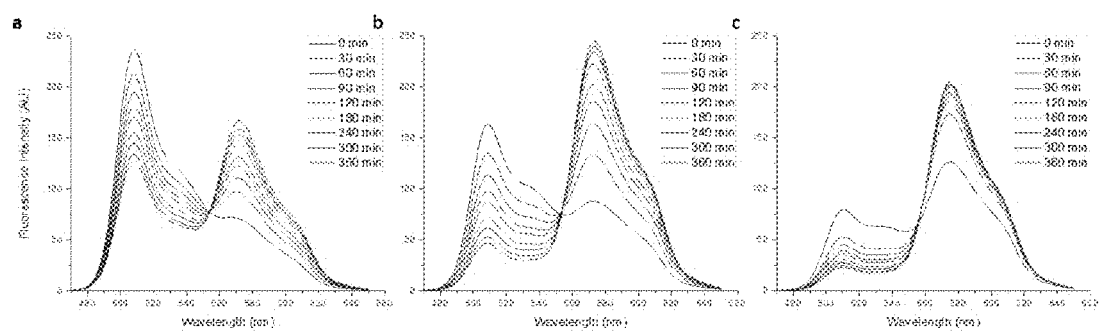
FIG. 6. Fluorescence spectra of mixed solutions of NG1-NG3 (left to right) prepared with 10 wt % DiI/DiO tracing the development of FRET over time.

FIG. 6 shows the time-dependent FRET evolution as observed in the fluorescence spectra of these mixed nanogel solutions. These solutions exhibit faster rates of FRET development for the more hydrophobic nanogel containers, suggesting that increasing hydrophobicity actually decreases the encapsulation stability of the nanocarrier. However, there is significant variation in the loading amounts of DiI and DiO among these samples. It is possible that this difference in dye loading, a consequence of the variations in nanogel hydrophobicity, influences the observed dye exchange rates. NG1 exhibited the lowest dye encapsulation with 10 wt % feeding, but also displayed the most gradually increasing FRET over the tested six hour period (FIG. 6a). NG2 encapsulated an intermediate amount of dye and exhibited much faster FRET development (FIG. 6b). NG3 encapsulated the highest amount of dye and displayed a rapid burst of FRET evolution, with the majority of observable exchange occurring within the first hour of the experiment (FIG. 6c).

Figure 5:
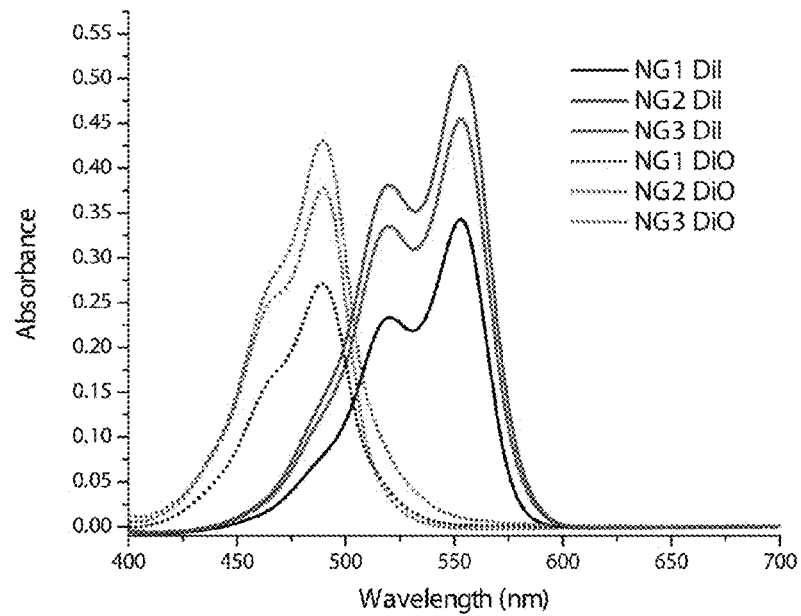
FIG. 5. UV-Vis spectra of NG1-NG3 prepared with 10 weight % (wt %) dye feeding (spectra recorded at 0.05 mg·$mL^{-1}$ nanogel) showing the effect of nanogel hydrophobicity on DiI/DiO loading.
Figure 7:
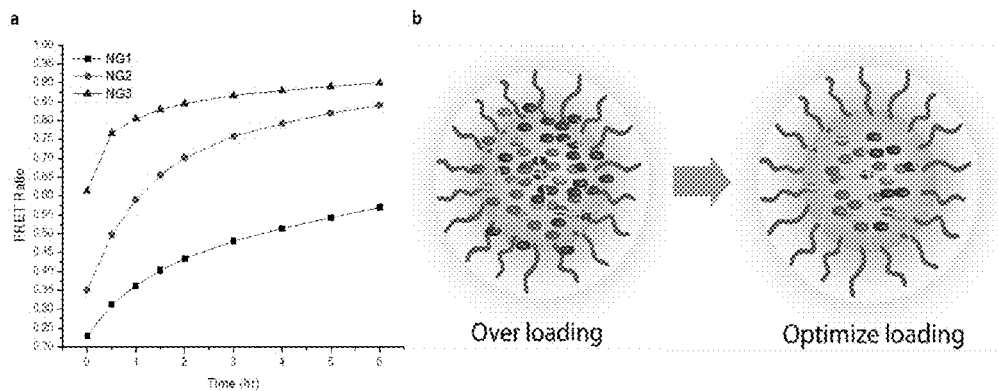
FIG. 7. (a) FRET ratio vs. time plot of the mixed solutions of NG1-NG3 prepared with 10 wt % DiI/DiO; (b) Schematic illustration of an overloaded nanogel with low encapsulation stability and an optimally loaded nanogel with high encapsulation stability.

The apparent inverse relationship between loading amount and encapsulation stability is seen in the plots of FRET ratio vs. time for the 10 wt % NG1-NG3 series (FIG. 7a). The FRET ratio $I_a/(I_d+I_a)$, where $I_a$ and $I_d$ are the fluorescence intensities of the acceptor (DiI) and donor (DiO), respectively, can be used as a measure of the degree of FRET between the dye pair and, thus, the extent of dye exchange observed in each mixed nanogel solution. In all the prepared nanogel samples, the amount of encapsulated DiI exceeded that of DiO (FIG. 5). The maximum allowed FRET ratio for each mixed solution is 1.0, achieved only when every DiO molecule can transfer energy to a sufficiently proximal DiI molecule. From FIG. 7a, it is observed that NG2 and NG3 are nearing this theoretical plateau at the end of the six hour test period. Additionally, there are large differences in the initial FRET ratios of these mixed solutions, with the values increasing from NG1 (0.23) to NG3 (0.61). While self-quenching of DiO emission might have a small contribution to this observation, the trend indicates that, with the rapidly exchanging NG2 and NG3, a significant amount of dye exchange occurs immediately upon mixing of the solutions before the first emission spectrum is recorded.

The development of FRET observed by this method is dependent on two separate events. The first is leakage of dye molecules from the interior of the originally encapsulating nanogel into the aqueous exterior. The second is re-sequestration of the leaked dye molecules into the interiors of nanogels present in solution. The inability of the leaked dye molecules to discriminate between the nanogels in solution causes the previously described equilibration and FRET evolution. The results obtained with the 10 wt % NG1-NG3 series indicate that the total amount of encapsulated dye may significantly influence the probabilities of these processes happening and the rates at which they occur. This observation supports loading-dependent encapsulation stability.

FIG. 5 shows that the capacity for hydrophobic encapsulation is enhanced as the amount of decyl chains incorporated within the precursor polymer increases. The amphiphilic nature of polymers P1-P3 induces formation of nanoscale aggregates, in which the majority of hydrophobic content is buried within the cores. A possible feature of hydrophobic guest encapsulation in these aggregates is that initially sequestered guest molecules accumulate deep within the core and gradually move out towards the assembly periphery as the core volume is filled. In this case, the extent of such peripheral loading will likely depend on the nature (length and density) of the hydrophobic units dispersed throughout the copolymer network, the size of the nanocarrier core and the amount of dye used during nanogel preparation. Thus, as the percent composition of decyl chains is increased from NG1 to NG3, the observed increase in loading capacity may, in part, be due to an enhanced ability to load hydrophobic dye molecules closer to the nanogel surface. However, it is also reasonable to propose that these non-optimally loaded dye molecules will be least stably encapsulated and most easily exchange with the bulk environment. This would explain why the enhanced dye loading observed from NG1 to NG3 translates to more rapid guest exchange and faster FRET evolution. FIG. 7b indicates that a given nanogel carrier should be loaded below its maximum loading capacity in order to achieve optimal core loading and high encapsulation stability.

Loading Capacity and Encapsulation Stability

NG1-NG3 samples with lower guest loading, i.e. in the presence of 2 wt % and 0.5 wt % DiI/DiO, were prepared. The observed dye loadings, indicated by the calculated encapsulation efficiencies for these nanogels, are summarized in Table 1. As dye feeding decreases, the encapsulation efficiencies of both DiI and DiO increase and the observed dependence of loading capacity on nanogel hydrophobicity diminishes. This effect is most apparent with the dye loading efficiencies among NG1-NG3 fed with 0.5 wt % DiI/DiO, which are nearly identical and exhibit complete DiI encapsulation and close to 90% DiO encapsulation for all samples.

At lower loading, similar loading efficiencies were observed for both DiI and DiO among the three nanogel carriers. With such normalized loading, a larger percentage of the dye content in these samples would be stably encapsulated in the nanogel core. In this case, the observed rates of guest exchange in these nanogel carriers should provide a true correlation between hydrophobicity of the supramolecular host's interior and encapsulation stability for hydrophobic guest molecules.

Figure 8:
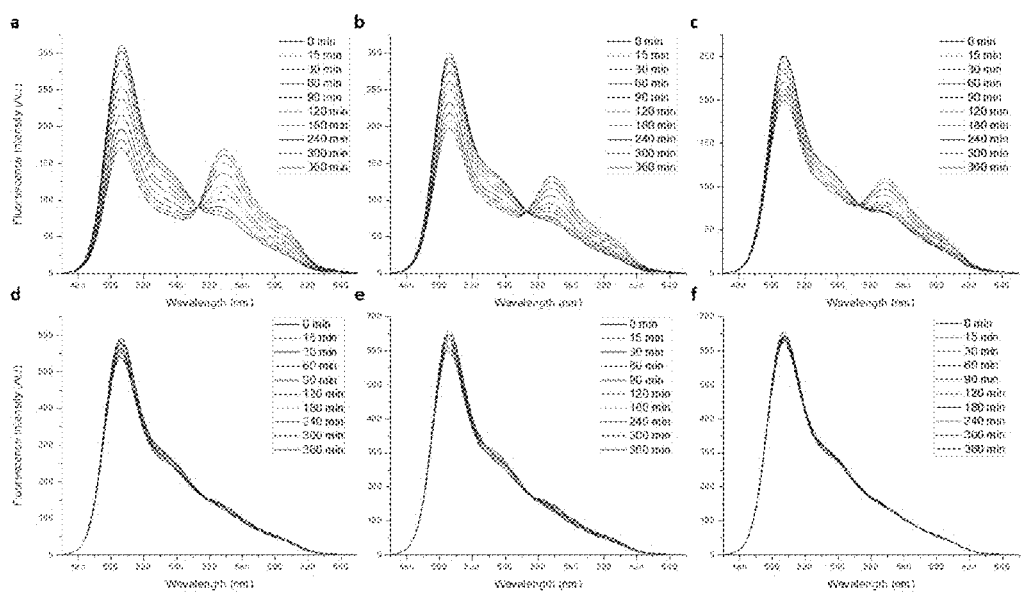
FIG. 8. Fluorescence spectra of the mixed solutions of NG1-NG3 (left to right) prepared with (a-c) 2 wt % and (d-f) 0.5 wt % DiI/DiO tracing the development of FRET between the dyes over time.

Analysis of the fluorescence spectra from the mixing experiments (FIG. 8) indicates that increasing the hydrophobicity of the nanogel enhances the carrier's encapsulation stability. In the case of the 2 wt % samples (FIG. 8a-8c), dye molecule exchange evidenced by FRET evolution is observed to decrease from NG1 to NG3, presumably due to the more preferable encapsulation environment afforded by the increasingly hydrophobic nanogel core. Furthermore, with the 0.5 wt % samples (FIG. 8d-8f), very little to no dye exchange is observed for all three mixed nanogel solutions over the course of the experiment. Independently, these mixing experiments reveal the same trend; as the hydrophobic content of the nanogel container is increased from NG1 to NG3 the likelihood of guest leakage into the bulk solvent, and thus the rate of observed FRET evolution, is decreased.

TABLE 1

| | Dye encapsulation efficiencies for | | | | | |
|---|---|---|---|---|---|---|
| | 10 wt % Dye Feeding [b] | | 2 wt % Dye Feeding [c] | | 0.5 wt % Dye Feeding [d] | |
| Sample [a] | DiI | DiO | DiI | DiO | DiI | DiO |
| NG1 | 43% | 34% | 89% | 68% | >95% | 85% |
| NG2 | 57% | 47% | >95% | 73% | >95% | 87% |
| NG3 | 65% | 54% | >95% | 70% | >95% | 88% |

[a] All nanogels were prepared with 2 mg polymer total scale at 1 mg mL$^{-1}$. Reported encapsulation efficiencies were calculated based on dye feedings of
[b] 0.225 mg DiI/0.205 mg DiO;
[c] 0.045 mg DiI/0.041 mg DiO;
[d] 0.011 mg DiI/0.010 mg DiO.
NG1-NG3 were prepared with 10, 2 and 0.5 wt % DiI/DiO.

Figure 9:
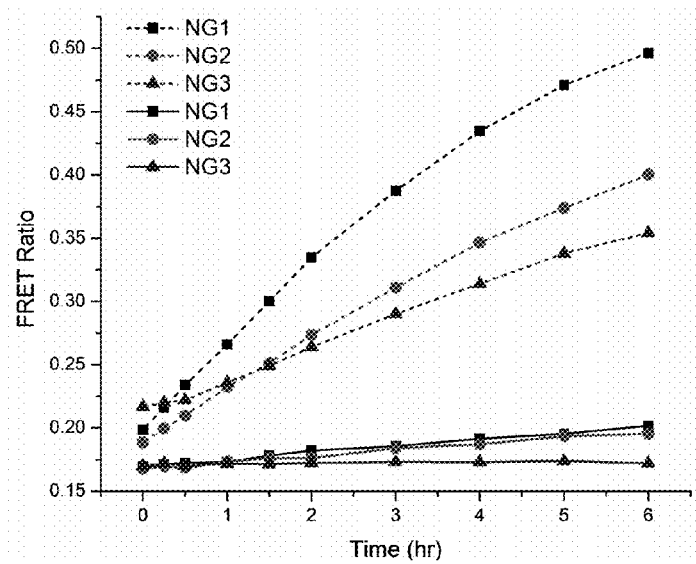
FIG. 9. FRET ratio vs. time plots of the mixed solutions of NG1-NG3 prepared with 2 wt % (dashed lines) and 0.5 wt % (solid lines) DiI/DiO.

This trend is most clearly seen in the plots of FRET ratio vs. time for the mixed solutions of the 2 wt % and 0.5 wt % samples (FIG. 9). To compare the rates of guest exchange exhibited by the NG1-NG3 series, the slopes of the linear fits to the plots of FRET ratio vs. time were calculated. This slope value is defined as the leakage coefficient ($\Lambda$), a quantitative relation to the rate of guest exchange between the assembly interior and the bulk solvent exhibited by a mixed nanocarrier solution. (Jiwpanich, et al. 2010 J. Am. Chem. Soc. 132, 10683-10685; Note that the plots used in this previous work were of normalized FRET ratio vs. time.) From plotting FRET ratios vs. time, the slope of the portion of this plot was determined that can be accurately fit by a linear regression ($R^2 \geq 0.95$). This slope value is defined as the corrected leakage coefficient ($\Lambda_c$), and has been used to compare the dynamics of guest exchange exhibited by the studied nanogels.

The calculated $\Lambda_c$ values for the NG1-NG3 series prepared with 10 wt %, 2 wt % and 0.5 wt % DiI/DiO are listed in Table 2, which reveals the clear difference in trend observed with the 10 wt % samples. The significant increase in $\Lambda_c$ value from NG1 to NG3 in this series lends support to the claim that the 10 wt % samples fit the overloaded nanogel model previously described. With greater numbers of decyl units, the more hydrophobic NG2 and NG3 exhibit higher capacity for guest loading in regions that do not provide sufficient encapsulation stability to prevent leakage into the bulk exterior. Thus, an inverse relationship between nanogel hydrophobicity and encapsulation stability is observed.

In contrast, the samples prepared with 2 wt % and 0.5 wt % dye more closely fit the optimally loaded nanogel model, in which the majority of encapsulated dye molecules are stably sequestered within the cores. As a result, the expected trend of enhanced encapsulation stability with increasing nanogel hydrophobicity is observed with these samples. Additionally, among nanogel samples of the same composition (e.g. all NG1), the corrected leakage coefficient value is observed to decrease with lower dye loading.

Taken together, these results support that optimal encapsulation, at which little to no guest exchange between containers in solution and the dispersing solvent exists, is achieved well below the maximum loading capacity of a nanocarrier.

TABLE 2

Calculated $\Lambda_c$ values for the NG1-NG3

| Dye Loading | NG1 | NG2 | NG3 |
|---|---|---|---|
| | | $\Lambda_c$ (h$^{-1}$) | |
| 10 wt % | 0.100 | 0.173 | 0.308 |
| 2 wt % | 0.051 | 0.036 | 0.024 |
| 0.5 wt % | 0.005 | 0.005 | 0.000 |

Hydrophobicity Modification by Alkyl Chains

A second nanogel system was studied, in which the relative hydrophobicities of the precursor polymers were varied by simply altering the lengths of the incorporated alkyl chain derived comonomers. This variation allows for further testing the observed encapsulation stability trends with a second, independent nanogel series that retains constant percent compositions of the hydrophilic OEG-based and hydrophobic alkyl-substituted units. The targeted precursor polymers, which were also synthesized by RAFT polymerization, are shown in Chart 2. For this series, three polymers (P4-P6) were prepared to contain 50% OEG methacrylate, 20% PDS-derived methacrylate and 30% alkyl chain-derived methacrylate. Within this polymer series, the alkyl chain (R) length was varied to generate polymers P4 (R=butyl), P5 (R=hexyl), P6 (R=octyl). It should be noted that P1 (R=decyl) can be placed at both the end of this series and the beginning of the first series, creating a continuous variation between these polymers and the P1-P3 series and between the hydrophobicities of their corresponding nanogels.

Chart 2. Structures and characterizations of the polymer precursors P1 and P4-P6

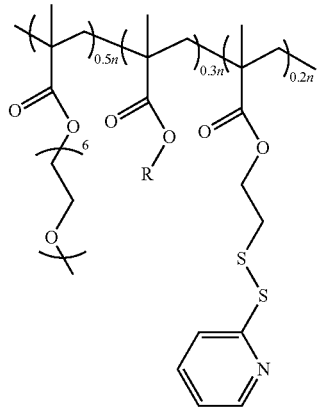

P4; R = CH$_2$(CH$_2$)$_2$CH$_3$; x:y:z = 0.50n:0.33n:0.17n; Mn: 55K; PD1: 2.2
P5; R = CH$_2$(CH$_2$)$_4$CH$_3$; x:y:z = 0.49n:0.33n:0.18n; Mn: 38K; PD1: 1.5
P6; R = CH$_2$(CH$_2$)$_6$CH$_3$; x:y:z = 0.50n:0.34n:0.16n; Mn: 41K; PD1: 1.4
P1; R = CH$_2$(CH$_2$)$_8$CH$_3$; x:y:z = 0.50n:0.33n:0.17n; Mn: 49K; PD1: 2.1

Figure 10:
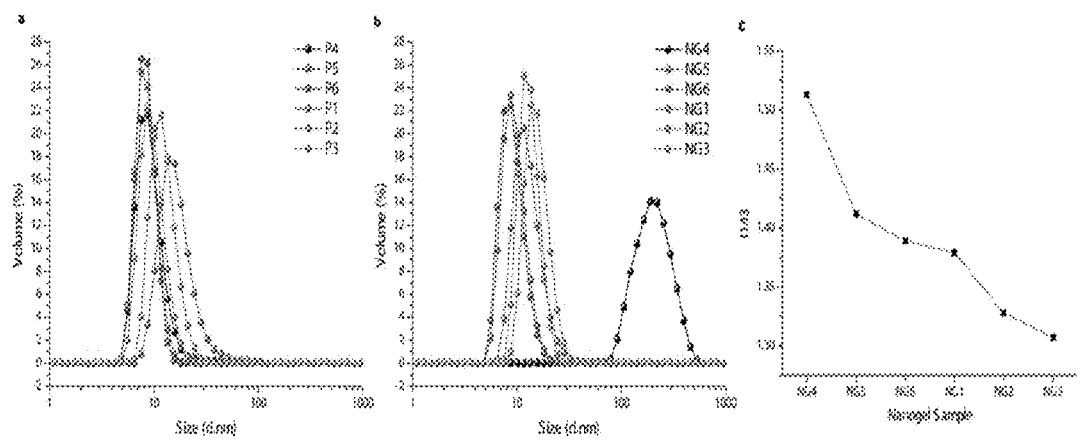
FIG. 10. Size distributions as measured by volume based DLS for aqueous solutions (1 mg·mL$^{-1}$) of (a) polymer aggregates of P1-P6; (b) polymer nanogels NG1-NG6; (c) Calculated $I_1/I_3$ ratios for 10 wt % pyrene encapsulated in NG1-NG6.

Nanogels NG4-NG6, were also prepared using the synthesis outlined in Scheme 1. The aggregate sizes of polymers P4-P6 prior to cross-linking and the assembly sizes of the prepared NG4-NG6 were investigated by DLS. The size distributions of these samples are shown in FIG. 10. Aqueous solutions of polymers P4-P6 (1 mg mL$^{-1}$) exhibited aggregate sizes with diameters centered at 7-9 nm (FIG. 10a). While nanogels NG5 and NG6 (1 mg·mL$^{-1}$) were similar in size, with average diameters centered at around 9 nm, butylmethacrylate containing NG4 exhibited a much larger nanogel size centered at a 190 nm diameter (FIG. 10b). This discrepancy may be due to a lack of stable polymer aggregation in solutions of P4, which contains the shortest lipophilic side chain used in the present work. Considering the large contribution to the overall aggregate HLB from the 50% of hydrophilic OEG segments, it is likely that this butyl chain does not sufficiently stabilize the observed ~9 nm polymer aggregate. Such instability may increase the occurrence of interchain crosslinking during the DTT initiated reaction, resulting in a larger nanogel than those formed from the more stable aggregates of the other polymers.

This size difference was observed to have a significant effect on the relative hydrophobicity of NG4. Pyrene encapsulating samples of NG4-NG6 were prepared using 10 wt % dye. The fluorescence spectra of these solutions were recorded and the $I_1/I_3$ values were calculated to compare with those of NG1-NG3 (FIG. 10c). The $I_1/I_3$ value for NG4 (1.52) is much higher than those of the rest of the nanogels. Having the shortest alkyl chain and a much larger size, NG4 is likely a more swelled and water filled nanogel structure, creating the most polar encapsulation microenvironment for pyrene. Due to the significantly different size of the nanogel compared to the others in these series, NG4 was not investigated further in this comparative study. The $I_1/I_3$ values of the other nanogel samples range from 1.41 (NG5) to 1.31 (NG3) with a continuously decreasing trend.

Nanogels NG5 and NG6 were prepared in the presence of 10 wt %, 2 wt % and 0.5 wt % DiI/DiO and the encapsulation efficiencies (Table 3) were compared to those observed with NG1-NG3. Similar trends in encapsulation were observed for these nanogel samples. The dependence of loading efficiency on nanogel hydrophobicity was again observed to be much higher in the series loaded with 10 wt % dye. DiI was again observed to encapsulate with higher efficiency than DiO in all cases. A notable difference, however, is the lower encapsulation efficiencies for NG5 in the samples prepared with 2 wt % and 0.5 wt % dye. Even at these lower loading amounts, the relative lack of hydrophobic content in the core of this hexyl-containing nanogel affords a less preferable encapsulation environment than its more hydrophobic octyl- and decyl-containing counterparts.

TABLE 3

Dye encapsulation efficiencies for NG5-NG6

| | 10 wt % Dye Feeding [b] | | 2 wt % Dye Feeding [c] | | 0.5 wt % Dye Feeding [d] | |
|---|---|---|---|---|---|---|
| Sample [a] | DiI | DiO | DiI | DiO | DiI | DiO |
| NG5 | 34% | 13% | 80% | 39% | 82% | 83% |
| NG6 | 39% | 29% | 86% | 68% | >95% | 85% |

Figure 11:
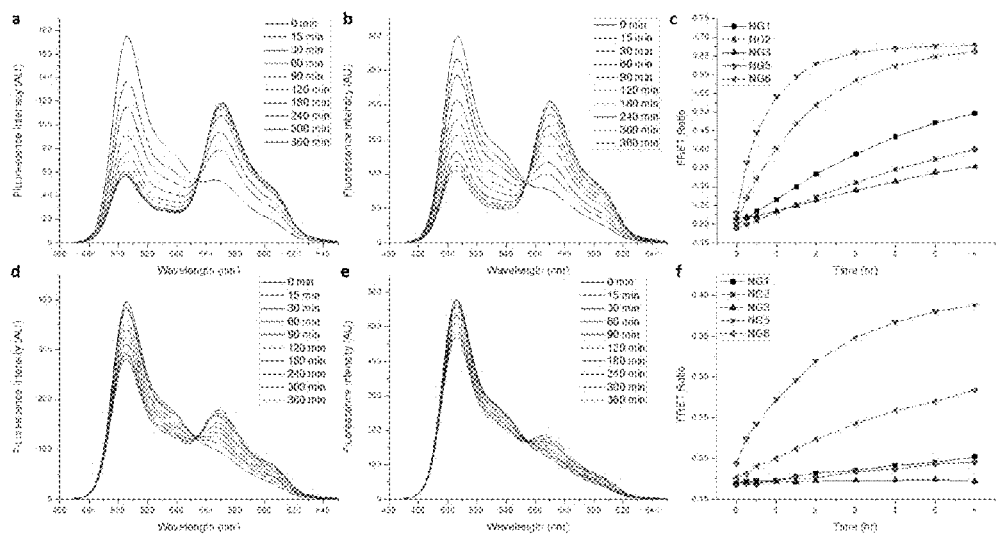
FIG. 11. Fluorescence spectra of the mixed solutions of NG5 (a, d) and NG6 (b, e) prepared with 2 wt % (top) and 0.5 wt % (bottom) DiI/DiO tracing the development of FRET between the dyes over time. Plots of FRET ratio vs. time for all 2 wt % (c) and 0.5 wt % (f) nanogel samples.
Figure 12:
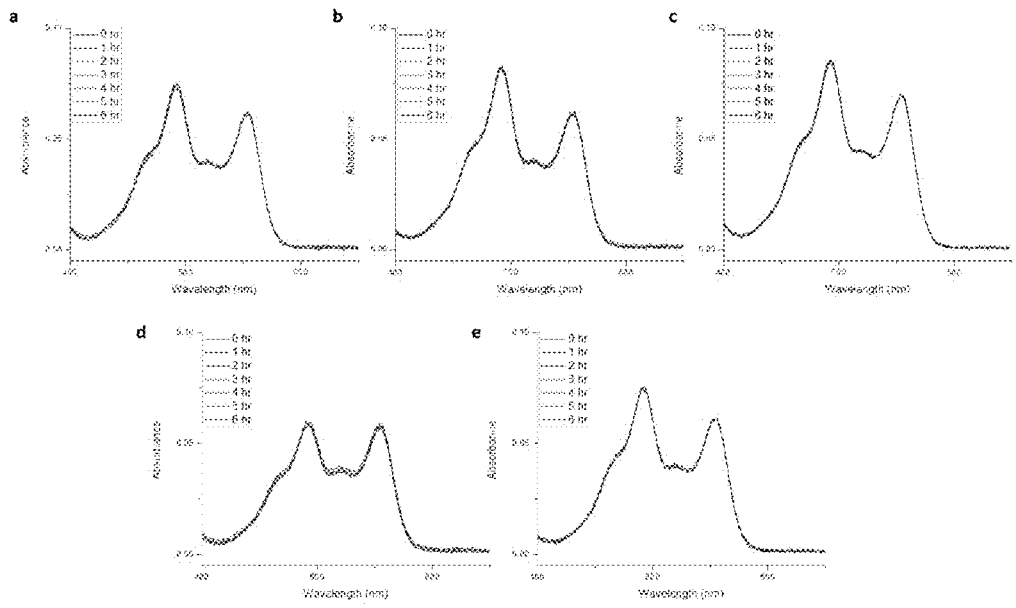
FIG. 12. UV-Vis spectra of NG1 (a), NG2 (b), NG3 (c), NG5 (d) and NG6 (e) taken during the course of mixing experiments performed with nanogel samples prepared with 0.5 wt % DiI/DiO.
Figure 13:
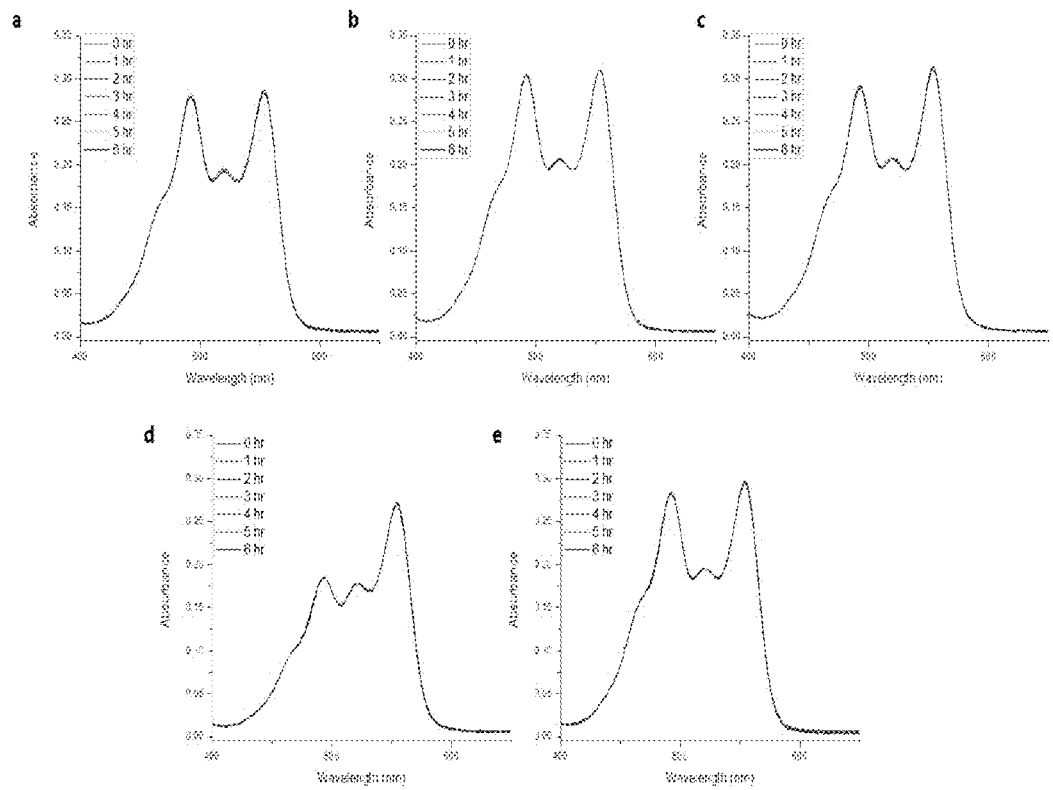
FIG. 13. UV-vis spectra of NG1 (a), NG2 (b), NG3 (c), NG5 (d) and NG6 (e) taken during the course of mixing experiments performed with nanogel samples prepared with 2 wt % DiI/DiO.
Figure 14:
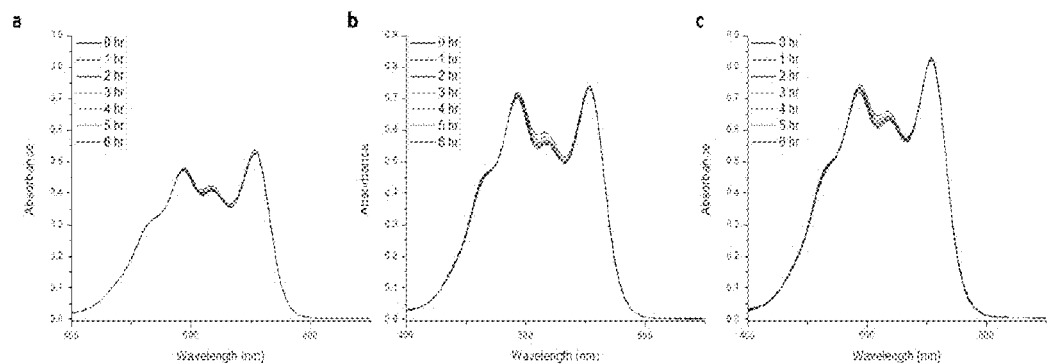
FIG. 14. UV-Vis spectra of NG1 (a), NG2 (b) and NG3 (c) taken during the course of mixing experiments performed with nanogel samples prepared with 10 wt % DiI/DiO.

[a] All nanogels were prepared with 2 mg polymer total scale at 1 mg mL$^{-1}$. Reported encapsulation efficiencies were calculated based on dye feedings of
[b] 0.225 mg DiI/0.205 mg DiO;
[c] 0.045 mg DiI/0.041 mg DiO;
[d] 0.011 mg DiI/0.010 mg DiO.
NG5-NG6 were prepared with 10, 2 and 0.5 wt % DiI/DiO To probe the effect of varying nanogel hydrophobicity on encapsulation stability in this series, mixing studies were performed using the 2 wt % and 0.5 wt % samples for NG5 and NG6. Fluorescence spectra recorded during these experiments are shown in FIG. 11. Additionally, the plots of FRET ratio vs. time are shown with those obtained from the experiments with NG1-NG3. As seen in these plots, the data collected from the mixing of NG5 and NG6 fit very well with that collected from the mixing of NG1-NG3. With 2 wt % loading, both NG5 and NG6 exhibit much faster guest exchange than the NG1-NG3 series. While exchange is more rapid in NG5, both samples are observed to be approaching a FRET ratio plateau of around 0.7 by the end of the six hour test period. With 0.5 wt % loading, the rate of guest exchange is significantly reduced in both NG5 and NG6, but is still much higher than that observed for NG1-NG3, all of which exhibited nearly complete shutdown of guest leakage at this low dye loading. The corrected leakage coefficients for the 2 wt % and 0.5 wt % samples of NG5-NG6 are recorded with those observed for the NG1-NG3 series in Table 4. The consistent trends in the $\Lambda_c$ values of all these samples support the notion that, at optimal loading levels, increasing the hydrophobicity of the nanogel host reduces the dynamic exchange of encapsulated guests between assembly interior and the surrounding environment.

TABLE 4

Calculated $\Lambda_c$ values

| Dye Loading | NG5 | NG6 | NG1 | NG2 | NG3 |
|---|---|---|---|---|---|
| | | | $\Lambda_c$ (h$^{-1}$) | | |
| 2 wt % | 0.434 | 0.126 | 0.051 | 0.036 | 0.024 |
| 0.5 wt % | 0.050 | 0.018 | 0.005 | 0.005 | 0.000 |

For nanogel samples prepared with 2 wt % and 0.5 wt % DiI/DiO

Thus, results disclosed herein establish that: (i) the encapsulation microenvironment of hydrophobic guest molecules sequestered within the nanogels can be systematically altered by either tuning the percentage of hydrophobic alkyl methacrylate co-monomer or varying the length of the alkyl chain in that co-monomer; (ii) the loading capacities and efficiencies, as probed with noncovalent encapsulation of hydrophobic dye molecules, are dependent on nanogel hydrophobicity and can be fine-tuned; (iii) at high dye feeding, the more hydrophobic nanogels exhibit significantly higher guest encapsulation. However, this enhanced loading does not necessarily translate to encapsulation stability; (iv) the observed trend in encapsulation stability at high loading is attributed to the possibility that a smaller percentage of the guest molecules are stably/optimally encapsulated within the nanogel core. At low loading, encapsulation stability follows an excellent correlation with nanogel hydrophobicity; (v) this correlation between encapsulation stability and nanogel hydrophobicity is observed in the low loading samples of two distinct nanogel series, where scaffold hydrophobicity is varied through both the percentage of lipophilic co-monomer and the length of the alkyl chain in the co-monomer.

An issue remains regarding these particular nanogels: do the results here simply suggest that the stable encapsulation of guest molecules in this class of nanogel is restricted to low loading percentages? It is important to recognize that this is not the case, because: (i) The nanogels used in this work are small and have inherently lower loading capacities than larger nanogels that can be generated by this method; (ii) In the studied systems, the percent crosslinking was intentionally limited to afford leaky nanogels that allowed further development of the fundamental structure-property relationship. The stability of guest encapsulation in these nanogels can be significantly enhanced by increasing the crosslinking density.

Consideration of the dynamic guest exchange between a supramolecular host and the bulk solvent environment is critical for several applications. For example, if a host is used as a drug delivery vehicle, any exchange of guest molecules during circulation will likely cause leakage of non-covalently encapsulated cargo, accumulation at off-target sites and give rise to adverse side effects. Stable encapsulation of non-covalently bound guest molecules and specifically triggered release in response to a chosen stimulus are thus crucial design criteria for supramolecular hosts. Inherently high loading capacities and efficiencies in a supramolecular host are not sufficient qualifying criteria for applications such as targeted drug delivery. Also important is to evaluate the percentage of this loading that is stably encapsulated within the nanocarrier.

TABLE 5

$I_1$, $I_3$, and $I_1/I_3$ values from pyrene fluorescence spectra
(10 wt % loaded NG1-NG6 from two repeated experiment trials)

| | $I_1$ (Trial 1/Trial 2) | $I_3$ (Trial 1/Trial 2) | $I_1/I_3$ |
|---|---|---|---|
| NG1 | 294.266/308.328 | 213.453/226.512 | 1.38/1.36 |
| NG2 | 316.279/328.17 | 238.187/251.324 | 1.33/1.31 |
| NG3 | 245.211/237.468 | 187.597/185.13 | 1.31/1.28 |
| NG4 | 36.138/36.176 | 23.997/23.860 | 1.51/1.52 |
| NG5 | 132.743/135.565 | 94.081/96.099 | 1.41/1.41 |
| NG6 | 155.886/166.179 | 112.357/120.337 | 1.39/1.38 |

TABLE 6

Calculated $\Lambda_c$ values for all nanogel samples

| Dye Loading | NG5 | NG6 | NG1 | NG2 | NG3 |
|---|---|---|---|---|---|
| | | | $\Lambda_c$ (h$^{-1}$) | | |
| 0.5 wt % | 0.050 | 0.018 | 0.005 | 0.005 | 0.000 |
| 1 wt % | — | — | 0.023 | 0.002 | 0.000 |
| 2 wt % | 0.434 | 0.126 | 0.051 | 0.036 | 0.024 |
| 10 wt % | — | — | 0.100 | 0.173 | 0.308 |

— Prepared with 10 wt %, 2 wt %, 1 wt % (only performed with NG1-NG3) and 0.5 wt % DiI/DiO Experimental 2,2'-Dithiodipyridine, 2-mercaptoethanol, polyethylene glycol monomethyl ether methacrylate (MW 450), butyl methacrylate, hexyl methacrylate, octyl methacrylate, decyl methacrylate, D,L-dithiothreitol (DTT), 1,1'-dioctadecyl-3,3,3',3'-tetramethylindocarbocyanine perchlorate (DiI), 3,3'-dioctadecyloxacarbocyanine perchlorate (DiO), pyrene, and other conventional reagents and solvents were obtained from commercial sources and were used as received unless otherwise mentioned.

Polymers P1-P6 were synthesized by RAFT polymerization and purified by precipitation. S-dodecyl-S'-2-(2,2-dimethylacetic acid)trithiocarbonate and pyridyldisulfide ethylmethacrylate (PDSEMA) were prepared using previously reported procedures. (Lai, et al. 2002 *Macromolecules* 35, 6754-6756; Ghosh, et al. 2006 *Macromolecules* 39, 5595-5597.) $^1$H-NMR spectra were recorded on a 400 MHz Bruker NMR spectrometer using the residual proton resonance of the solvent as the internal standard. Chemical shifts are reported in parts per million (ppm). Molecular weights of the polymers were estimated by gel permeation chromatography (GPC) using a PMMA standard with a refractive index detector. Dynamic light scattering (DLS) measurements were performed using a Malvern Nanozetasizer. UV-visible absorption spectra were recorded on a Varian (model EL 01125047) spectrophotometer. Fluorescence spectra were recorded from a JASCO FP-6500 spectrofluorimeter.

Transmission electron microscopy (TEM) images were taken from JEOL 100CX at 100 KV.

General Procedure for Random Copolymer Synthesis

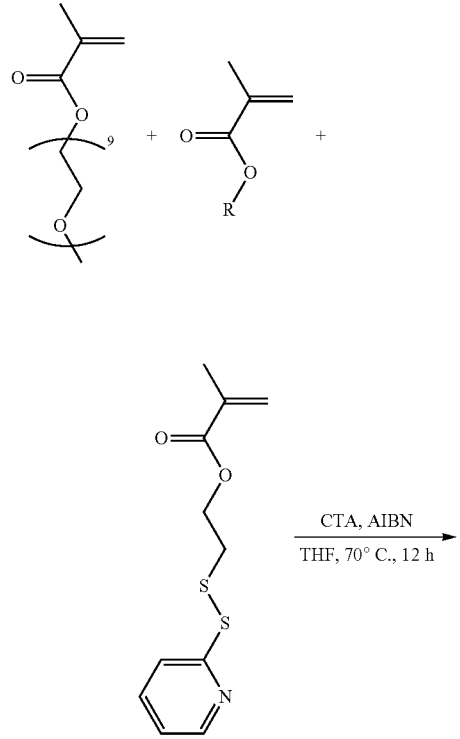

A mixture of S-dodecyl-S'-2-(2,2-dimethylacetic acid) trithiocarbonate (CTA), PDSEMA, poly(ethylene glycol) methyl ether methacrylate (PEGMA, Mw 475), the alkyl chain derived methacrylate monomer and AIBN were dissolved in THF and degassed by performing three freeze-pump-thaw cycles. The reaction mixture was sealed, transferred to a pre-heated oil bath at 70° C. and stirred for 12 h. The resultant mixture was dissolved in dichloromethane (0.1 mL) and precipitated from hexanes (5 mL). To remove unreacted monomer, the precipitate was further dissolved in dichloromethane (0.1 mL) and precipitated in ether (5 mL). This precipitation procedure was repeated thrice to yield the random copolymer as a pale yellow, waxy substance.

Synthesis of P1:

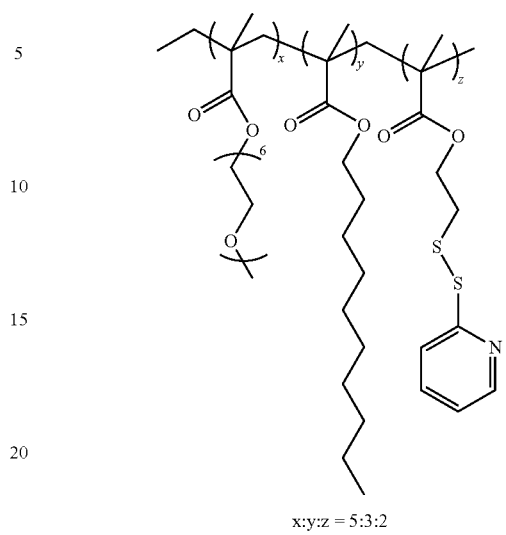

x:y:z = 5:3:2

According to the general procedure for random copolymer synthesis, a mixture of CTA (14.0 mg, 0.04 mmol), PDSEMA (200 mg, 0.78 mmol), PEGMA (930 mg, 1.9 mmol), decylmethacrylate (270 mg, 1.2 mmol) and AIBN (1.3 mg, 7.8 μmol) were polymerized in THF (2.8 mL). GPC (THF) Mn: 49K. PDI: 2.1. $^1$H NMR (400 MHz, CDCl$_3$) δ 8.45, 7.66, 7.10, 4.19, 4.05, 3.88, 3.61, 3.35, 3.04, 2.10-1.60, 1.50-1.20, 1.10-0.70. The molar ratio between the three comonomers was determined by integrating the methoxy proton in the polyethylene glycol unit, the methoxy proton in alkyl derived methacrylate, and the aromatic proton in the pyridine and found to be 5.0:3.3:1.7 (PEO:DecylMA:PDSEMA).

Synthesis of P2:

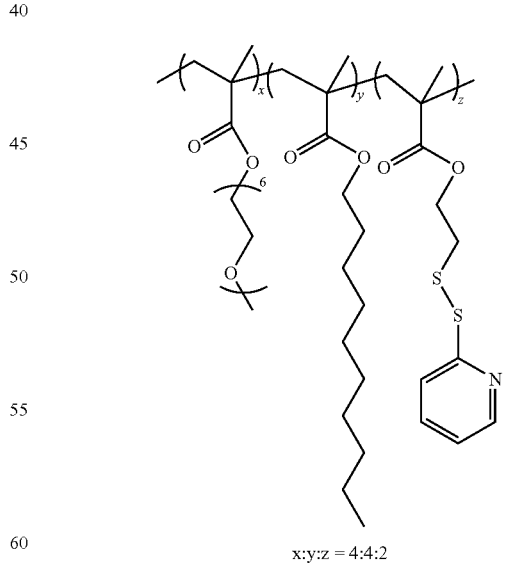

x:y:z = 4:4:2

According to the general procedure for random copolymer synthesis, a mixture of CTA (14.0 mg, 0.04 mmol), PDSEMA (200 mg, 0.78 mmol), PEGMA (740 mg, 1.6 mmol), declmethacrylate (350 mg, 1.6 mmol) and AIBN (1.3 mg, 7.8 μmol) were polymerized in THF (2.6 mL). GPC (THF) Mn: 42K. PDI: 2.0. ¹H NMR (400 MHz, CDCl₃) δ 8.43, 7.65, 7.09, 4.18, 4.04, 3.72, 3.70, 3.33, 3.04, 2.10-1.55, 1.48-1.20, 1.10-0.70. The molar ratio between the three comonomers was determined by integrating the methoxy proton in the polyethylene glycol unit, the methoxy proton in alkyl derived methacrylate, and the aromatic proton in the pyridine and found to be 4.2:4.3:1.5 (PEO:DecylMA:PD-SEMA).

Synthesis of P3:

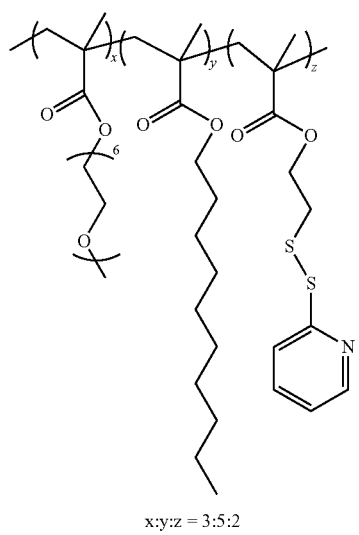

x:y:z = 3:5:2

According to the general procedure for random copolymer synthesis, a mixture of CTA (14.0 mg, 0.04 mmol), PDSEMA (200 mg, 0.78 mmol), PEGMA (560 mg, 1.2 mmol), decylmethacrylate (440 mg, 2.0 mmol) and AIBN (1.3 mg, 7.8 μmol) were polymerized in THF (2.4 mL). GPC (THF) Mn: 52K. PDI: 2.2. ¹H NMR (400 MHz, CDCl₃) δ 8.45, 7.65, 7.09, 4.19, 4.05, 3.88, 3.61, 3.34, 3.00, 2.10-1.50, 1.40-1.20, 1.10-0.80. The molar ratio between the three comonomers was determined by integrating the methoxy proton in the polyethylene glycol unit, the methoxy proton in alkyl derived methacrylate, and the aromatic proton in the pyridine and found to be 3.4:5.0:1.6 (PEO:DecylMA:PD-SEMA).

Synthesis of P4:

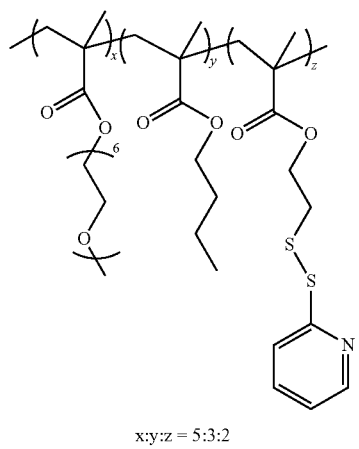

x:y:z = 5:3:2

According to the general procedure for random copolymer synthesis, a mixture of CTA (14.0 mg, 0.04 mmol), PDSEMA (200 mg, 0.78 mmol), PEGMA (930 mg, 1.9 mmol), butylmethacrylate (170 mg, 1.2 mmol) and AIBN (1.3 mg, 7.8 μmol) were polymerized in THF (2.6 mL). GPC (THF) Mn: 55K. PDI: 2.2. ¹H NMR (400 MHz, CDCl₃) δ 8.44, 7.66, 7.10, 4.20, 4.05, 3.89, 3.60, 3.34, 3.00, 2.04-1.80, 1.80-1.22, 1.01-0.78. The molar ratio between the three comonomers was determined by integrating the methoxy proton in the polyethylene glycol unit, the methoxy proton in alkyl derived methacrylate, and the aromatic proton in the pyridine and found to be 5.0:3.3:1.7 (PEO:ButylMA:PD-SEMA).

Synthesis of P5:

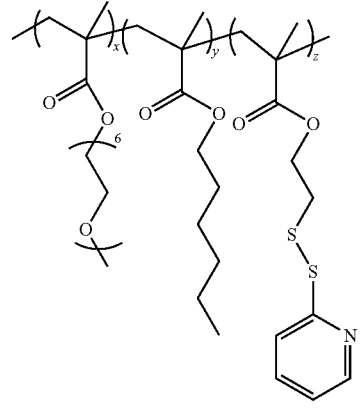

x:y:z = 5:3:2

According to the general procedure random copolymer synthesis, a mixture of CTA (14.0 mg, 0.04 mmol), PDSEMA (200 mg, 0.78 mmol), PEGMA (930 mg, 1.9 mmol), hexylmethacrylate (200 mg, 1.2 mmol) and AIBN (1.3 mg, 7.8 μmol) were polymerized in THF (2.7 mL). GPC (THF) Mn: 38K. PDI: 1.5. ¹H NMR (400 MHz, CDCl₃) δ 8.48, 7.70, 7.13, 4.22, 4.08, 3.91, 3.64, 3.37, 3.04, 2.10-1.60, 1.40-1.20, 1.10-0.78. The molar ratio between the three comonomers was determined by integrating the methoxy proton in the polyethylene glycol unit, the methoxy proton in alkyl derived methacrylate, and the aromatic proton in the pyridine and found to be 4.9:3.3:1.8 (PEO:HexylMA:PD-SEMA).

Synthesis of P6:

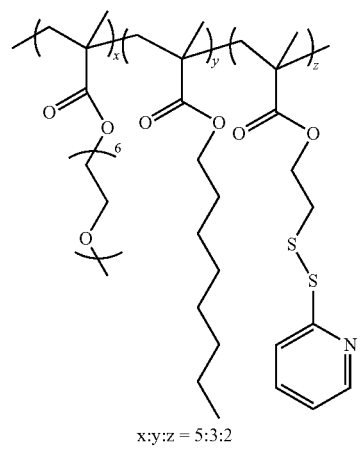

x:y:z = 5:3:2

According to the general procedure for random copolymer synthesis, a mixture of CTA (14.0 mg, 0.04 mmol), PDSEMA (200 mg, 0.78 mmol), PEGMA (930 mg, 1.9 mmol), octylmethacrylate (230 mg, 1.2 mmol) and AIBN (1.3 mg, 7.8 µmol) were polymerized in THF (2.7 mL). GPC (THF) Mn: 41K. PDI: 1.4. $^1$H NMR (400 MHz, CDCl$_3$) δ 8.48, 7.70, 7.13, 4.22, 4.08, 3.91, 3.64, 3.37, 3.04, 2.10-1.60, 1.40-1.20, 1.20-0.78. The molar ratio between the three comonomers was determined by integrating the methoxy proton in the polyethylene glycol unit, the methoxy proton in alkyl derived methacrylate, and the aromatic proton in the pyridine and found to be 5.0:3.4:1.6 (PEO:OctylMA:PDSEMA).

Synthesis of Dye-containing Nanogels

Polymers P1-P6 (2 mg) and DiI, DiO or pyrene (0.02 mg for 1 wt %, 0.04 mg for 2 wt % and 0.2 mg for 10 wt %) were dissolved in acetone and a calculated amount (50 mol % to PDS) of DTT was added. After stirring for 10 min, 1.75 mL of MilliQ water was added and the solution was stirred for 24 hours at room temperature, open to the atmosphere to allow for acetone removal. Unencapsulated DiI/DiO was removed by filtration through a 0.45 µm disposable filter. Remaining solution was washed with 0.25 mL of MilliQ water that was also passed through the filter to dilute the final nanogel solution to 1 mg mL$^{-1}$. Pyridothione and other soluble impurities were removed from the nanogel solution by dialysis against deionized water for 48 hours using a membrane with a MW cutoff of 7,500 g/mol. After dialysis, all samples were transferred to 5 mL glass vials, which were capped, wrapped in foil and stored at 4° C. until mixing experiments were performed. All samples used for these studies were stored for at least one week before mixing studies were performed.

DLS Measurement

Dynamic light scattering experiments were performed using a Malvern Nanozetasizer. The light source used was a 4 mW He—Ne laser operating at 632.8 nm. The nanogels in deionized water (1 mg/mL) were kept at a constant 25° C. throughout the measurement. Dust was eliminated by filtering the solutions through 0.45 µm filters. All the measurements were done at a correlation time of 30 seconds.

Nanogel Encapsulated Dye Mixing

A solution of nanogel encapsulating DiO (100 µL of 1 mg mL$^{-1}$ stock) was diluted with MilliQ water (800 µL) in a 1.5 mL fluorescence cuvette. To this solution, nanogel encapsulating DiI (100 µL of 1 mg mL$^{-1}$ stock) was added. The fluorescence intensities were recorded using an excitation wavelength of 450 nm.

Hofmeister Effect on Size, Morphology and Encapsulation Stability

Figure 16:
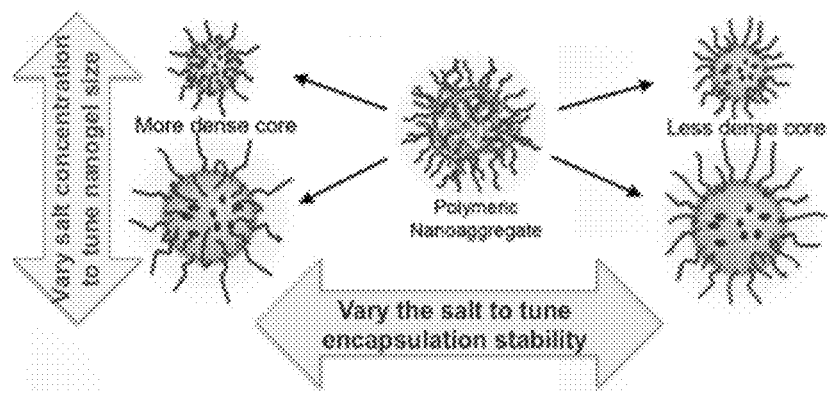
FIG. 16. Schematic illustration of nanogel preparation in the presence of salts.

Although LCST transitions in polymers are often sharp, it is possible that there are also subtle changes in the aggregation states of these polymers at temperatures well below their LCST. Considering that Hofmeister ions could influence LCST, it is also possible that these ions would influence these aggregation states and thus the nanogel itself. It is possible to tune the size and the host-guest properties of polymer nanogels by varying the nature and concentration of the salt ions in the aqueous solution in which they are prepared (FIG. 16).

The self-crosslinked polymer nanogels was used that was derived from an amphiphilic random copolymer. (Ryu, et al. 2010 *J. Am. Chem. Soc.* 132, 17227.) The polymer precursor was based on a hydrophilic oligoethylene glycol functionalized co-monomer and a hydrophobic pyridyl disulfide functionalized co-monomer (Scheme 2).

Scheme 2. Structure of the polymer and the nanogel containing OEG units

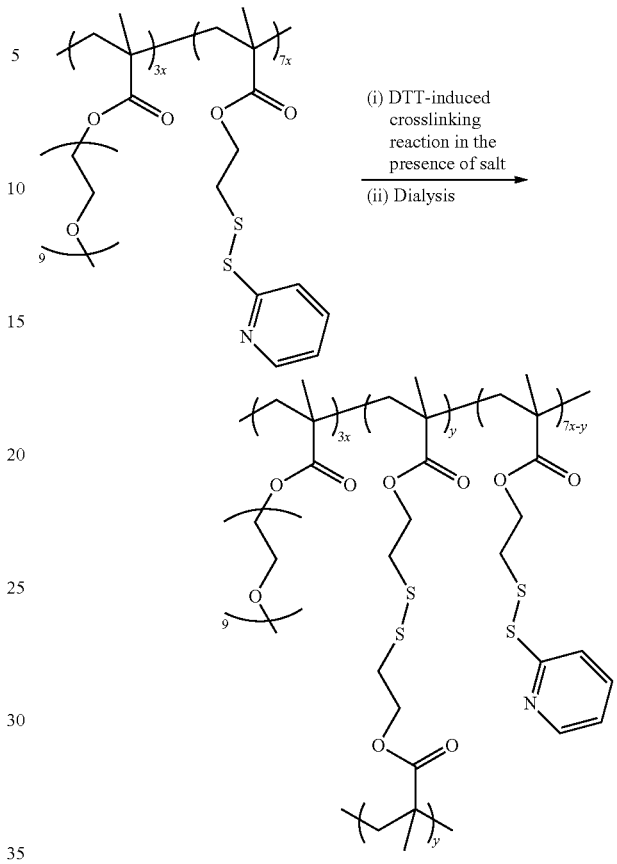

Figure 17:
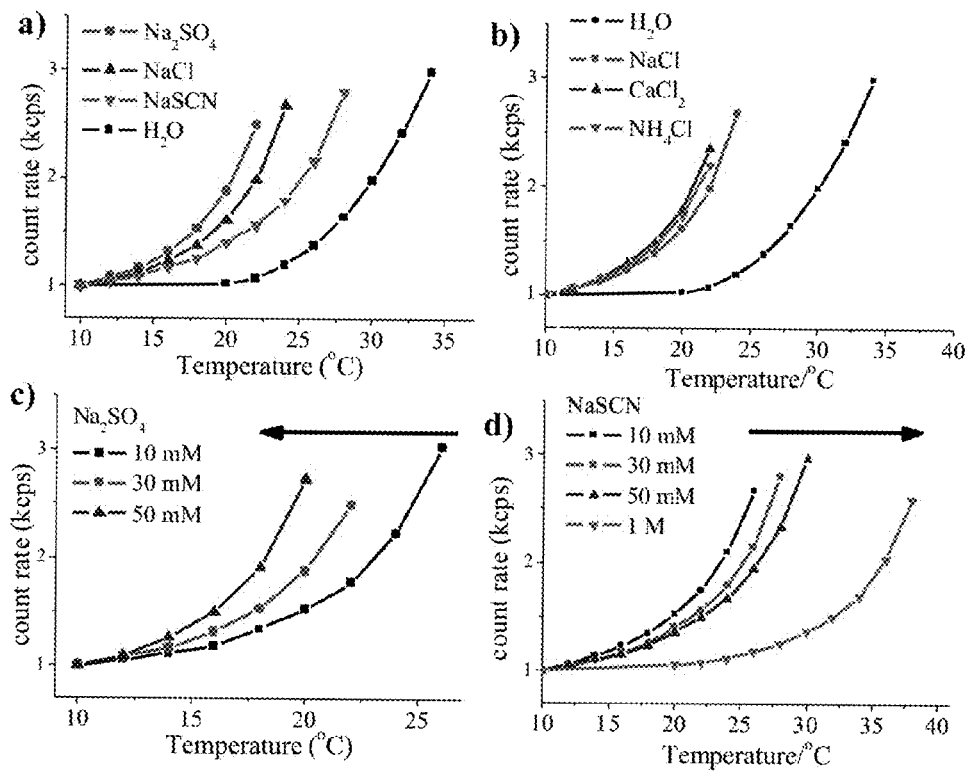
FIG. 17. (a) LCST trend of polymer in salts with different anions solution (salt concentration: 30 mg/mL); (b) LCST trend of polymer in $Na_2SO_4$ solution with different concentrations; (c) LCST trend of polymer in NaSCN solution with different concentrations. (In all cases, the concentration of polymer solution is 10 mg/mL.)

The size of the amphiphilic aggregate is fully retained in the chemically crosslinked nanogel, indicating that there was minimal or no inter-aggregate crosslinking and that the intra-aggregate crosslinking dominated the nanogel formation. To investigate the possibilities, it is essential that these polymers do exhibit an LCST behavior. Oligoethyleneglycol-based polymers and assemblies have been shown to exhibit LCST, because these functionalities can dehydrate at elevated temperatures. (Lutz 2011 *Adv. Mater.* 23, 2237; Lutz, et al. 2006 *J. Am. Chem. Soc.* 128, 13046; Aathimanikandan, et al. 2005 *J. Am. Chem. Soc.* 127, 14922; Qin, et al. 2006 *Adv. Mater.* 18, 2905.) To probe the polymer nanogel precursor, the cloud point of a precursor polymer, containing 30% of the OEG methacrylate and 70% of the PDS-derived methacrylate, was first screened (FIG. 16) in the presence of several salts. DLS at different temperatures was used to assess the onset of cloud point in the aqueous solution. While variation of cations had no effect on the cloud point (FIG. 17b), FIG. 17a shows that the LCST decreases with anion variations and LCST trend follows the Hofmeister series SCN$^-$>Cl$^-$>SO$_4^{2-}$. Note that one would expect the cloud point to increase in NaSCN, since this is a salting-in chaotropic anion. However at low SCN$^-$ concentrations, the cloud point onset decreased, relative to water (FIG. 17a). Nonetheless, there are several indications that this behavior is indeed consistent with the Hofmeister effect on these amphiphilic polymer aggregates: (i) this anomalous behavior has been previously observed with chaotropic anions at low concentrations. (Liu, et al. 2012 *Langmuir* 10, 4867.) To test if our results are consistent with those observations, the cloud point was tested at a much higher salt concentration of 1M NaSCN (FIG. 17d). The polymer did exhibit a much higher cloud point temperature, consistent with the salting-in capability of this anion. (ii) Increase in concentration of the salt ions affords higher cloud points with chaotropic (salting-in) anions and lower cloud point transitions in kosmotropic (salting-out) anions (FIGS. 17c and 17d). (iii) Contrary to the effect of high concentrations of SCN⁻, polymers precipitate out at ambient temperatures in the presence of a high concentration of salting-out anions ($SO_4^{2-}$).

Figure 18:
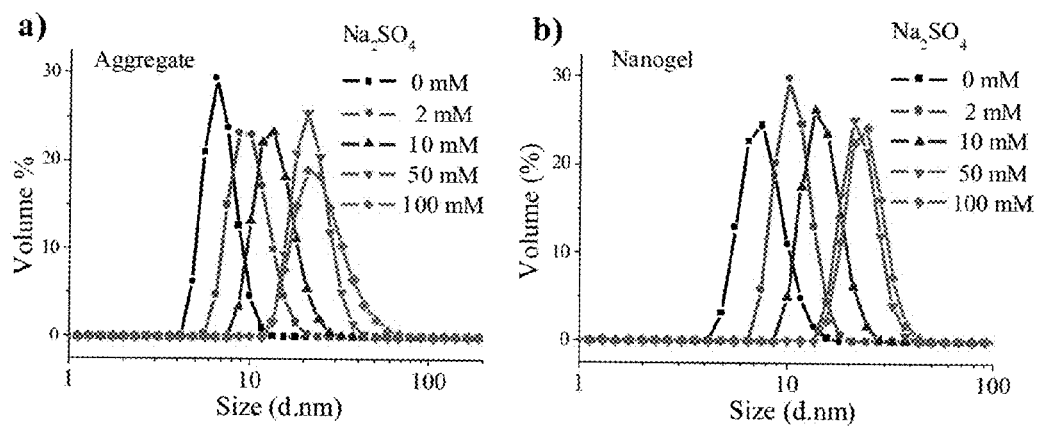
FIG. 18. (a) Size of micelle aggregates in $Na_2SO_4$ solution; (b) Size of nanogels made in $Na_2SO_4$ solution after dialysis.

As shown in FIG. 18 and Table 7, the nanogel sizes can be varied systematically from 8 nm to 24 nm by simply varying the $Na_2SO_4$ concentration. There is a systematic change in the size of the amphiphilic aggregate, which translates to size tunability in the nanogel. At concentrations above 100 mM $Na_2SO_4$, the polymer precipitated out of solution. On the other hand, while the size of the aggregate itself did not change, size of the final nanogel increased with NaSCN concentration. This can be attributed to the possibility that SCN⁻ renders the polymer more soluble, which results in less stable aggregates in solution. This loose aggregation could induce the inter-aggregate cross-linking, resulting in larger size of the nanogel. For example, the nanogel size jumped to about 97 nm, while the polymer aggregate was still only about 11 nm.

TABLE 7

Sizes of the Polymer Aggregates and Nanogels

| Salt | Concentration | Size of micelle aggregates/nm | Size of nanogel/nm |
|---|---|---|---|
| None | 0 mM | 7 | 8 |
| $Na_2SO_4$ | 2 mM | 9 | 10 |
| | 10 mM | 13 | 14 |
| | 50 mM | 22 | 22 |
| | 100 mM | 22 | 24 |
| NaSCN | 2 mM | 11 | 10 |
| | 10 mM | 11 | 13 |
| | 50 mM | 11 | 19 |
| | 100 mM | 10 | 21 |
| | 1M | 11 | 97 |

The guest encapsulation stability of the nanogels formed in the presence of kosmotropic anions ($Na_2SO_4$) should be considerably different from those formed in the presence of chaotropic anions (NaSCN) at similar size and crosslink density. Note that kosmotropic anions would dehydrate the OEG units causing some of these units to behave as if they are hydrophobic. These OEG units would be tucked within the hydrophobic interiors of the nanogels during their synthesis. When these nanogels are redistributed in salt-less water solution, these OEG units are likely to be rehydrated and present themselves on the surface. This structural reorganization is likely to make the nanogel interior more porous, thus making the nanogels leaky. With NaSCN nanogels, on the contrary, the guest encapsulation stability should increase with salt concentration used during the nanogel preparation.

Figure 19:
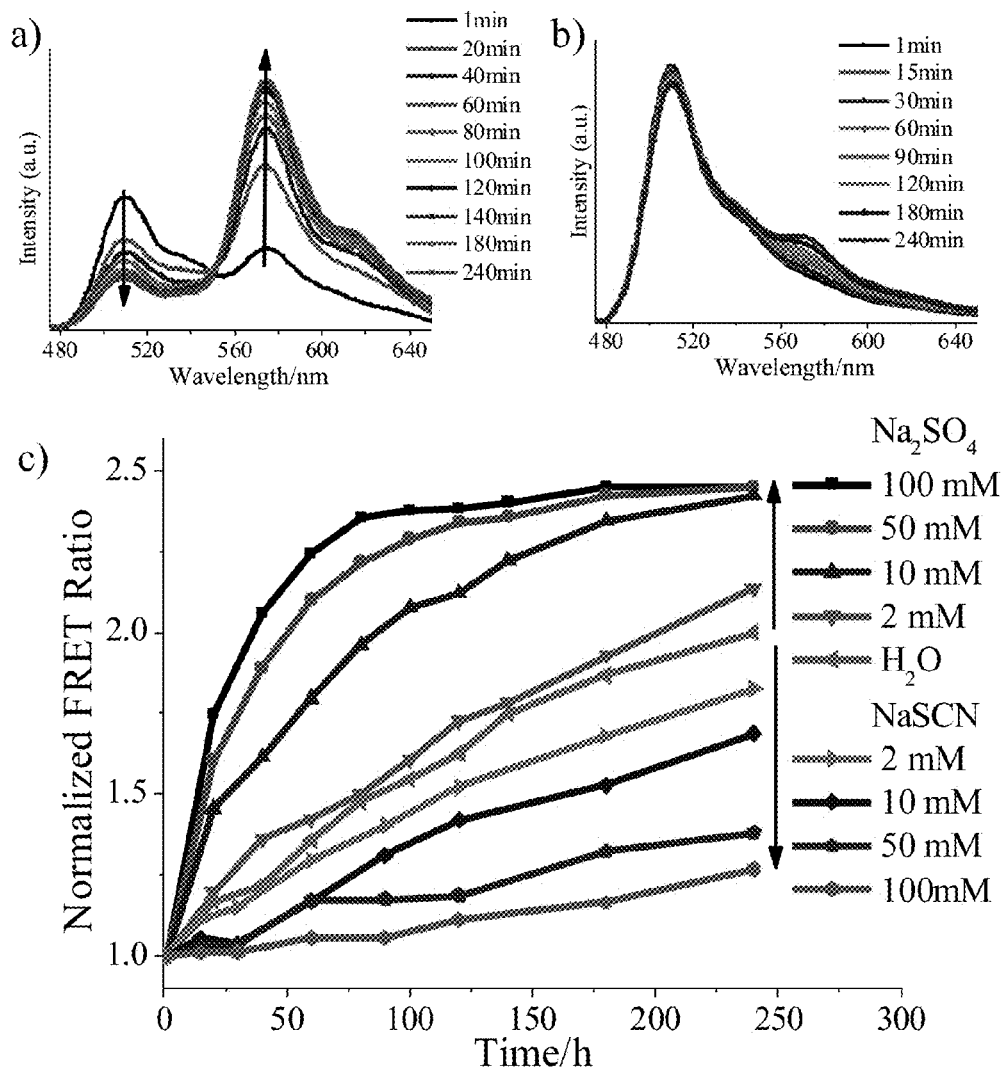
FIG. 19. Fluorescence emission spectra of mixed NGs encapsulated DiI/DiO: (a) NG made in 100 mM $Na_2SO_4$ (aq.); (b) NG made in 100 mM NaSCN(aq.); (c) Comparing the dynamics of leakage/interchange of NGs made in different solution.

The FRET-based method was used to measure the leakage coefficient ($\Lambda$) and gain insights regarding the guest encapsulation stability in these nanogels. (Jiwpanich, et al. 2010 *J. Am. Chem. Soc.* 132, 10683.) For this purpose, nanogels were prepared at identical crosslink densities (6% crosslinked) containing 1 wt % of a FRET donordye (DiO) or a FRET acceptor dye (DiI) as the guest molecule at different salt concentrations. FIG. 19a shows that there is a rapid evolution of FRET with time in the nanogels prepared with $Na_2SO_4$, compared to those prepared without salt. On the other hand, the nanogels prepared with NaSCN exhibited little change in FRET ratio with time and thus very high encapsulation stability (FIG. 19b). The extent of the encapsulation stability can be systematically tuned. For example, the nanogels made from 2 mM and 100 mM $Na_2SO_4$ solution exhibited a $\Lambda$ of 0.0092 min⁻¹ and 0.0393 min⁻¹ respectively, while those from NaSCN solutions exhibited a $\Lambda$ of 0.0034 min⁻¹ to 0.0011 min⁻¹ (FIG. 19c and Table 8).

TABLE 8

Leakage coefficient of nanogels made in different conditions

| | Concentration | $\Lambda$*/min⁻¹ |
|---|---|---|
| Pure water | 0 mM | 0.0057 |
| $Na_2SO_4$ | 2 mM | 0.0092 |
| | 10 mM | 0.0129 |
| | 50 mM | 0.0227 |
| | 100 mM | 0.0393 |
| NaSCN | 2 mM | 0.0034 |
| | 10 mM | 0.003 |
| | 50 mM | 0.0016 |
| | 100 mM | 0.0011 |

*$\Lambda$ is the leakage coefficient.

Figure 20:
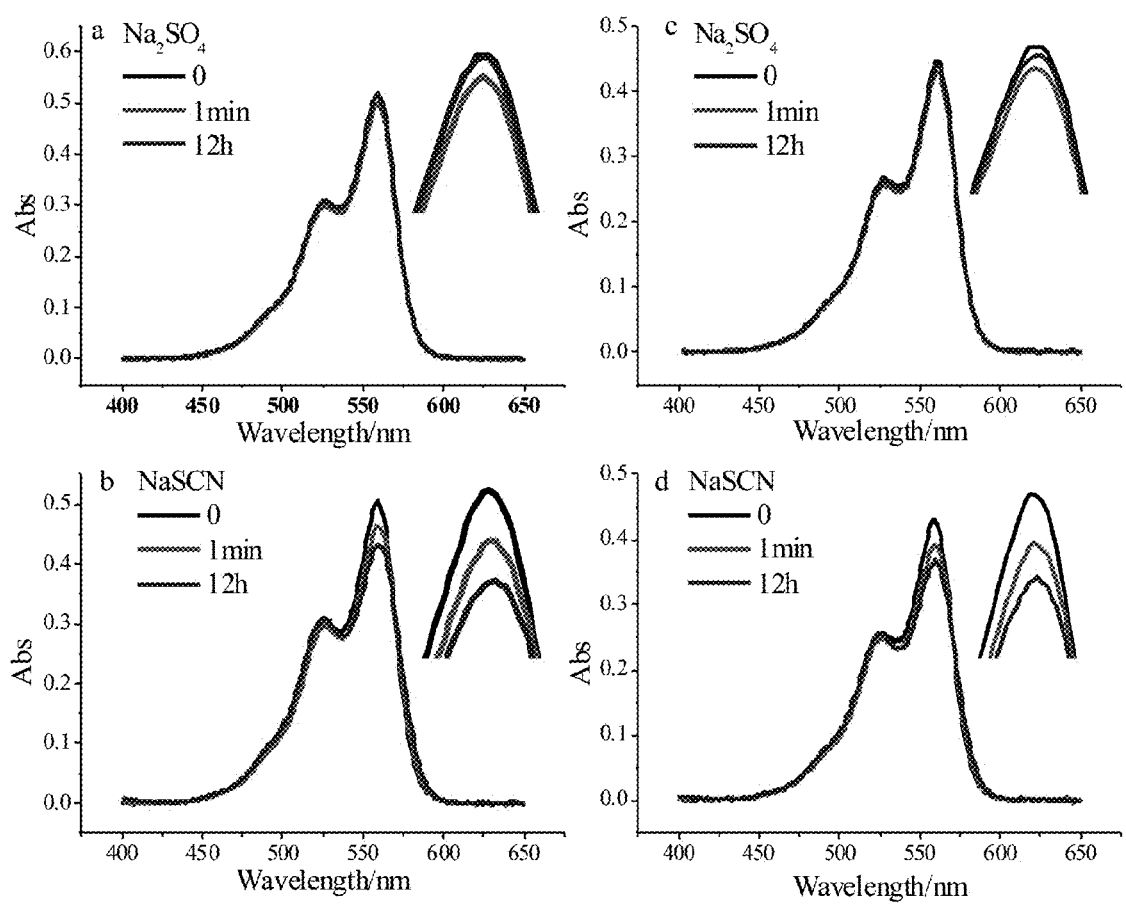
FIG. 20. Absorbance of nanogel loaded with DiI after addition of $Na_2SO_4$ or NaSCN. Nanogel was made in salt free water, and concentration of both the measured nanogel solutions is 0.2 mg/mL. (a-b) Nanogels with 6% crosslinking degree, (c-d) Nanogels with 13% crosslinking degree.
Figure 27:
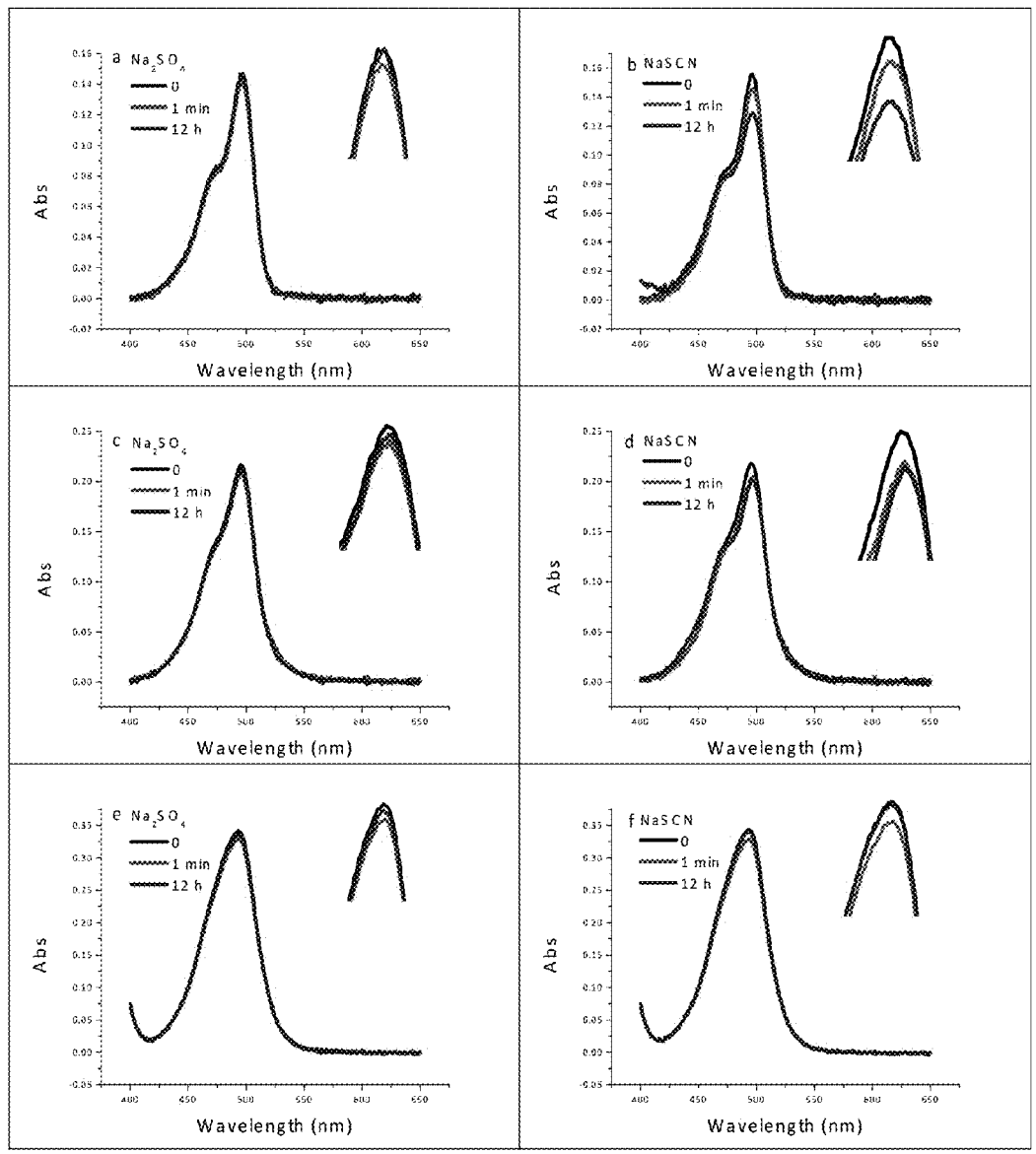
FIG. 27. Absorbance of the nanogel loaded with DiI after the addition of $Na_2SO_4$ or NaSCN. Nanogel was made in salt free water, and the concentration of both measured nanogel solutions is 0.2 mg/mL. (a-b) Nanogels with 6% crosslinking degree; (c-d) Nanogels with 13% crosslinking degree; (e-f) Nanogels with 25% crosslinking degree.

To further test this, the nanogels with three different crosslink densities (6%, 13%, and 25%) were prepared in salt-free water. Their encapsulation stability was tested directly by monitoring the absorption spectrum of the guest molecule, DiI. The leakage and precipitation of the dye molecule were measured, instead of the dynamic exchange of the dye molecule. Since the nanogel is already prepared in salt-free water, the leakage trend should be opposite to that shown in FIG. 19. That is, here, the solution that contains $Na_2SO_4$ should dehydrate the exposed OEG groups, thus rendering the nanogel less leaky. On the contrary, NaSCN should render the nanogels more leaky, because more OEG units will be hydrated ane become more exposed to the solvent, thereby leaving the core of the nanogel less dense. FIG. 20 shows that this is indeed the case. In all three nanogels, there is no leakage of the dye molecules in the presence of $Na_2SO_4$. However, the 6% and 13% crosslinked nanogels were leaky in the presence of NaSCN, while the 25% crosslinked one encapsulates the guest molecule sufficiently tightly that it was unperturbed by the presence of the SCN⁻ anions (FIG. 27). Similar trend was observed for the nanogels with DiO as the guest molecule (FIG. 27).

Figure 21:
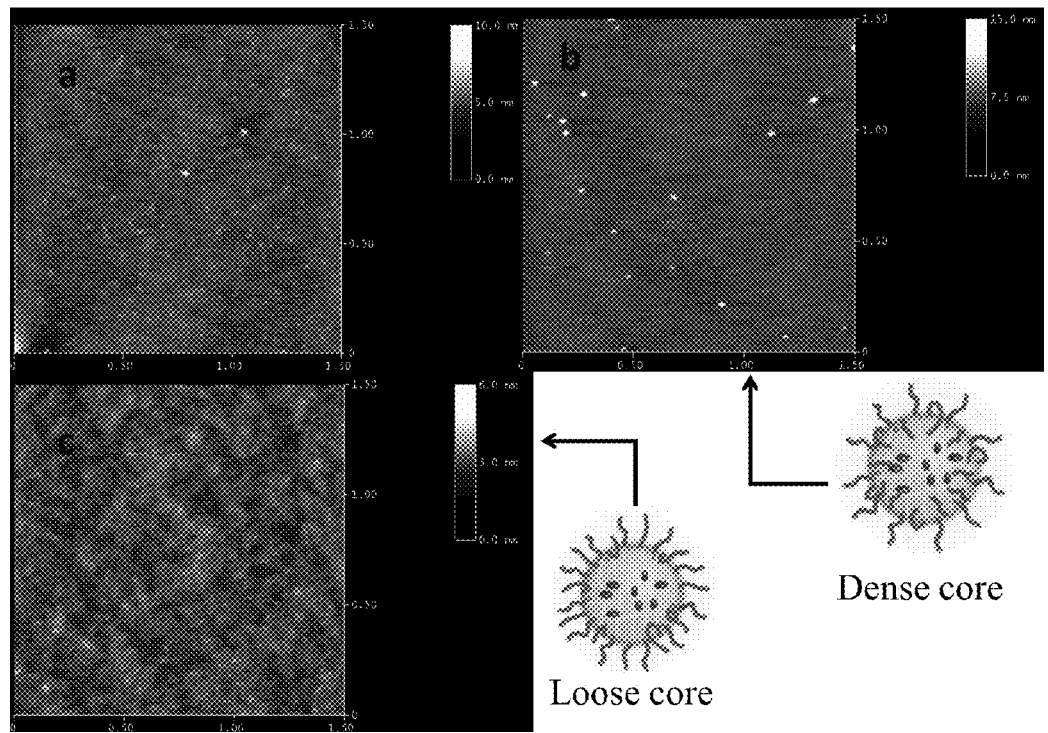
FIG. 21. Change in morphology of the nanogels due to the presence of salts: (a) nanogel without salts (b); nanogel after adding $Na_2SO_4$; (c) nanogel after adding NaSCN.

The above results may be rationalized based on the salt-dependent dehydration or rehydration of the OEG units. NaSCN would rehydrate the OEG units and thus render any buried OEG units to be presented at the surface. This rehydration should leave behind a relatively hollow interior. To further test this possibility, the nanogels were investigated using atomic force microscope (AFM). AFM images show the change in morphology of the nanogels due to the presence of salts (FIG. 21). The presence of SCN⁻ ions causes the nanogels to collapse on the surface, which is consistent with its less dense core structure. However, since $SO_4^{2-}$ ions render the core denser, the nanogels seem to retain their shape upon interaction with the surface.

Figure 22:
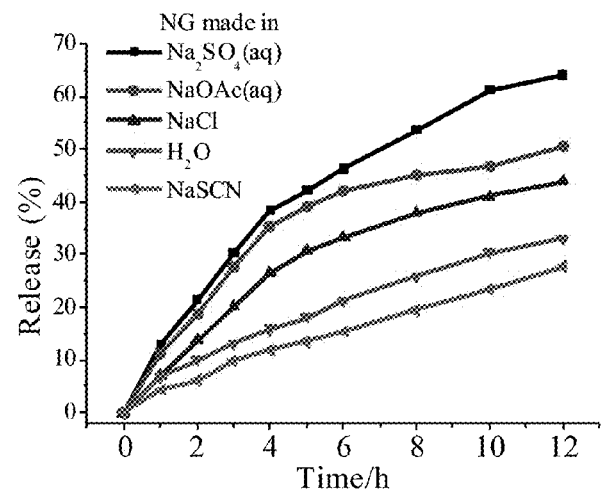
FIG. 22. GSH-induced (10 mM) dye release rate from the nanogels made in different salt solutions.
Figure 23:
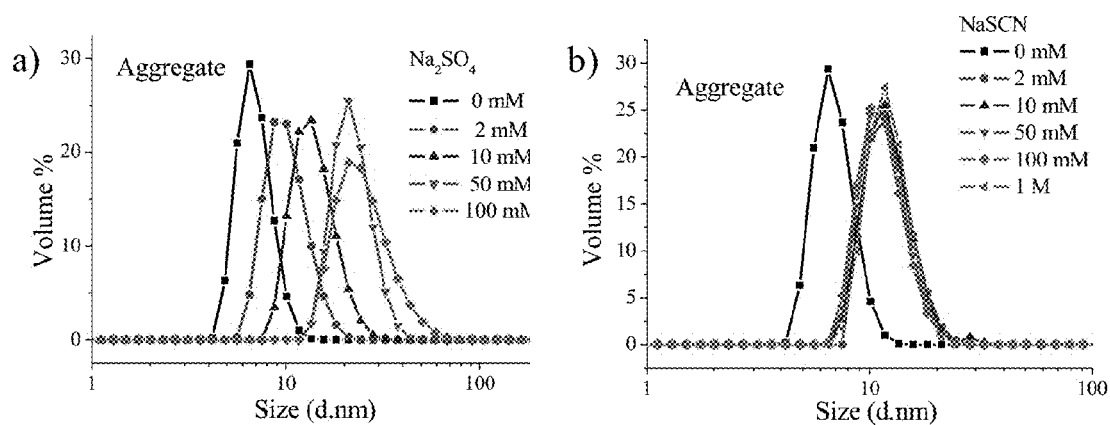
FIG. 23. DLS of polymer micelle aggregates in water and salt solution: (a) Polymer in different concentration of $Na_2SO_4$; (b) Polymer in different concentrations of NaSCN. (In all cases, the concentration of polymer was 10 mg/mL.)
Figure 24:
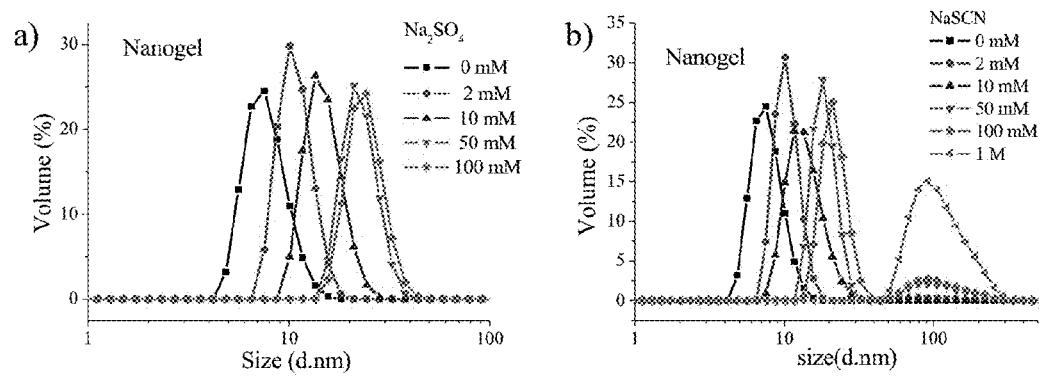
FIG. 24. DLS of nanogel samples after dialysis in water (1 mg/mL): (a) Nanogel made in different concentrations of $Na_2SO_4$ solution; (b) Nanogel made in different concentrations of NaSCN solution.
Figure 25:
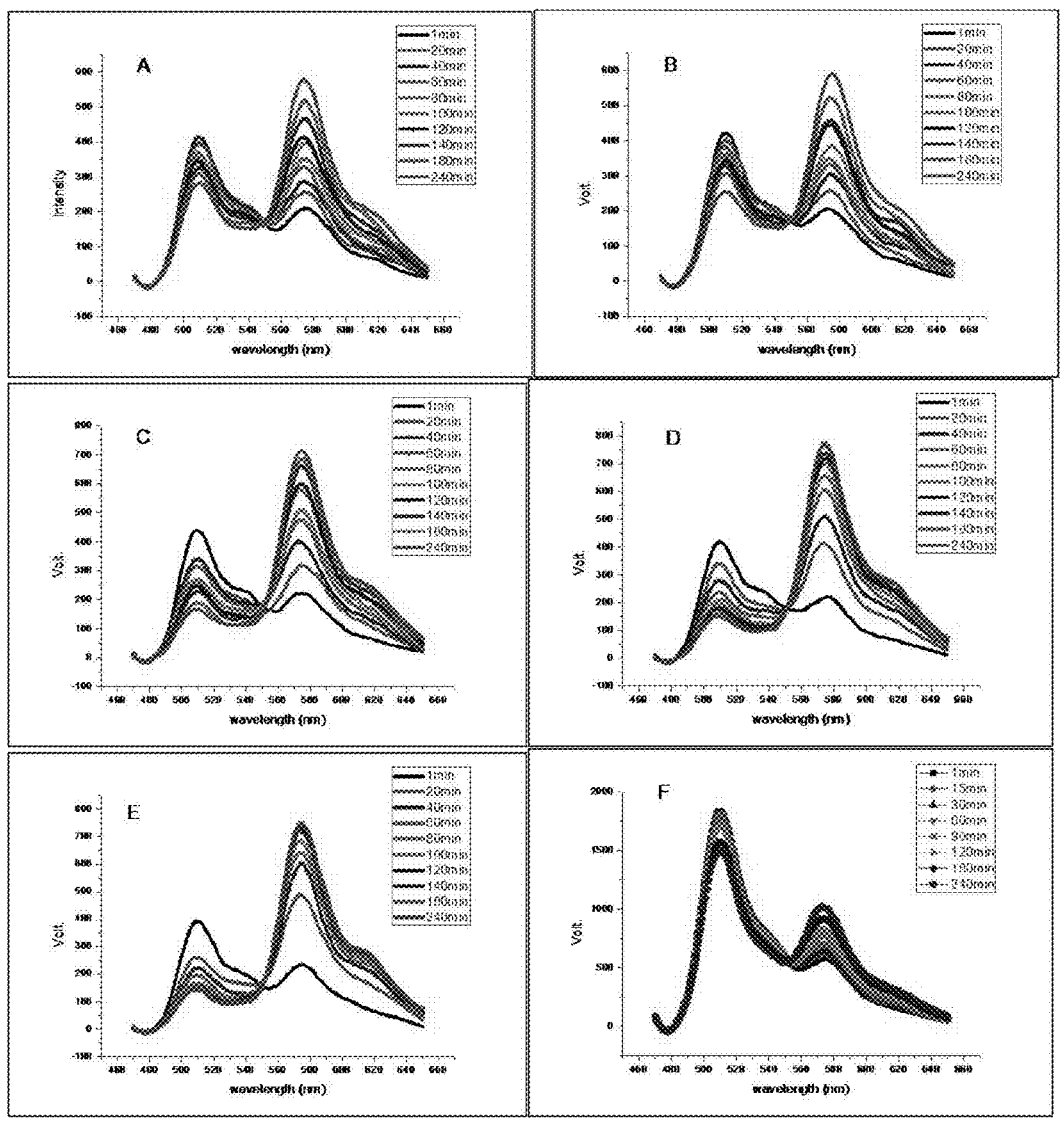
FIG. 25. Emission spectra of dye exchange between DiI nanogel and DiO nanogel (6% cross-linking degree) made in different conditions: (A) nanogel made in salt free water; (B)-(E) nanogels made in different concentrations of $Na_2SO_4$ solution, 2 mM, 10 mM, 50 mM and 100 mM, respectively; (F)-(I) nanogels made in different concentrations of NaSCN solution, 2 mM, 10 mM, 50 mM, 100 mM, respectively.
Figure 25:
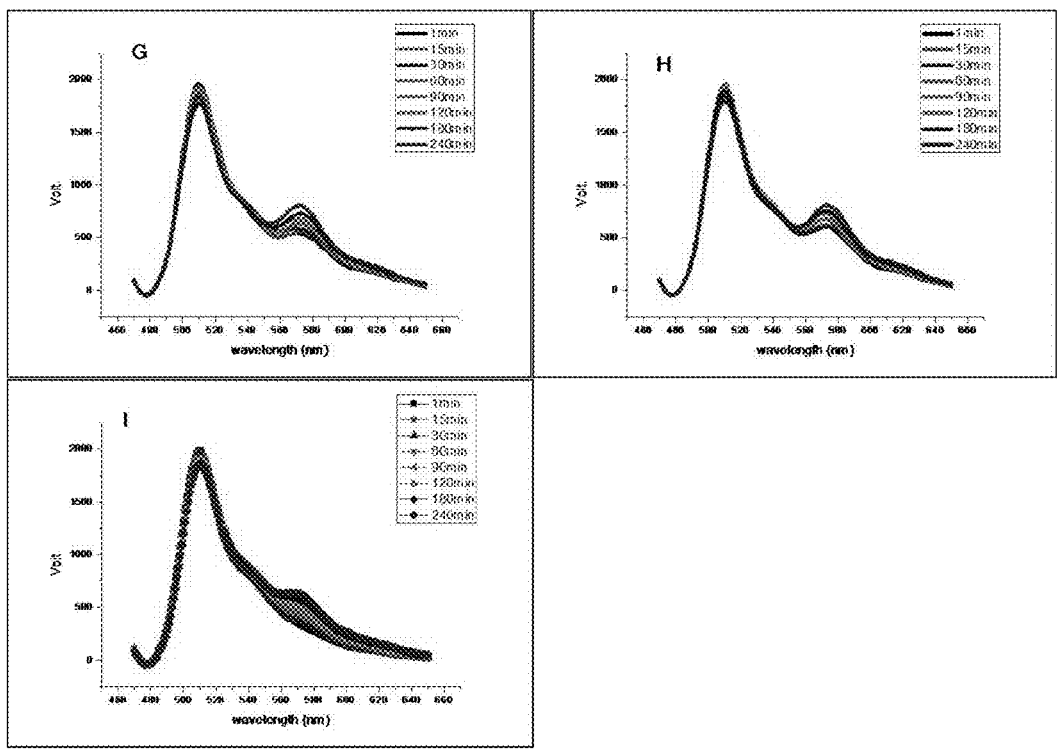
Figure 26:
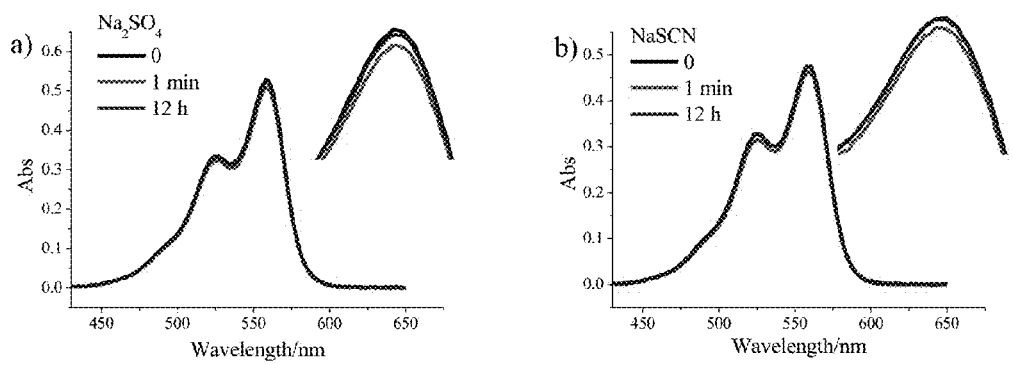
FIG. 26. Absorbance of the nanogel loaded with DiI after addition of $Na_2SO_4$ or NaSCN. Nanogel was made in salt free water, and the concentration of both measured nanogel solutions is 0.2 mg/mL. (a-b) Nanogels with 25% crosslinking degree.

The relative release rate of the guest molecules from nanogels prepared was tested under different salt conditions in the presence of a stimulus. Note that the disulfide crosslinked nature of these nanogels makes them susceptible to uncrosslink in the presence of glutathione (GSH). Accordingly, nanogels prepared from an aqueous solution containing 30 mM concentrations $Na_2SO_4$, NaOAc, NaCl, and NaSCN were tested. All these nanogels were prepared at 25% crosslink density to insure significant guest encapsulation stability in the absence of GSH. When these nanogels were subjected to 10 mM GSH concentration, the release rates observed were indeed consistent with the Hofmeister series. The guest molecule leakage was lower only in NaSCN, compared to water, and it followed the order: $Na_2SO_4$>NaOAc>NaCl>No salt>NaSCN, as shown in FIG. 22.

Thus, it has been demonstrated that: (i) there are subtle differences in the aggregation states of OEG-functionalized amphiphilic polymer in aqueous phase, endowed by the presence of various salts; (ii) while anions provide variations as predicted by the Hofmeister effect, variation in cations does not affect the aggregation of the polymer; (iii) in the case of kosmotropic $SO_4^{2-}$, the size of the nanogel can be systematically varied with concentration, since the size is determined by the aggregate size; (iv) in the case of chaotropic anion $SCN^-$, inter-aggregate crosslinking occurs due to the rather loose nature of the aggregates; (v) encapsulation stability of guest molecules is dependent on the nature of the salt used for the preparation of the nanogels; chaotropic anions afford nanogels with greater guest encapsulation stability; (vi) salt-dependent hydration of the OEG units in the nanogel causes variations in its density, which then determines the leaky character of the nanogel. From a practical perspective, utilizing Hofmeister ions provides unprecedented control in fine-tuning the size of the polymer nanogel. In addition to size, one has a concurrent control over altering the guest encapsulation stabilities.

Experimental 2,2'-Dithiodipyridine, 2-mercaptoethanol, polyethylene glycol monomethylether methacrylate (MW 450), D,L-dithiothreitol (DTT), 1,1'-dioctadecyl-3,3,3',3'-tetramethylindocarbocyanine perchlorate (DiI) and 3,3'-dioctadecyloxacarbocyanine perchlorate (DiO), 4-Cyano-4-(phenylcarbonothioylthio)pentanoic acid and other conventional reagents were obtained from commercial sources and were used as received, unless otherwise mentioned. Polymer was synthesized using RAFT polymerization and then purified by precipitation. Pyridyl disulfide ethyl methacrylate (PDSEMA) was prepared using a previously reported procedure. (Ghosh, et al. 2006 *Macromolecules* 39, 5595-5597.) $^1$H-NMR spectra were recorded on a 400 MHz Bruker NMR spectrometer using the residual proton resonance of the solvent as the internal standard. Chemical shifts are reported in parts per million (ppm). Molecular weights of the polymers were estimated by gel permeation chromatography (GPC) using PMMA standard with a refractive index detector. Dynamic light scattering (DLS) measurements were performed using a Malvern Nanozetasizer. UV-visible absorption spectra were recorded on a Varian (model EL 01125047) spectrophotometer. The fluorescence spectra were obtained from a JASCO FP-6500 spectrofluorimeter. Transmission electron microscopy (TEM) images were taken using a JEOL 100CX at 100 KV. AFM images were collected on a Digital Instruments Nanoscope III in tapping mode under ambient conditions using silicon cantilievers (spring constant 0.58 N/m).

Synthesis of Random Copolymer

A mixture of 4-Cyano-4-(phenylcarbonothioylthio)pentanoic acid (3 mg, 0.02 mmol), PDSEMA (1.25 g, 4.9 mmol), polyethylene glycol monomethyl ether methacrylate (1 g, 2.1 mmol) and AIBN (2.5 mg, 0.014 mmol) was dissolved in THF (5 mL) and degassed by performing three freeze-pump-thaw cycles. The reaction mixture was sealed and then transferred into a pre-heated oil bath at 65° C. for 10 h. To remove unreactive monomers, the resultant mixture was precipitated in cold ethyl ether (20 mL) to yield the random copolymer as a waxy liquid. GPC (THF) Mn: 13 K. PDI: 1.3. $^1$H NMR (400 MHz, $CDCl_3$) δ: 8.46, 7.68, 7.11, 4.35-4.09, 3.94-3.37, 3.03, 2.04-1.64, 1.43-0.87. The molar ratio between two blocks was determined by integrating the methoxy proton in the polyethyleneglycol unit and the aromatic proton in the pyridine and found to be 3:7 (PEO: PDSEMA).

Synthesis of Nanogels Having DiI/DiO

The polymer (10 mg) was dissolved in 1 mL water or salt solution. And 0.02 mL DiI stock solution (5 mg/mL) or 0.04 mL DiO stock solution (2.5 mg/mL) was added into the polymer solution. The mixed solution was stirred overnight at room temperature, open to the atmosphere allowing the organic solvent to evaporate. Then a measured amount of DTT (0.4 μmol, 0.8 μmol and 2.0 μmol for 10 mol %, 20 mol % and 50 mol % against PDS groups, respectively) was added. After stirring for 4 h, insoluble DiI/DiO was removed by filtration and pyridothione was removed from the nanogel solution by extensive dialysis using a membrane with a molecular weight cutoff of 7,000 g/mol.

DLS Measurement

Dynamic light scattering experiments were performed by using a digital correlator and goniometer. The light source was solid-stat laser system, operating at 514 nm. For LCST measurement, temperature trend measurements were done and the temperature was increased from 10 C to 60° C. by 2° C. Equilibration time at each temperature is also defined as 10 min; scattering intensity was monitored as a function of temperature. The polymer in water or salt solution (10 mg/mL) was used. For size measurement, the nanogels in deionized water (1 mg/mL) was kept constant at 25° C. throughout the experiment. Dust was eliminated by filtering the solution through 0.45 μm filter. All measurements were done at a correlation time of 30 seconds.

Absorption Spectra Measurement

The nanogels (6% cross-linking degree) made in salt free water (0.2 mg/mL) were used as stock solution. First, 1 mL sample was used for measurement. Then 0.03 mL salt stock solution (1M) was added into the sample and absorbance intensity was measured again. About 12 h later, one more measurement was taken for each sample.

Nanogel Encapsulated Dye Mixing

A solution of nanogel containing DiI (100 μL) was mixed with a solution of nanogel containing DiO (100 μL) in a cuvette, and then milliQ water (800 μL) was added to adjust the volume. The fluorescence intensity was recorded at 450 nm excitation wavelength.

Feedback Responsive Nanogels for Controlled Drug Release

Novel $pH/CO_2$ responsive nanogels were synthesized from random copolymers of pentafluorophenyl acrylate and poly(ethylene glycol) methyl acrylate for controlled drug delivery. The polymers used for nanogel synthesis were prepared by RAFT mediated polymerization method. The polymers were cross-linked a with bis-amino acetal cross-linker, which is known to hydrolyse readily at acidity levels just below physiological pH. (Jain, et al. 2007 *J. Macromolecules* 40, 452-457.) After cross-linking, the nanogel was modified with octylamine, which reacted with the remaining pentafluorophenyl acrylate to produce an amide bond. The resultant amide bond is relatively stable at neutral, alkali and acidic pH values, but the cross-linker degrades promptly under acidic conditions. The modified nanogel was expected to be relatively inert at physiological pH values and to possess high drug loading efficiency owing to the presence of octyl group due its hydrophobic nature.

Synthesis and Stability of Nanogels

Figure 28:
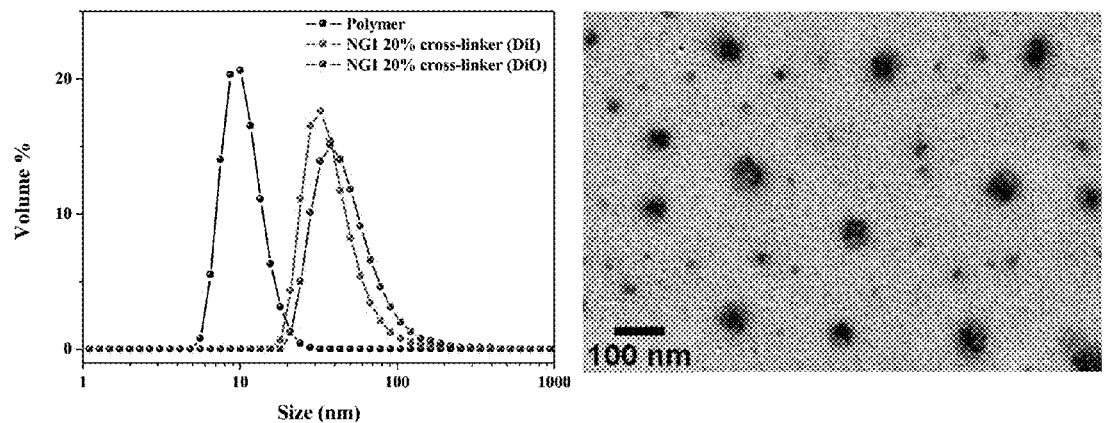
FIG. 28. DLS and TEM of NG1.

The random copolymer for the nanogel (NG) preparation was synthesized by RAFT polymerization of Poly(ethyleneglycol) methyl acrylate (PEGMA$_{950}$) and Pentafluorophenyl acrylate (PFPA) using AIBN as the initiator at 75° C. (Zhuang, et al. 2012 ACS Macro Lett. 1, 175-179.) The polymer was characterized by NMR spectroscopy and molecular weight determined by GPC was 24,500. The nanogels were prepared at room temperature by treating polymer solution with desired amount of acetal crosslinker (Scheme 3) which was synthesized by the reported procedure. (Jain, et al. 2007 J. Macromolecules 40, 452-457.) The pentafluorophenyl acrylate ester in the random copolymer easily reacts with the amino groups in the pH/CO$_2$ responsive acetal crosslinker to yield the nanogel. The cross-linking reaction was monitored by $^{19}$F NMR as well as FTIR. The remaining pentafluorophenyl groups were substituted using octylamine. The nanogels were purified by repeated dialysis against pH 7.8 distilled water using a membrane with a molecular weight cut-off of 7,500 g/mol. The nanogels were characterized by transmission electron microscopy (TEM) and dynamic light scattering (DLS). The DLS study revealed that the nanogels are ~65-85 nm in size and TEM studies showed the presence of spherical structures with ~85 nm in size (FIG. 28).

Scheme 4. Synthesis of cross-linked polymer nanogels (NG1-NG3) from precursor polymer PEGMA-r-PFPA

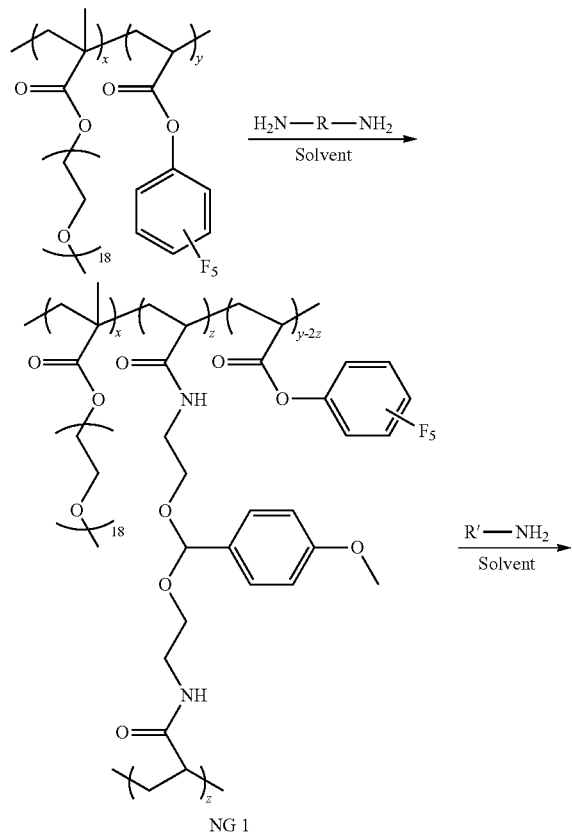

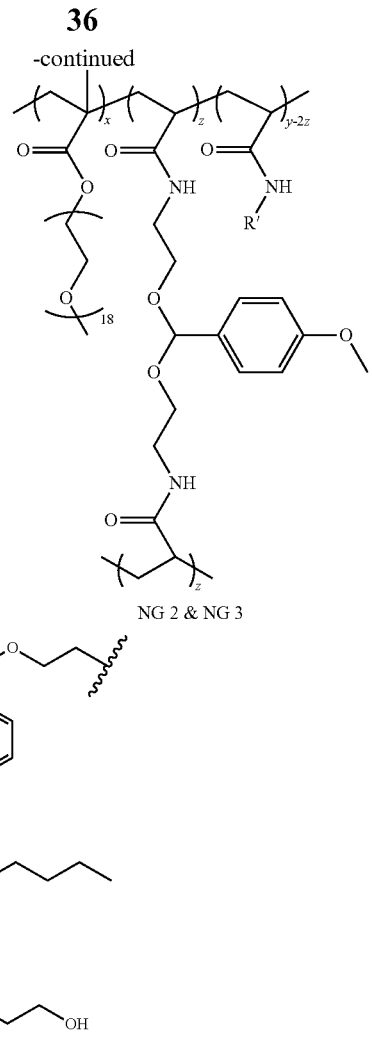

For drug delivery applications it is crucial that a nanogel be capable of containing its payload while it the blood stream until it encounters the desired biological trigger. The stability and pH/CO$_2$ responsiveness nature of our nanogels was studied using FRET. A FRET pair utilizing 3,3'-dioctadecyloxacarbocyanine perchlorate (DiO) as the donor and 1,1'-dioctadecyl-3,3,3',3'-tetramethylindocarbocyanine perchlorate (DiI) as the acceptor were chosen. Nanogels were prepared loaded with either DiI or DiO. Upon mixing, if both the nanogels are stable, excitation of DiO at 450 nm will result in emission of DiO at 505 because the distance between the dye molecules are larger than that of the Forster radius. However, if the nanogels are leaky or when they respond to pH/CO$_2$ dyes will be able to mix, so that DiO migrates into a DiI nanogel and vice versa. This mixing places the dyes close enough to one another for FRET to occur. Under these conditions, excitation of DiO results in emission from both DiO and DiI.

Figure 29:
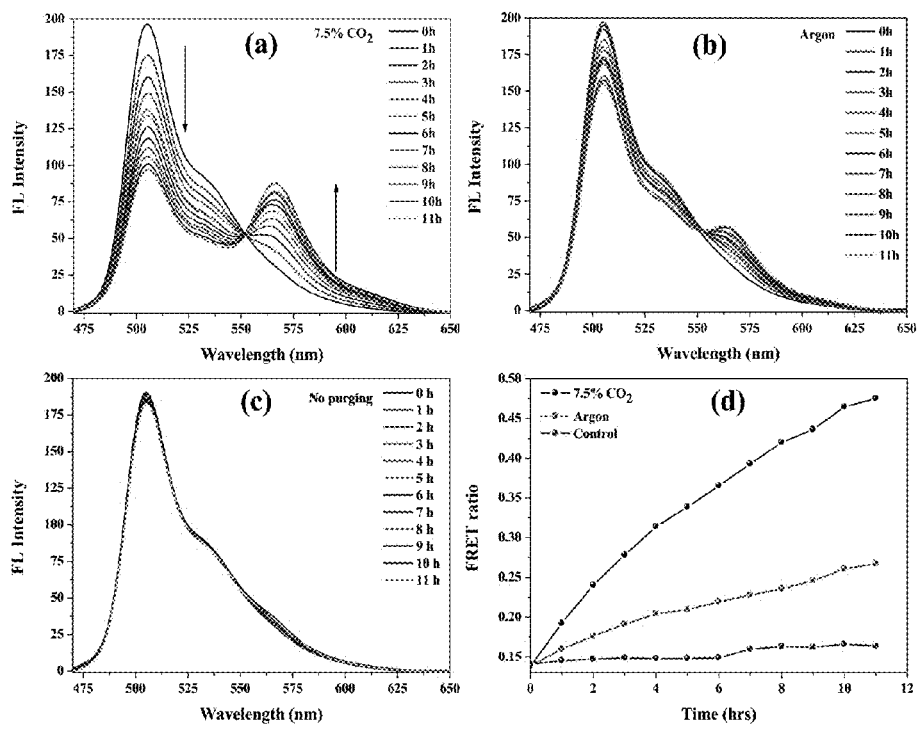
FIG. 29. Fluorescence spectra of mixed solutions of NG1 prepared with 1 wt % DiO/DiI tracing the development of FRET over time.

Aqueous solutions of nanogels (20% cross-linked, pH 7.8) loaded with 1 wt % DiO or DiI were prepared. 100 µL of 0.2 mg/mL nanogel solutions containing different dyes were mixed together followed by the addition of 800 µL of PBS 7.8 buffer so that total volume was maintained as 1 mL. (Satav, et al. 2010 Biomacromolecules 11, 1735-1740.) This nanogel mixture was then kept in a water bath at 37° C. while purging with air containing 7.5% CO$_2$ at a bubble rate of 12 bubbles per minute. Controls experiments were conducted while purging with Argon and with no purging at all. The time dependent FRET evolution, as observed in the fluorescence spectra of these mixed nanogel solutions are plotted in FIG. 29. The nanogel solutions purged with $CO_2$ and argon showed FRET evolution. However, the solution purged with $CO_2$ exhibits much faster rates of FRET development. As the purging continues, a decrease in the fluorescence intensity at 505 nm and an increase at 565 nm was observed over time, which indicated that the dye molecules were slowly released from the nanogel. This clear change in the fluorescence spectra demonstrates that the crosslinker breaks down due to pH/$CO_2$ responsive nature. However the control experiment showed almost no FRET evolution over time indicating that the nanogels are highly stable. This effect is quite favorable in that the ratio of the two intensities can be measured and related to pH/$CO_2$ responsive nature of the nanogels. The FRET ratio was plotted against time is shown in FIG. 29d. The FRET ratios for the nanogels purged with $CO_2$ are much higher than that of the control experiment.

Figure 30:
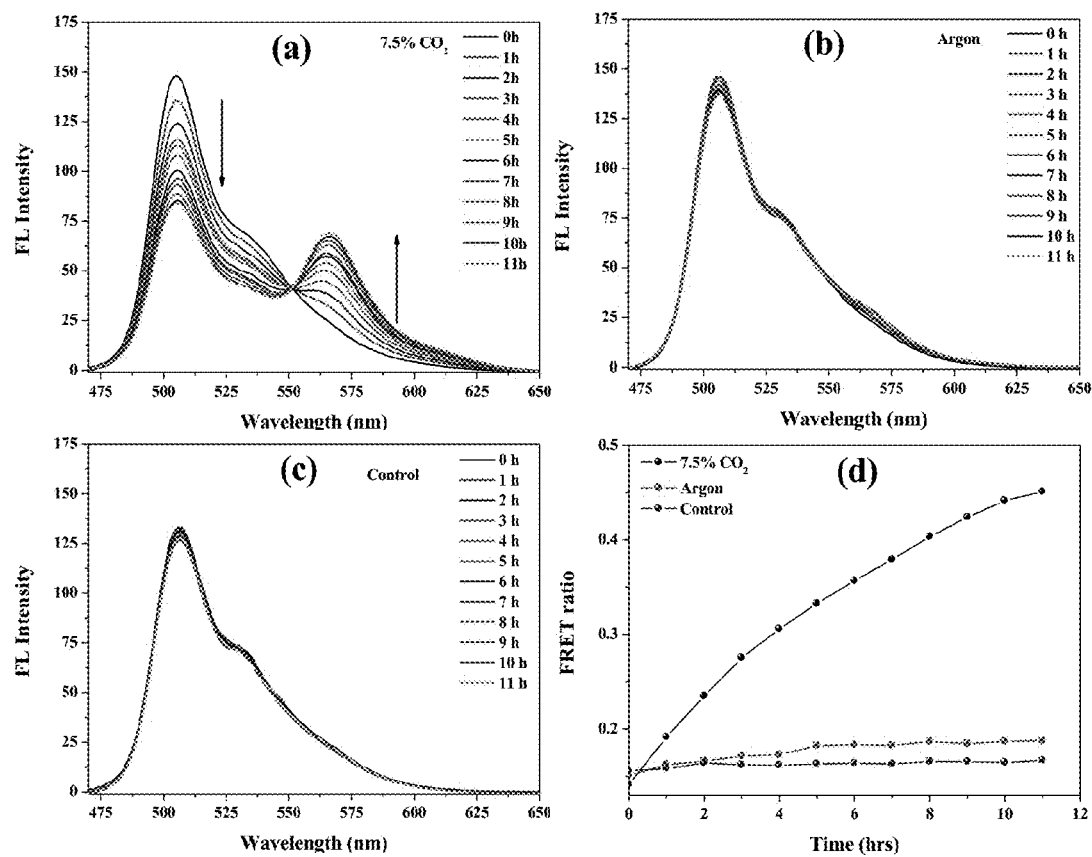
FIG. 30. Fluorescence spectra of mixed solutions of NG1 prepared with 0.75 wt % DiO/DiI tracing the development of FRET over time.

To test if the FRET evolution from the nanogel solution purged with argon was due to excess dye loading, nanogels with 20% cross-linking density were prepared and loaded with 0.75 wt % dye instead of 1 wt % used previously. FRET experiment showed significant reduction of FRET evolution when purged with argon (FIG. 30).

Figure 31:
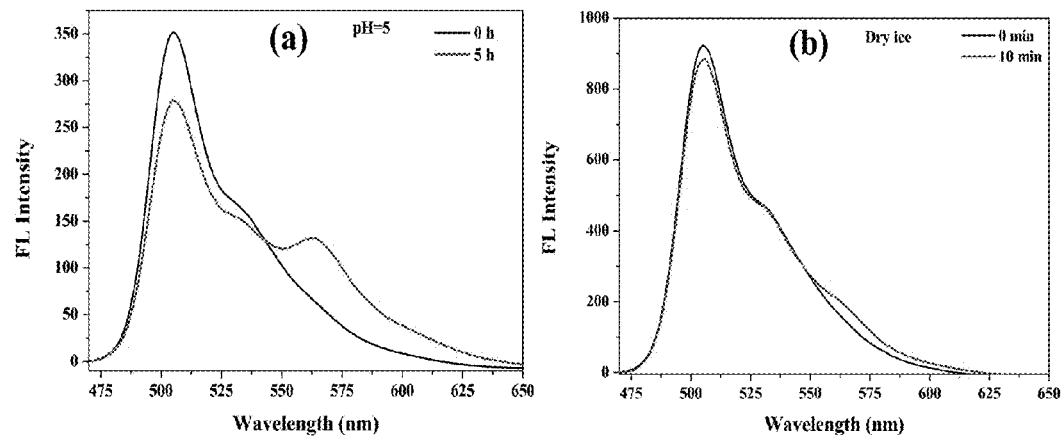
FIG. 31. Fluorescence spectra of the mixed solutions of NG1 prepared with 0.75 wt % DiO/DiI: (a) at pH=5; (b) dry ice.

To further confirm the pH/$CO_2$ responsive nature of the nanogels, two methods were used. First, the mixed nanogels solutions were placed in a pH=5.0 solution for 5 h (FIG. 31a). In another method the mixed nanogel solutions treated with dry ice for 10 minutes (FIG. 31b). As expected, the nanogels were found to be unstable and degrade under acidic conditions that degraded at lower pH. Fluorescence studies showed the FRET evolution indicating the dissociation of acetal crosslinker. The changes in the intensities of DiO and DiI emission again proved the pH/$CO_2$ responsive nature of the nanogels. The nanogels were found to be very stable under neutral and alkaline pH.

Cross-linking Density, Stability and Hydrophobicity

Figure 39:
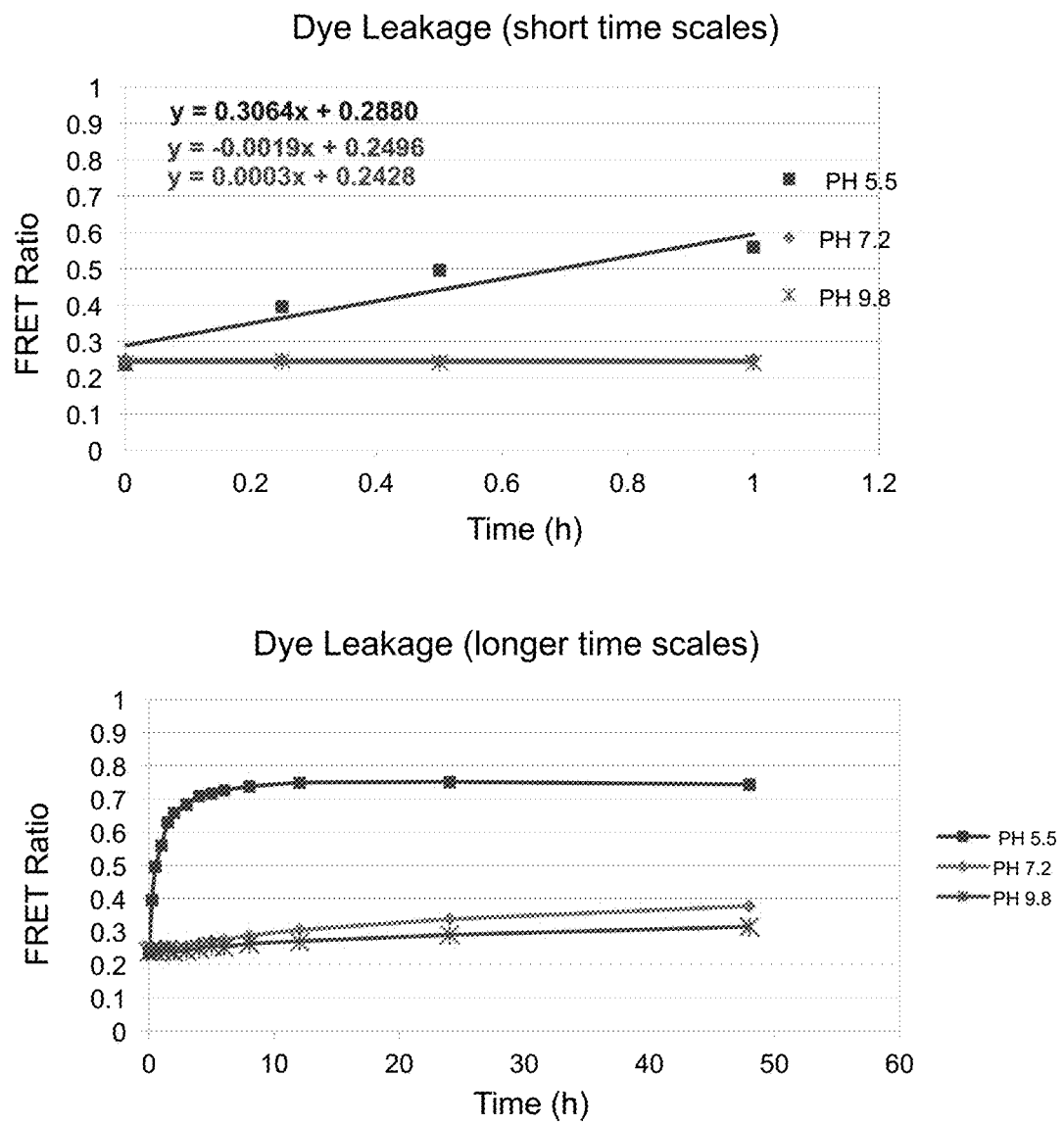
FIG. 39. Data showing a clear leakage of the guest molecules dependent on the pH of the solution.
Figure 40:
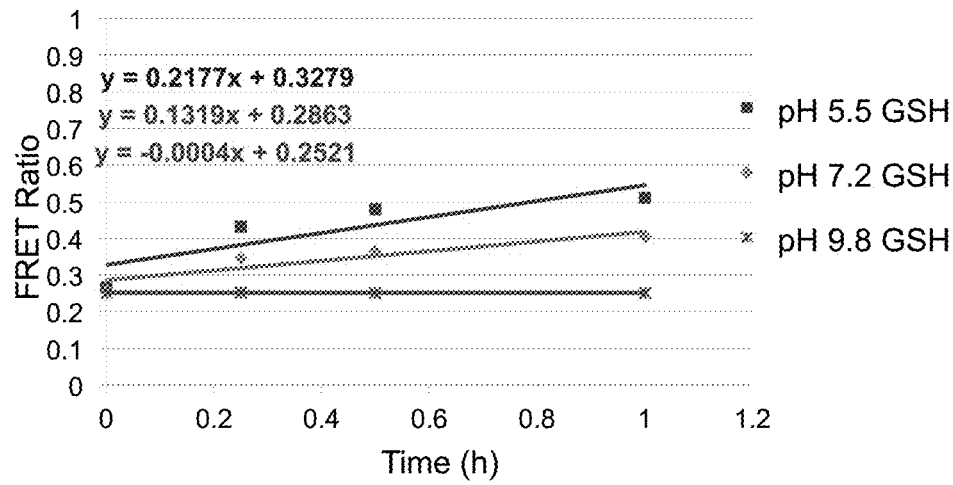
FIG. 40. Data showing that nanogel being leaky in the presence of GSH. Overall, the nanogel is leaky at lower pH or in the presence of GSH when the nanogel behaves mainly like the lower pH nanogel, because the GSH has inherently lower activity at lower pH. At normal pH, 7.2, the nanogel stably encapsulates molecules without GSH, but becomes leaky in the presence of GSH.
Figure 40:
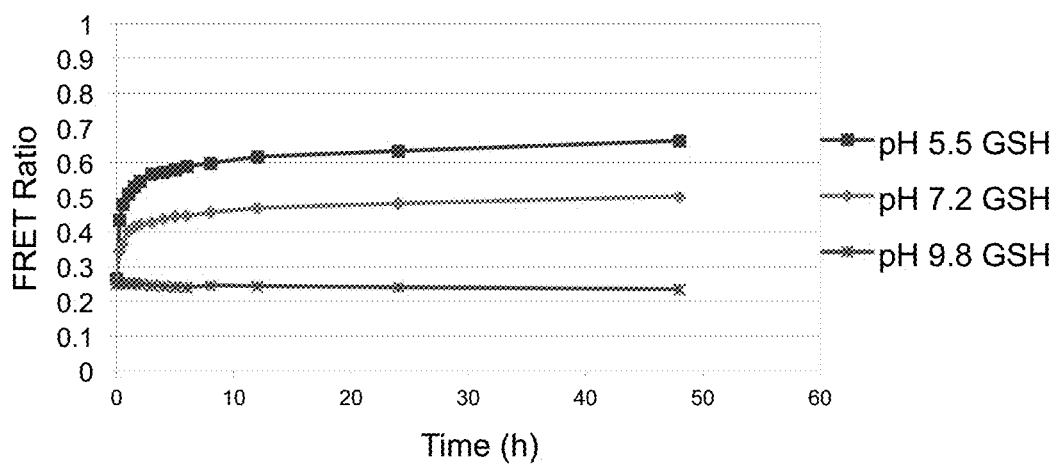
Figure 41:
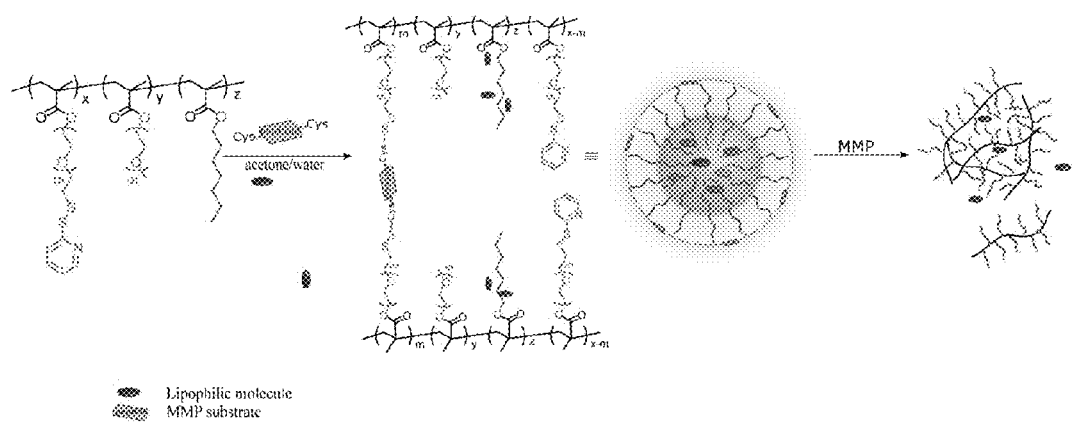
FIG. 41. Schematic illustration of MMP induced guest release.
Figure 42:
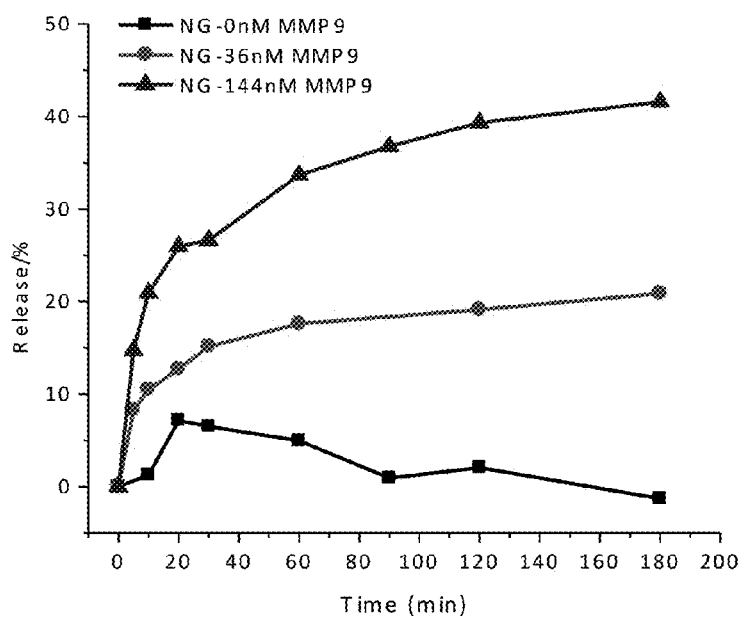
FIG. 42. DiI release from MMP9 substrate cross-linked nanogel.

Post-nanogel modification can be used to eliminate the remaining pentafluorophenyl groups to ensure that the hydrophobic interior of the nanogels maintains its hydrophobicity in solution and that all of the reactive and potentially toxic pentafluorophenol groups have been removed from the system. The nanogel modification was done by treating the cross-linked nanogels with an excess of octylamine prior to dialysis purification. The reaction was monitored by both FTIR and $^{19}F$ NMR. Pentafluorophenol functions as a good leaving group for an incoming amine, which then replaces the ester with an amide bond which can be clearly visible in the FTIR spectra (FIG. 39) with the disappearance of the peak at 1780 $cm^{-1}$ corresponding to ester C=O stretching and evolution of a peak at 1650 $cm^{-1}$ corresponding to amide C=O stretching.

Figure 32:
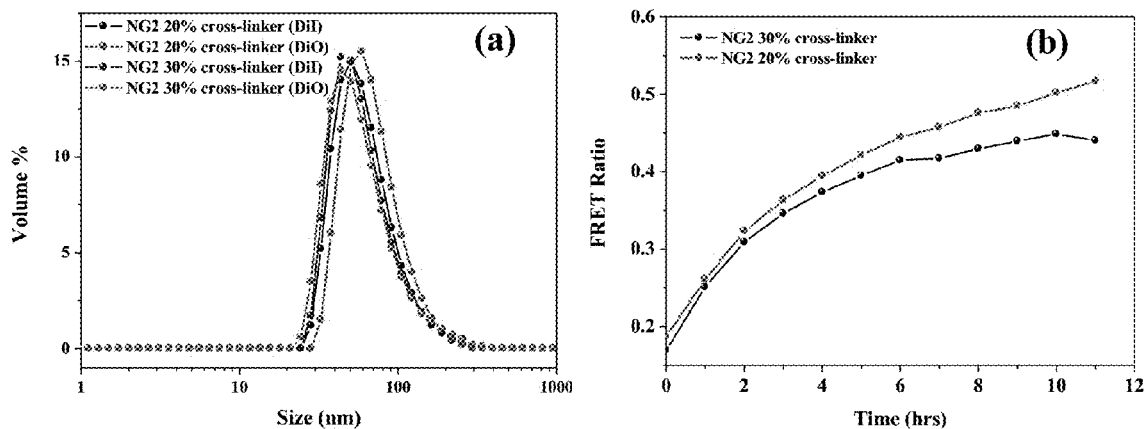
FIG. 32. (a) DLS of NG2 with different cross-linking densities loaded with 0.75 wt % DiO/DiI; (b) FRET ratio vs. time plot of mixed solutions of NG2 prepared with 0.75 wt % DiI/DiO.

Cross-linking density of polymers can play a significant role in imparting the required stability for the nanogels. Cross-linking density can be used to tune the rate of exchange. To study the role of cross-linking density on release, nanogels with 20 and 30% cross-linking density with octylamine (NG2) loaded with DiO and DiI were prepared. The synthesized nanogels were ~80 nm in size (FIG. 32a). Guest interchange dynamics were monitored by measuring the fluorescence. The FRET ratios were plotted against time (FIG. 32b). The nanogels with higher cross-linking density showed less FRET ratio compared with nanogels having lower cross-linking density. These results are further evidence that the degree of cross-linking plays crucial role in tuning guest exchange dynamics.

Figure 33:
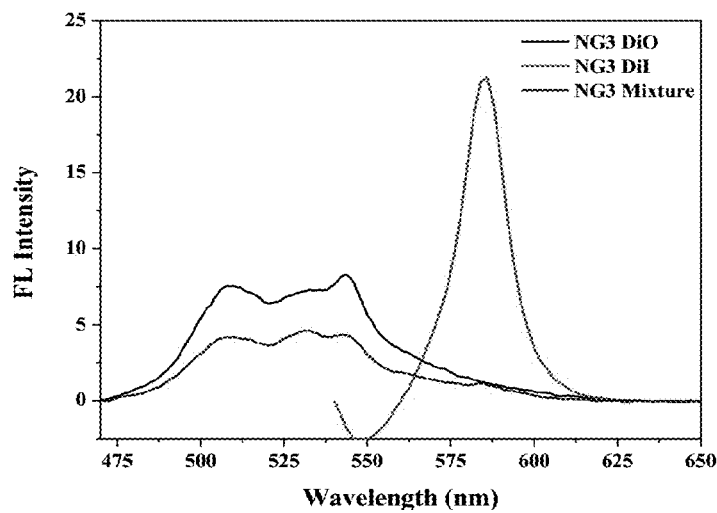
FIG. 33. Fluorescence spectra of NG3 loaded with 0.75 wt % DiO/DiI and nanogel mixture.
Figure 34:
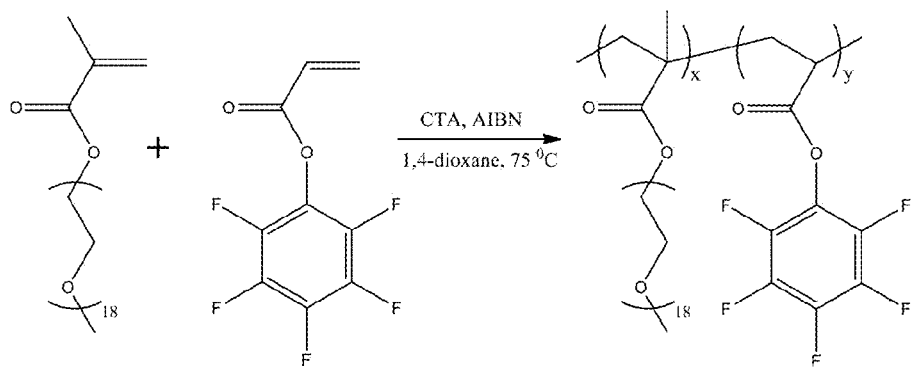
FIG. 34. $^1$H NMR spectrum of random copolymer PEGMA-r-PFPA.
Figure 34:
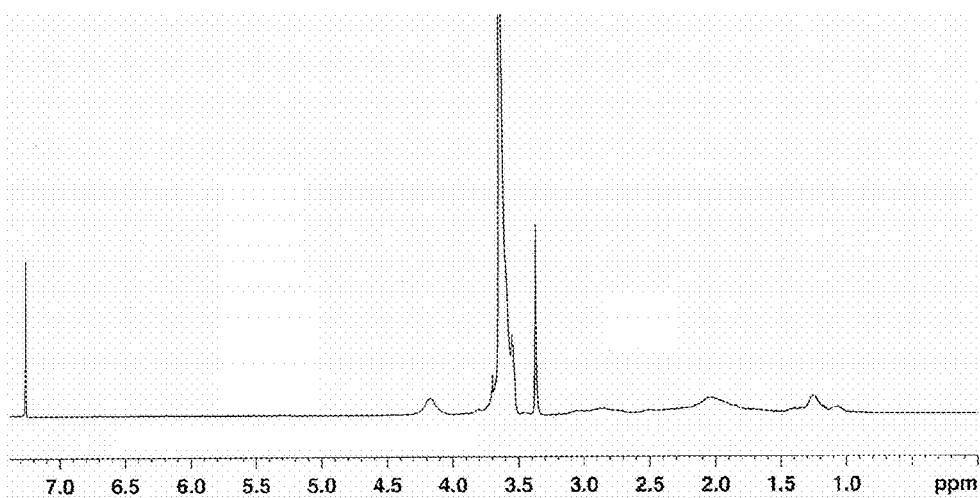
Figure 35:
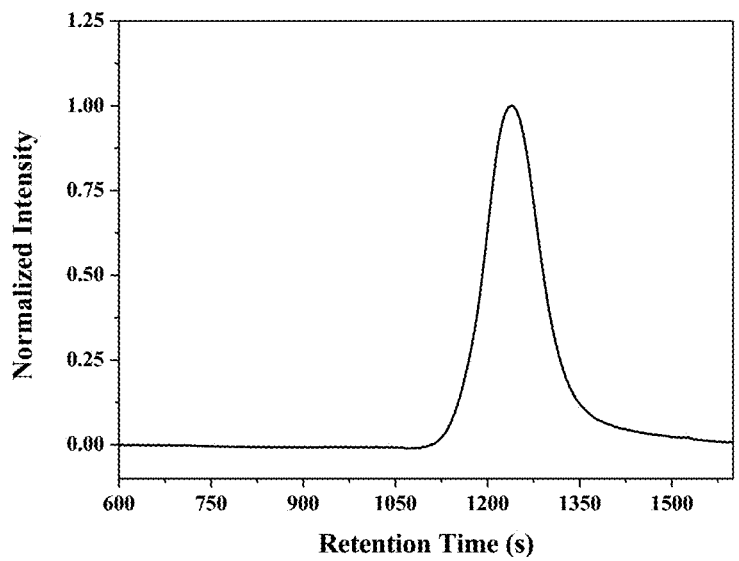
FIG. 35. GPC chromatogram of random copolymer PEGMA-r-PFPFA.
Figure 36:
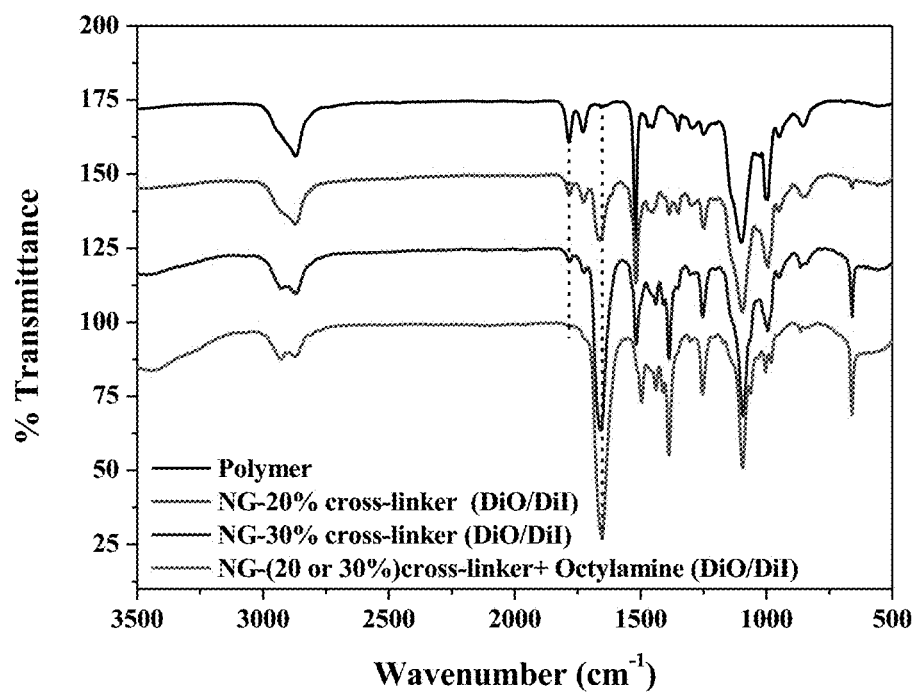
FIG. 36. FTIR spectra of polymer and nanogels with different cross-linking densities.
Figure 37:
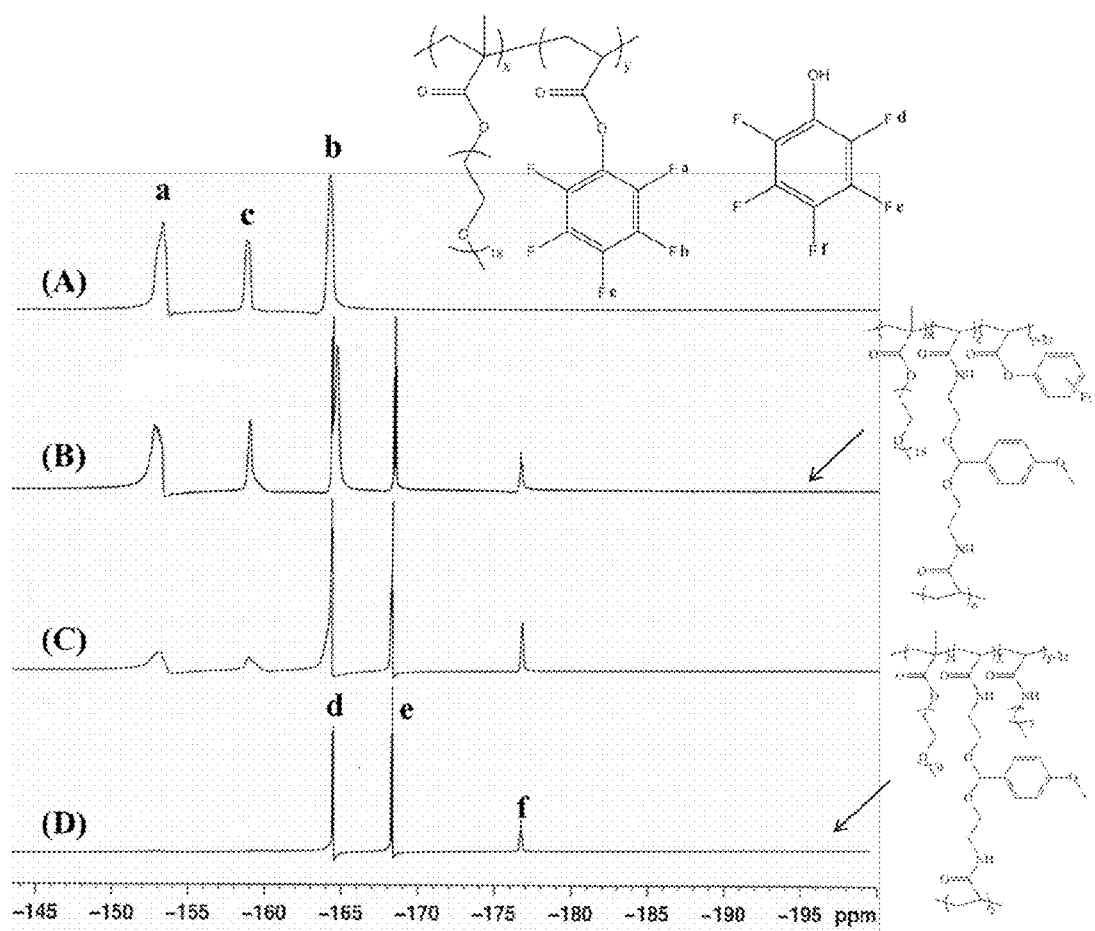
FIG. 37. $^{19}$F NMR spectra at different stages of nanogel synthesis: (A) Polymer; (B & C) Nanogels with 20 and 30% cross-linker; (C) nanogels with 20 and 30% cross-linker+ Octylamine.
Figure 38:
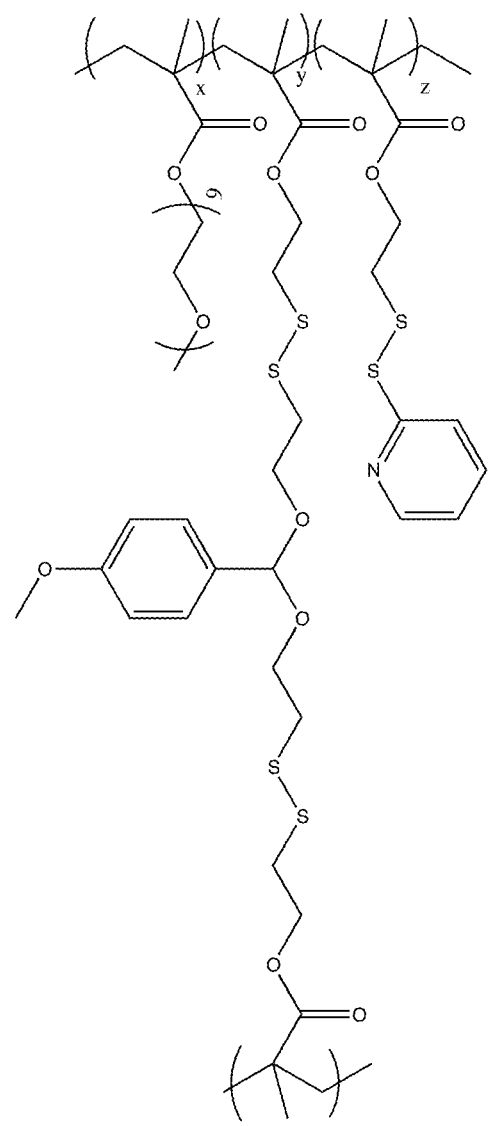
FIG. 38. An exemplary compound according to the invention.

To probe the role of hydrophobicity in the guest encapsulation stability, nanogels (NG3) were synthesized with 20% and 30% cross-linking density and, in place of hydrophobic octylamine, aminoethoxy ethanol was used which is hydrophilic in nature. The dye loading was 0.75 wt %. Fluorescence spectra of the nanogels loaded with DiO and DiI and nanogel mixture for the FRET experiment were recorded and are shown in FIG. 33. Fluorescence and FRET experiments shows that decreasing the hydrophobicity of the nanogel core decreases encapsulation stability. The nanogels loaded with DiO, DiI and the nanogel mixture showed distorted fluorescence spectra with very low emission intensity indicating that the dye molecules either poorly encapsulated in the nanogel or precipitating out. Decreasing the hydrophobicity of the nanogel would decrease the hydrophobic loading as well as encapsulation stability of hydrophobic guest molecules within the nanogel. Therefore by maintaining the hydrophobic environment, nanogels with octyl side chains create a more preferable environment for the dye molecules, thereby increase the ability of the nanogel to hold the dye molecules and limiting exchange with the surrounding aqueous environment.

These results indicate that the pH/$CO_2$ responsive nanogels synthesized by chemical cross-linking can be used as drug carriers for intelligent drug delivery. The pH/$CO_2$ responsive nanogel systems based on amphiphilic random copolymer can supply a minimal release of guest molecules at normal physiological pH, and to fully release the loaded guest molecules at values slightly lower than normal physiological pH. The nanogels were pH/$CO_2$ responsive and their release properties can be tuned by adjusting both the cross-linking density and the nature of the pentafluorophenyl substituting agent. Decreasing the hydrophobicity of the nanogel core decreases encapsulation stability.

Experimental

Synthesis Bis-trifluoroacetamide-acetal (a)

N-(2-Hydroxyethyl)-2,2,2-trifluoroacetamide (5.03 g, 32.0 mmol), 5 Å molecular (5 g), p-anisaldehyde (1.12 g, 8.2 mmol), were dissolved in dry tetrahydrofuran (20 mL) under Argon atmosphere. After stirring under Ar for 30 minutes, concentrated $H_2SO_4$ (10 µL) was added. The reaction mixture was left to stir overnight at room temperature. The reaction was then quenched with triethylamine (0.75 mL, 5.3 mmol) and directly loaded onto a silica gel column. The column was eluted with a 20:80 ethyl acetate/hexane mixture and then a 35:65 ethyl acetate/hexane mixture to afford 2.41 g (68%) of the acetal. $^1H$ NMR (400 MHz, $CDCl_3$) (δ

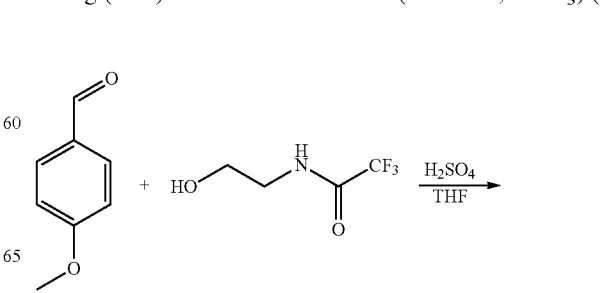

-continued

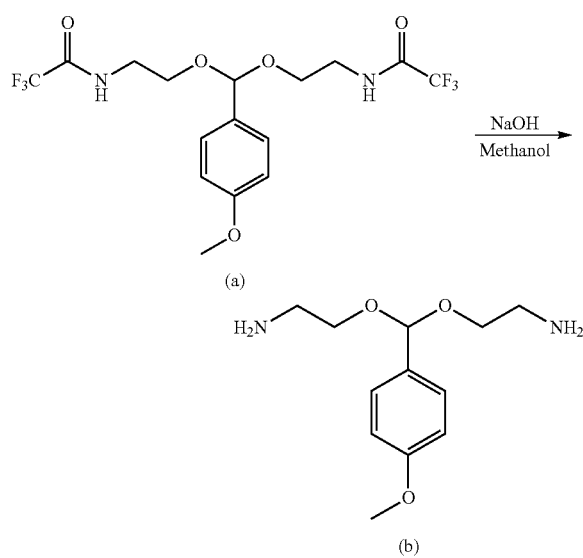

ppm): 7.34 (d, 1H), 6.95 (d, 1H), 6.71 (b, 2H), 5.50 (s, 1H), 3.84 (s, 3H), 3.73 (m, 4H), 3.63 (m, 4H).

Synthesis of Cross-linker (b)

Bis-trifluoroacetamide-acetal (138 mg 0.3 mmol) and NaOH (51 mg, 1.3 mmol) were dissolved in dry methanol (3 mL). The reaction mixture was stirred for 24 hours. Methanol was then removed by purging with argon and the product was then dissolved in dichloromethane, filtered and concentrated to afford 60 mg (78%) of the product. $^1$H NMR (400 MHz, Methanol-d4) (δ ppm): 7.40 (d, 1H), 6.92 (d, 1H), 5.52 (s, 1H), 3.79 (s, 3H), 3.62-3.52 (m, 4H), 2.80 (m, 4H).

Synthesis of Random Copolymer (PEGMA-r-PFPA)

In a 10 mL Schlenk flask pentafluorophenyl acrylate (PFPA) (238 mg, 1 mmol) was added to Poly(ethylene glycol) methyl ether methacrylate (PEG) (407 mg, 0.43 mmol), AIBN (1.18 mg 0.007 mmol), 4-cyano-4-((thiobenzoyl)-sulfanyl)pentanoicacid (16 mg, 0.0573 mmol) and 1,4-dioxane (650 μL). The solution mixture was then degassed using three freeze-pump-thaw cycles. The flask was sealed and immersed in preheat oil bath at 75° C. for 4 days. The dioxane was removed and the mixture was dissolved in THF and then precipitated in hexane. The same procedure was repeated for three times to afford the pure polymer. Yield 85%. GPC (THF) $M_n$: 24,000. PDI: 1.20. $^1$H NMR (400 MHz, CDCl$_3$) (δ ppm): 4.02-4.21, 3.50-3.81, 3.31-3.39, 2.71-3.18. $^{19}$F NMR (300 MHz, CDCl$_3$) (δ ppm): −152 (2F), −158 (1F), −164 (2F). By comparing the integral of terminal methyl protons in the polyethylene glycol unit and polymer backbone proton in both polyethylene glycol and pentafluorophenyl units, the molar ratio was found to be 3:7 (PEG:PFPA).

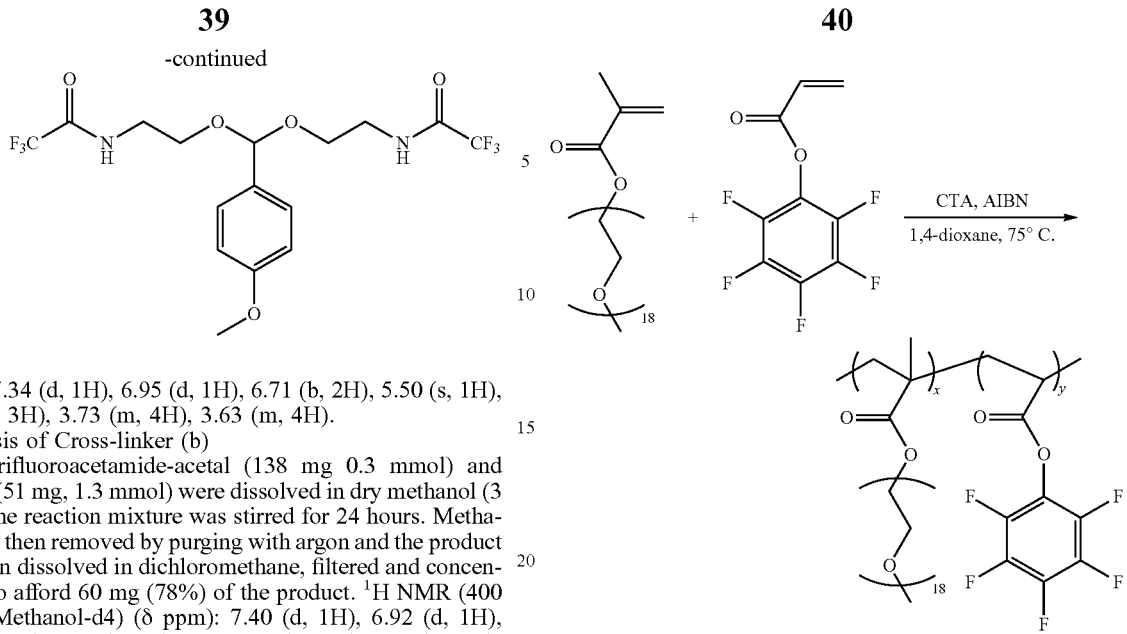

Nanogel Synthesis

Polymer (10 mg) and DiO/DiI (0.1 mg for 1 wt % and 0.075 mg for 0.75 wt %) were dissolved in 200 μL acetone and stirred for one hour. A calculated amount of acetal crosslinker was then added. It was then kept stirring for 6 h. The crosslinking reaction was followed by $^{19}$F NMR and FT-IR. After crosslinking, 1 mL of pH 7.8 PBS buffer was added and the mixed solution was stirred overnight at room temperature, open to the atmosphere to remove the acetone. After the complete evaporation of acetone 1 mL of more buffer solution was added and the mixture was passed through a syringe filter to remove any non-encapsulated DiO/DiI. The pentafluorophenol was removed from the nanogel solution by dialysis in pH 7.8 distilled water using a membrane with a molecular weight cut-off of 7,500 g/mol.

Nanogel Modification

The nanogels with desired crosslinking density were prepared initially by following the above procedure. After 6 h, 2 equivalents of octylamine with respected to remaining PFP groups after cross-linking were added to the nanogel solution and stirred the reaction for another 4 h. Cross-linking and post-nanogel substitution were monitored by FTIR. After completion of the reaction, 1 mL of pH 7.8 PBS buffer was added and the mixed solution was stirred overnight at room temperature, open to the atmosphere to remove the acetone. After the complete evaporation of acetone added 1 mL more buffer solution and the mixture was then filtered to remove insoluble DiO/DiI. The pentafluorophenol was removed from the nanogel solution by dialysis in pH 7.8 distilled water using a membrane with a molecular weight cut-off of 7,500 g/mol.

Changing Surface Properties of Nano-assemblies with Change in Environment

A polymeric system is disclosed herein which has the features of: (i) The system is a charge generation process (neutral to positive), instead of a charge conversion process (negative to positive), which design can further reduce non-specific binding, prior to the charge-generation step; (ii) the charge generation is rapid; (iii) the pH-induced charge-generation step is reversible, i.e. the surface charge is environment-dependent, but not permanent; (iv) the scaffold that exhibits these features is nanoscale and can non-covalently bind hydrophobic guest molecules; and (v) the charge-generation step does not produce any small molecule by-products.

The self-crosslinked polymer nanogels was used that was derived from an amphiphilic random copolymer. (Ryu, et al. 2010 *J. Am. Chem. Soc.* 132, 17227.) The polymer precursor was based on a hydrophilic oligoethylene glycol functionalized co-monomer and a hydrophobic pyridyl disulfide functionalized co-monomer.

Polymeric nanogels can be achieved by taking advantage of amphiphilic random copolymers that form nanoscale aggregates and by trapping them as nanogels through a crosslinking reaction in the hydrophobic component of the amphiphilic assembly. A series of random copolymers was developed by copolymerizing 2-(diisopropylamino)ethyl methacrylate (DPA), polyethylene glycol methacrylate (PEGMA) and 2-(pyridyldisulfide)ethyl methacrylate (PDSMA) monomers (Li, et al. 2013, *Chem. Sci.* 4, 3654). Nanogels were generated by crosslinking the pyridyldisulfide (PDS) moieties within the hydrophobic interior of the amphiphilic aggregates.

Figure 43:
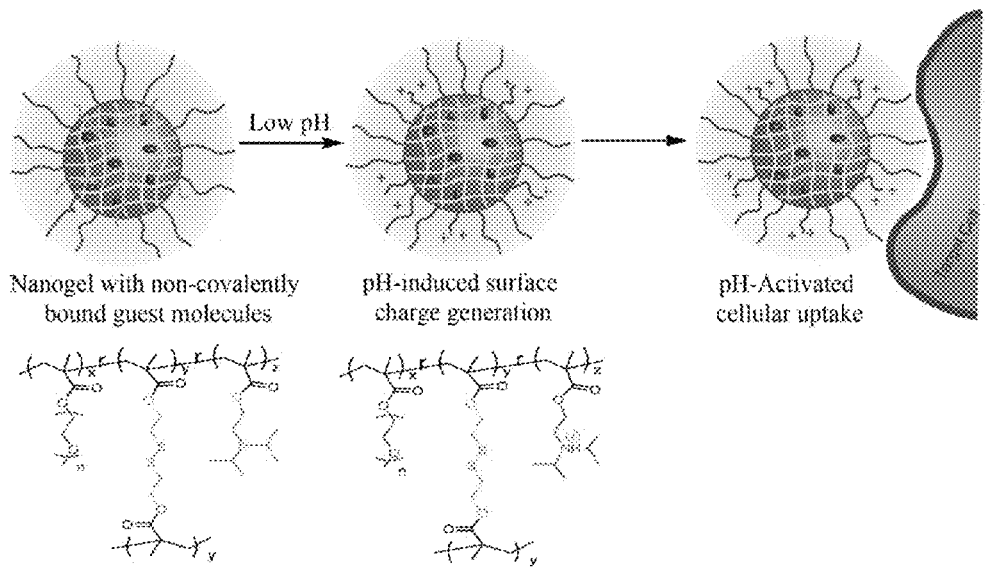
FIG. 43. Schematic illustration and chemical structure of polymeric nanogels for pH-induced surface charge generation and activated cellular uptake.

The DPA moieties are hydrophobic and are buried within the interior of the nanogels at neutral pH, but are protonated at pH, to generate a positively charged surface (FIG. 43), thus providing an opportunity for activated cellular uptake. The p$K_a$ of the protonated form of the amine is around 6.2, which indicates that at neutral pH this amine will be mostly unprotonated and thus will be hydrophobic. However, at a pH of 6.2, about 50% of the functional groups would be protonated. This protonation event is expected to be rapid and reversible, and the transformation also should not provide any byproducts.

Figure 44:
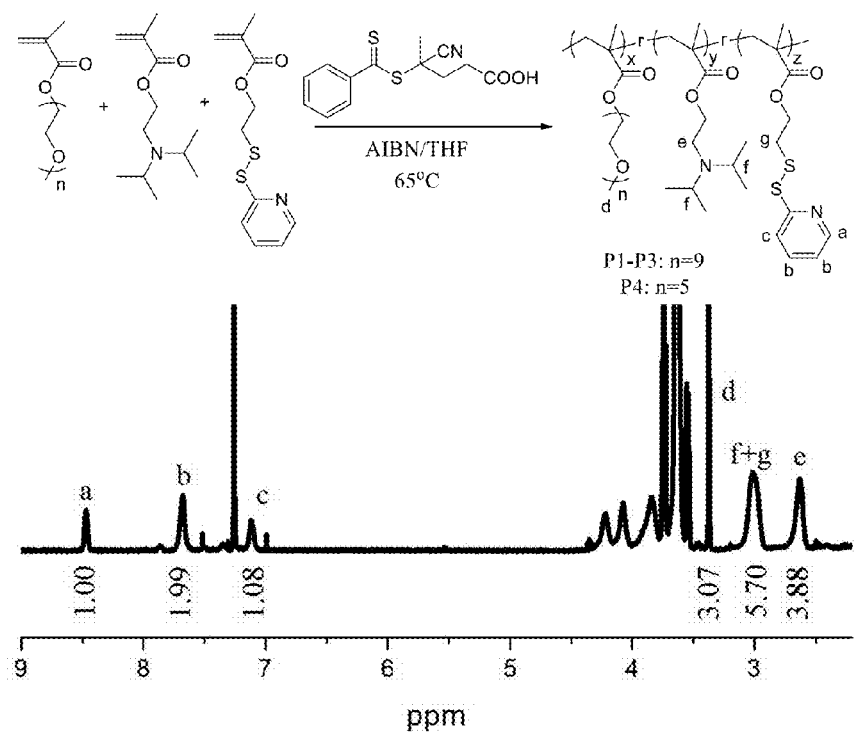
FIG. 44. Synthetic scheme and NMR spectrum of PEGMA-co-DPA-co-PDS random copolymer with PEG-MA:DPA:PDS=0.28:0.36:0.36 (P2) in CDCl$_3$.

The PEGMA-co-DPAMA-co-PDSMA copolymers were synthesized by a reversible addition-fragmentation chain transfer (RAFT) polymerization reaction (FIG. 44). Four different copolymers with varying comonomer compositions were targeted. Copolymers P1-P4 were synthesized by simply varying the feed ratio of the monomers during the polymerization. Copolymer P4 differs from the polymers P1-P3, as P4 is synthesized by using a PEGMA with shorter length polyethylene glycol side chain (~350 g/mol). After polymerization, the polymers were purified by precipitation in hexane, filtered, and washed to remove unreacted monomers.

TABLE 9

Characteristics of PEGMAx-co-DPAy-co-PDSz copolymers (P1-P4)

| Sample code | x/y/z$^a$ | Mn(kDa)$^b$ | Ð$^b$ |
|---|---|---|---|
| P1 | 0.28/0.19/0.53 | 8.26 | 1.29 |
| P2 | 0.28/0.36/0.36 | 10.2 | 1.34 |
| P3 | 0.26/0.49/0.25 | 8.36 | 1.23 |
| P4$^c$ | 0.26/0.32/0.42 | 12.3 | 1.51 |

The polymers were characterized by NMR and GPC. The characteristic resonances of PDS ($\delta H_a$=8.46, $\delta H_b$=7.67, $\delta H_c$=7.10), PEGMA ($\delta H_d$=3.37 ppm) and DPA ($\delta H_e$=2.62, $\delta H_f$=3.02 ppm) moieties were used to calculate the relative ratios of the monomer incorporated in the polymer (FIG. 44). The number-average molecular weights ($M_n$) and dispersity (Ð =$M_w/M_n$) of the copolymers were evaluated by GPC. The results are summarized in Table 9.

These polymers were converted into the corresponding nanogels, NG1-NG4, by first dispersing these polymers in aqueous phase. The nanoscale aggregates are locked-in as nanogels by generating intra-aggregate disulfide crosslinks. The crosslinking reaction was executed by adding a calculated amount of dithiothreitol (DTT), which cleaves the disulfide bond of corresponding amount of PDS moieties. The free thiols generated in this process then react with remaining PDS functionalities in the polymer chain (both intra- and inter chain) to provide the cross-linked polymer nanogel. The intra-aggregate nature of the crosslinking reaction insures that the nanogel size is tightly controlled by the size of the nanoscale aggregate. The extent of the PDS cleavage was conveniently monitored by the absorption peak that corresponds to the pyridothione by-product.

The pH-dependent charge-generation features in these nanogels were investigated through zeta potential measurements. Upon decreasing the pH of the solution, the surface charge of the nanogel changed to positive with the transition from negative to positive charge at a pH ~6.2.

Tuning the pI of Nanogels by Varying Monomer Ratio in the Polymer

Figure 45:
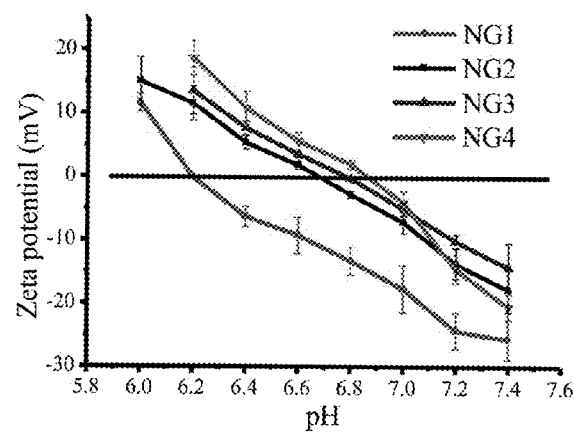
FIG. 45. Change in the zeta potential of nanogels as a function of pH. NG1-NG4) were synthesized from P1-P4 at pH 10. All nanogel crosslinking densities were 100%, achieved by adding 50 mol % DTT with respect to PDS groups.

The pH at which the surface charge is generated in the nanogel can be conveniently tuned by simply altering the ratio of DPA unit in the copolymer. The nanogels NG1-NG3 were used to investigate their isoelectric point (pI). Due to the apparent negative charge on the PEG surface, the pH at which the surface charge of the nanogel becomes neutral was named as the nanogel's pI. It was found that the pI indeed increased with the ratio of DPA in the copolymer, as shown in FIG. 45. The pI of the NG1 was found to be 6.2, while those of the NG2 and NG3 were found to be 6.7 and 6.8 respectively.

Tuning the pI of Nanogels by Varying of Length of OEG Units and Crosslinking Density NG4, which differs from other nanogels only in the length of OEG units—these are shorter. It was found that the pI of the nanogel from NG4 was indeed slightly higher than those of NG2 and NG3, even though the relative ratio of DPA units was smaller in the case of NG4.

The crosslinking density of NG4 was higher than that of NG2 and NG3 in the experiment above. The pI of NG4 was higher than those of NG2 and NG3. However, if crosslinking density were to have an effect on the pI, it was anticipated that the nanogels with lower crosslinking density to exhibit higher pI. This is because the DPA groups that are buried inside the core can be more easily presented on the nanogel surface upon protonation, when the crosslink density is lower, due to the greater flexibility of the polymer chains. (Li. L, et al. *Langmuir*, 2013, 29, 50-55).

To test this further, nanogels of three different crosslink densities were prepared using the polymer P1 by adding different amounts of dithiothreitol (DTT) (30, 40 and 50 mol % against the precursor PDS groups) during the crosslinking reaction. These nanogels were labeled as NG1-60x, NG1-80x, and NG1-100x respectively, indicating the percent crosslink densities in each of the nanogels.

Figure 46:
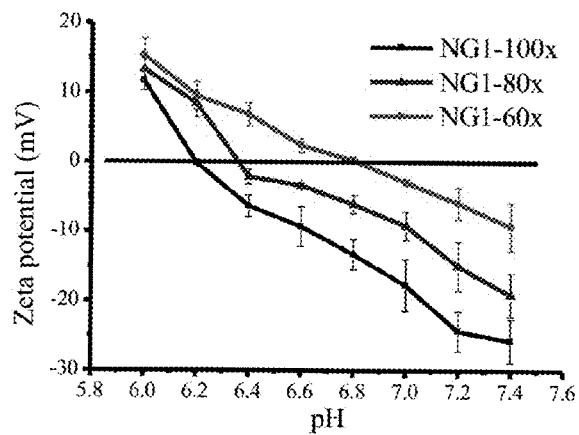
FIG. 46. Change in the zeta potential of nanogels with different crosslinking density as a function of pH. All three nanogels were synthesized from P1 at pH10, and the crosslinking density was varied by using appropriate amount of DTT.

When examining the change in surface charge with pH (FIG. 46), the pI for the NG1-60x was much higher than that of NG1-80x, which was higher than that of NG1-100x. These results indicate that: (i) the pH-induced surface presentation of the DPA units, buried in the core of the nanogel when hydrophobic and unprotonated, was influenced by the flexibility of the polymer chains; and (ii) the higher pI of NG4, compared to NG2 and NG3, was not due to the crosslink density variation and is indeed due to the shorter OEG units on the surface of NG4.

Tuning the pI of Nanogel by Varying the pH During Nanogel Preparation

Nanogels were synthesized at pH 5, 6, 8, and 10 using P1 and 50% DTT to obtain NG1-5, NG1-6, NG1-8, and NG1-

Figure 47:
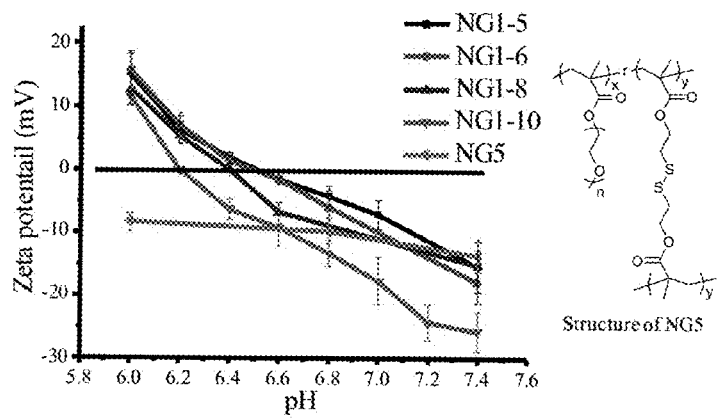
FIG. 47. Change in the zeta potential of nanogels as a function of pH. NG1-x nanogels were synthesized from P1 at different pH, represented as NG1-x where x stands for the pH at which the nanogel was prepared. Crosslinking density in all nanogels was fixed at 100%. For comparison, nanogel without DPA units (NG5) was prepared; structure of NG5 is also shown.

10, respectively. After syntheses, all these nanogels were brought to identical solution conditions through extensive dialysis. Then, the charge-conversional possibility of the nanogel was investigated by measuring the zeta potential at different pH (FIG. 47). It was found that the pI of the nanogel was dependent on the preparative conditions. For example, the pI for NG1-8 was found to be ~6.4, while the pI of the NG1-5 and NG1-10 were found to be 6.5 and 6.2 respectively.

It was also demonstrated that the observed differences were not due to any adventitious effects and were indeed due to the DPA units. A structurally similar nanogel NG5 was prepared, but without the DPA units, having $M_n$: 13 kDa; PD: 1.3, with PEG:PDS ratio of 3:7 from $^1$H NMR.

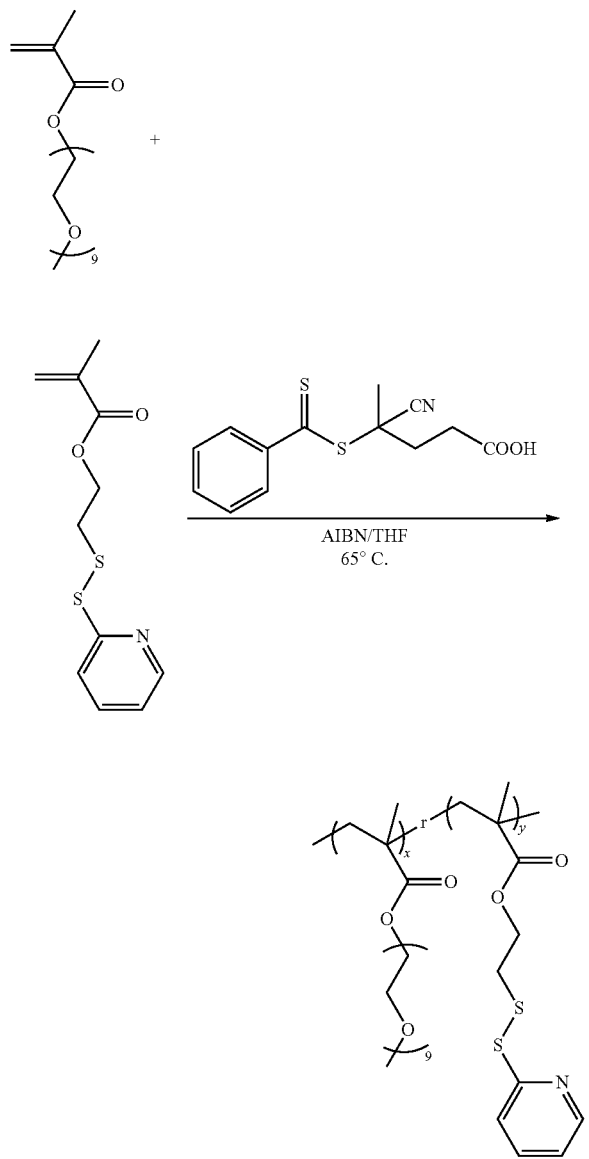

The zeta potential of the nanogel without DPA units remained at −10 mV at the whole pH range. This indicates that the observed pH-dependence is indeed due to the DPA units in the nanogel.

Encapsulation Stability of Nanogels at Different pH

Figure 48:
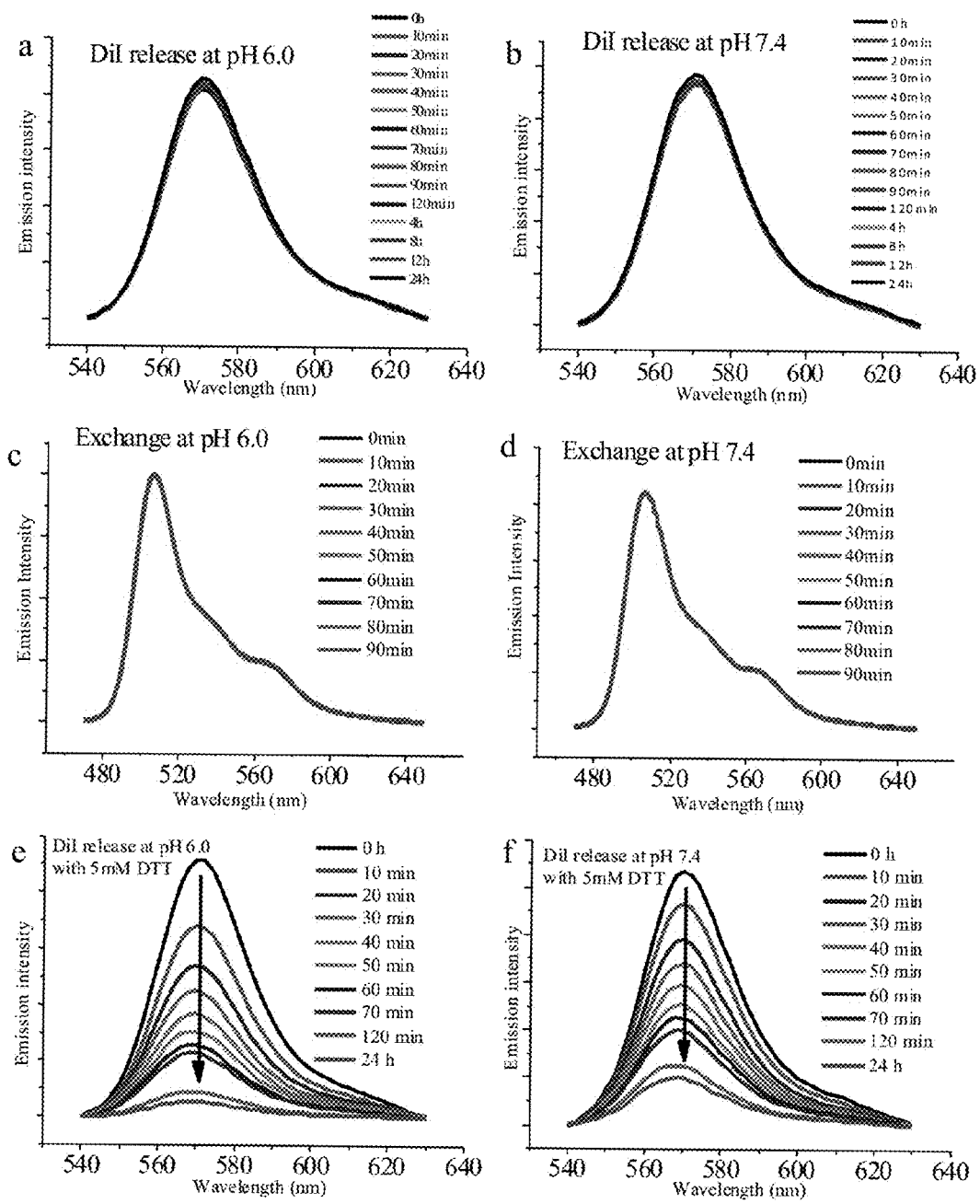
FIG. 48. Encapsulation stability of nanogel at different pH (a-d). DiI release experiment, a) at pH 6.0, b) at pH 7.4. FRET experiment based DiI/DiO exchange, c) at pH 6.0, d) at pH 7.4; DiI release experiment in the presence of 5 mM DTT in solution, e) at pH 6, f) pH 7.4. The nanogels used were synthesized from P2 (100% crosslinked).

To test encapsulation stability at different pH, DiI-incorporated nanogel solutions were prepared and their fluorescence was monitored over time at pH 7.4 and 6.0. It was found that the fluorescence was unchanged even over a 24 hours time period (FIGS. 48a-48b). This indicates that although the surface charge of the nanogels change with pH, their host-guest capabilities do not change with pH. To further test whether there is a stable encapsulation of the guest molecules within the nanogel, a recently developed fluorescence resonance energy transfer (FRET) experiment was utilized. (Jiwpanich, S et al. *J. Am. Chem. Soc.*, 2010, 132, 10683-10685).

Two different solutions were prepared, one with a FRET donor and another with a FRET acceptor. When these solutions are mixed, if the extent of FRET increases with time, then the nanogel is leaky. If there is no change in FRET, then the encapsulation is stable. In this experiment, the measure of encapsulation stability is independent of the ability of the nanogel to solubilize the dye molecules through amphiphilic driving forces. 3,3'-Dioctadecyloxacarbocyanine perchlorate (DiO) is a well-known higher energy FRET donor partner for DiI. The FRET evolution was investigated at both pH 7.4 and 6.0, where it was found that the extent of FRET did not change over a 24 hours time period (FIG. 48c, 48d). This confirms that the guest molecules are indeed stably encapsulated, independent of whether the DPA units are protonated or not.

Stimuli Responsive Features of Charge Conversional Nanogels

Figure 49:
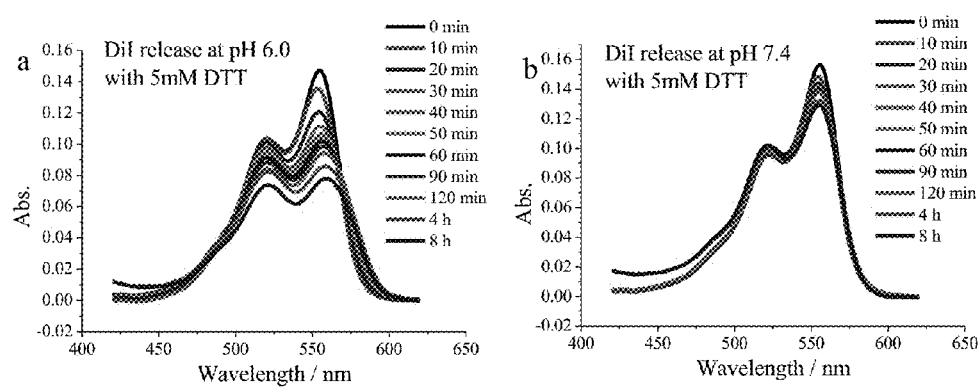
FIG. 49. Absorption spectra for DiI release experiment at a) pH 6.0 with 5 mM DTT and b) pH 7.4 with 5 mM DTT.

Since these are disulfide-based crosslinks, the nanogels are sensitive to reactive thiols such as DTT and glutathione. In the presence of 5 mM DTT, the nanogels were found to be quite leaky, with a large extent of the guest molecules released within 2 hours (FIGS. 48e-48g). This feature was found to be independent of the pH. To insure that the observed change was not an adventitious pH response to fluorescence, the absorbance of the solution was also monitored under these conditions. Similar results were observed for the DiI release, via. absorption spectra (FIG. 49).

Figure 50:
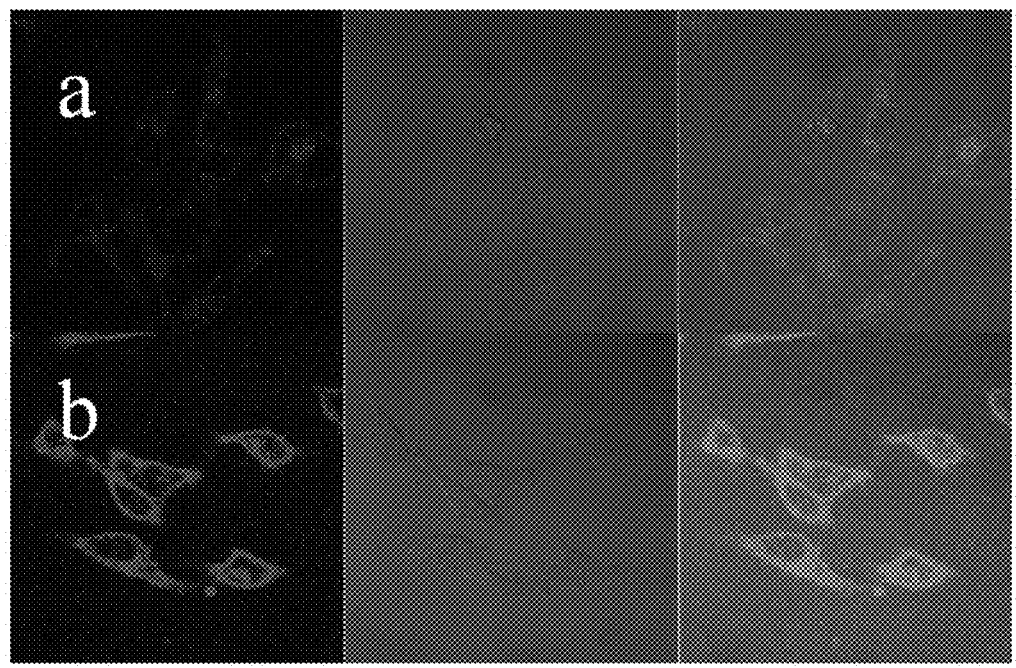
FIGS. 50. (a) and (b) are confocal images of NG2, containing DiI at pH 7.4 and 6.5 respectively, after incubation with HeLa cells for 2 hours. The nanogels used were 100% crosslinked. Cells were imaged using a 63× oil-immersion objective. Within each image set, left panel is the red channel that shows DiI emission; middle panel is the DIC image, and right panel is an overlap of both.

Cell Internalization Behavior of Nanogels with Changes in pH 1,1'-dioctadecyl-3,3,3',3'-tetramethylindocarbocyanine perchlorate (DiI) was used as the guest molecule due to its hydrophobicity and fluorescence emission wavelength that is suitable for studying the cellular uptake using confocal laser scanning microscopy (CLSM). The internalization behavior of DiI-encapsulated NG2 was investigated at the normal extracellular pH of 7.4 and $pH_e$ of 6.5 with the HeLa cell line. Significantly different cellular uptake was observed for the DPA nanogels under these conditions. As shown in FIG. 50, the red fluorescence is significantly higher at pH 6.5, compared to pH 7.4. This difference can be attributed to the possibility that the DPA nanogel would become positively charged upon the protonation of DPA groups at lower pH and thus enhance the cellular internalization.

Figure 51:
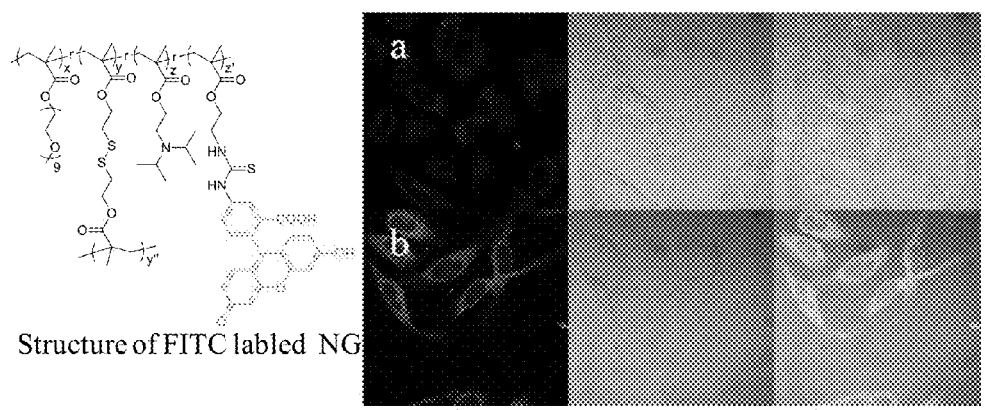
FIGS. 51. (a) and (b) are confocal images of fluorescein-labeled DPA nanogel at pH 7.4 and 6.5 after incubation with HeLa cells for 2 hours. The concentration of the nanogels used was 1 mg/mL. Cells were imaged using a 63× oil-immersion objective. Within each image set, left panel is the green channel that shows FITC emission; middle panel is the DIC image, and right panel is an overlap of both.

To further confirm that the pH-dependent internalization is indeed due to change in surface charge, nanogels with covalently attached fluorescein were prepared and incubated with the HeLa cells for 2 hours, at both pH 6.5 and pH 7.4. From the optical microscopy images, it is clear that the cells treated with nanogels at pH 6.5 exhibit much higher cellular uptake, compared to the same nanogels at pH 7.4 (FIG. 51).

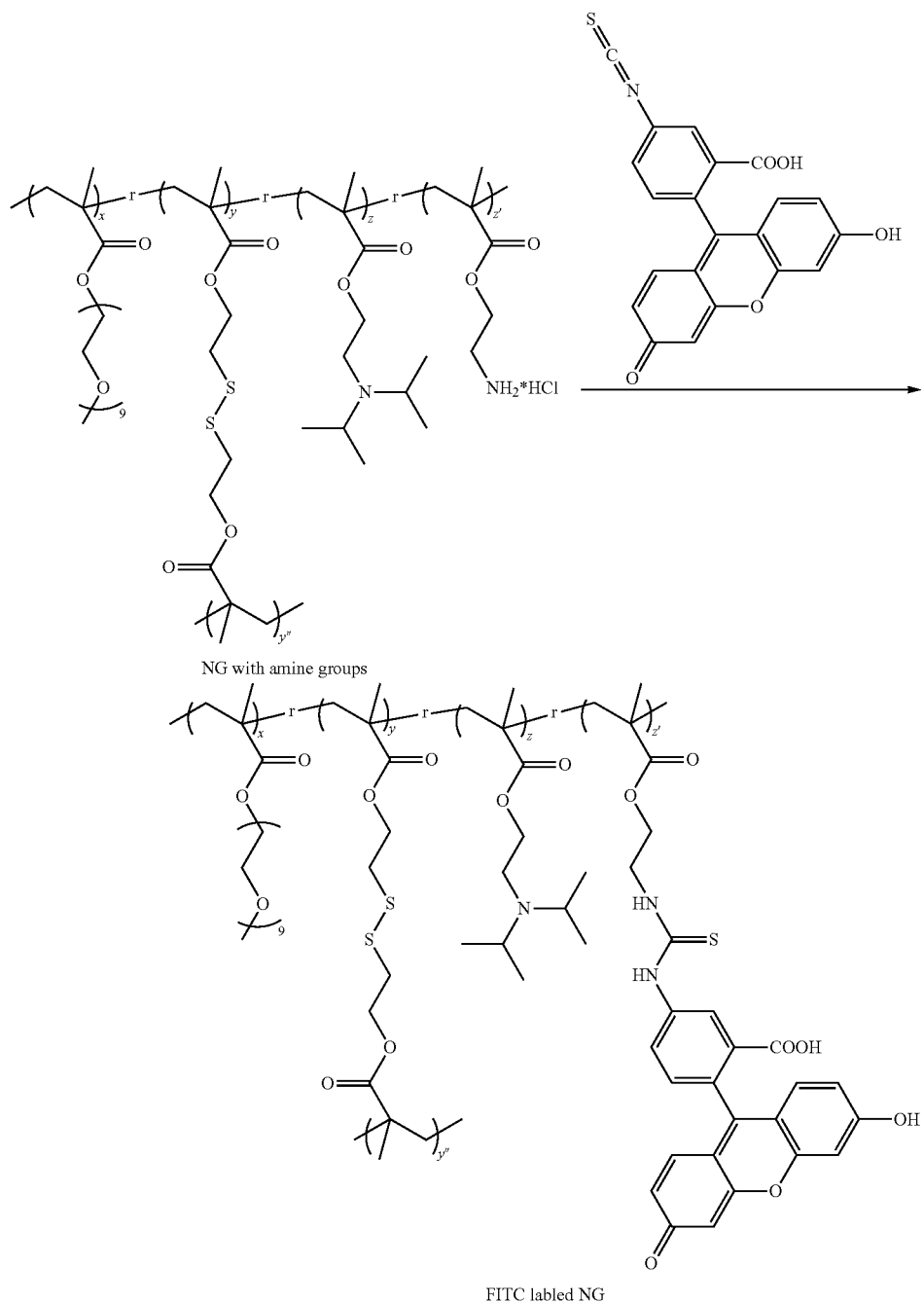

FITC labled NG

These results confirm that the difference in fluorescence images at two different pHs, with the DiI-encapsulated nanogels, is not due to the non-covalently encapsulated guest leakage. These results also support that the difference in cellular uptake is indeed due to the greater nanogel uptake at pH 6.5, most likely due to the difference in surface charge. These results also indicate that the current nanogel system can be used in drug delivery via both physical encapsulation and chemical conjugation.

Thus, the nanogel is capable of transforming into a positively charged nanogel at acidic pH. The nanogel system attains a positive charge at a pH that is relevant to the slightly acidic tumor extracellular environment. It has been shown that: (i) the co-incorporation of DPA units to PEG-based nanogels can lead to effective pH-dependent charge generation; (ii) the pI of the DPA nanogel can be systematically tuned by varying the (a) percentage DPA units present in the nanogel, (b) percentage of DPA units that are initially exposed on the nanogel surface, and (c) crosslink density; (iii) the charge generation process can be utilized to enhance cellular uptake at $pH_e$, compared to the normal extracellular pH. It is remarkable that this charge generation event results in enhanced cellular uptake, even though the length of the OEG units are much higher than the side chains that contain the DPA moieties; and (iv) non-covalently encapsulated guest molecules are stably encapsulated at both pH and are thus effectively taken up by the cells at lower pH without any leakage.

Dual Stimuli-Dual Response Systems from Polyelectrolyte-Nanogel Complexes

Figure 52:
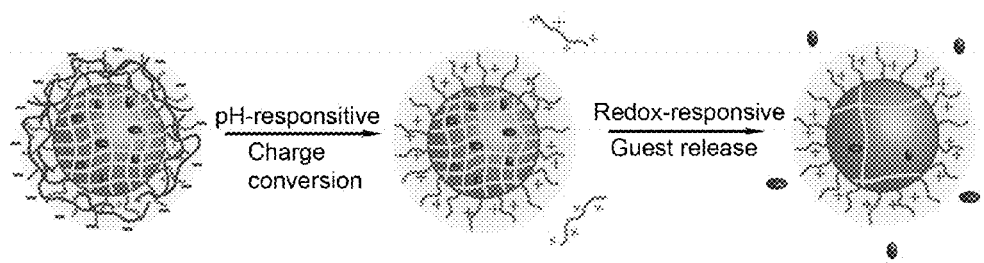
FIG. 52 Representation of dual stimuli-dual responsiveness of polyelectrolyte-nanogel complexes.

A supramolecular assembly with pH and redox stimuli responsive characteristics was achieved by the development of a polyelectrolyte-nanogel complex (Scheme 1). In this complex, the polyelectrolyte has charge-conversional features—i.e. the charge in the polyelectrolyte will change from negative to positive charge at low pH. The nanogel is capable of sequestering hydrophobic guest molecules that are released in response to change in the redox environment. The nanogel has a positively charged surface so as to complement the polyelectrolyte during the complex formation. A change in the charge of the polyelectrolyte in response to lowered pH compromises this electrostatic complementarity. The dissociation event causes a change in the surface properties of the nanoassembly. The electrostatically bound polyelectrolyte enhances the encapsulation stability of the hydrophobic guest molecules inside the nanogel. Dissociation of the polyelectrolyte from the nanogel then exposure to reducing conditions causes the guest molecules to be released from the nanogel. These expectations are schematically illustrated in FIG. 52.

Preparation of Polyelectrolyte-Nanogel Complex

The structures of the cationic polymeric nanogel, its precursor, the complementary anionic polyelectrolyte, and the products of the pH-induced reaction (the non-complementary cationic polyelectrolyte and the anionic small molecule) are all shown in Scheme 5. The nanogel was synthesized through the formation of an amphiphilic random copolymer nanoassembly, which was then crosslinked through an in situ reduction reaction as previously reported (Ryu, et al. 2010 *J. Am. Chem. Soc.* 132, 17227-17235.). The pyridyldisulfide units provided the hydrophobic component of the amphiphilic polymer and afforded the handle to execute the crosslinking reaction to generate the disulfide crosslinked nanogels. The quaternary ammonium moiety provided the cationic charge to the nanogel, while the N-isopropyl acrylamide unit played the role of charge-neutral, hydrophilic units that were used to modulate the cationic charge density in the nanogel. The anionic moiety in the polyelectrolyte was based on the monoamide formed from tetrahydrophthalic acid. The oligoethyleneglycol units present in the polyelectrolyte were used to tune the charge density of the polyelectrolyte.

Synthesis of Cationic Nanogel and Anionic Polymer

Scheme 5 shows the preparation of (a) precursor for cationic nanogel and anionic polymer; (b) nanogel; and (c) structures of nanogel-polyanion complexes and the disassociated products induced by lowering pH.

Scheme 5

(a) Synthesis of precursor for cationic nanogel and anionic polymer:

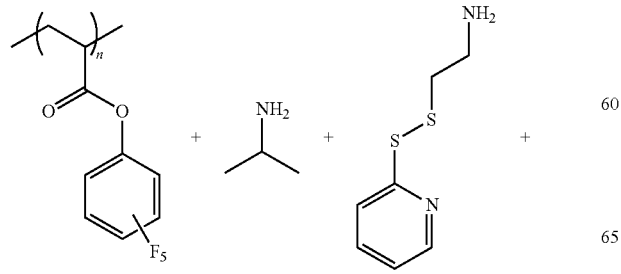

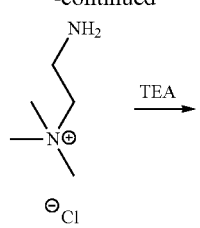

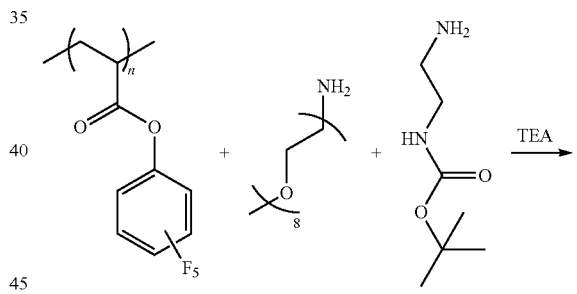

Polymer 1

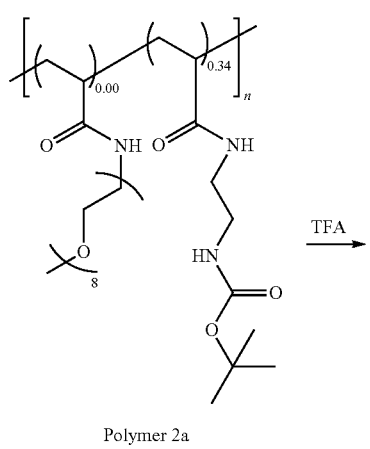

Polymer 2a

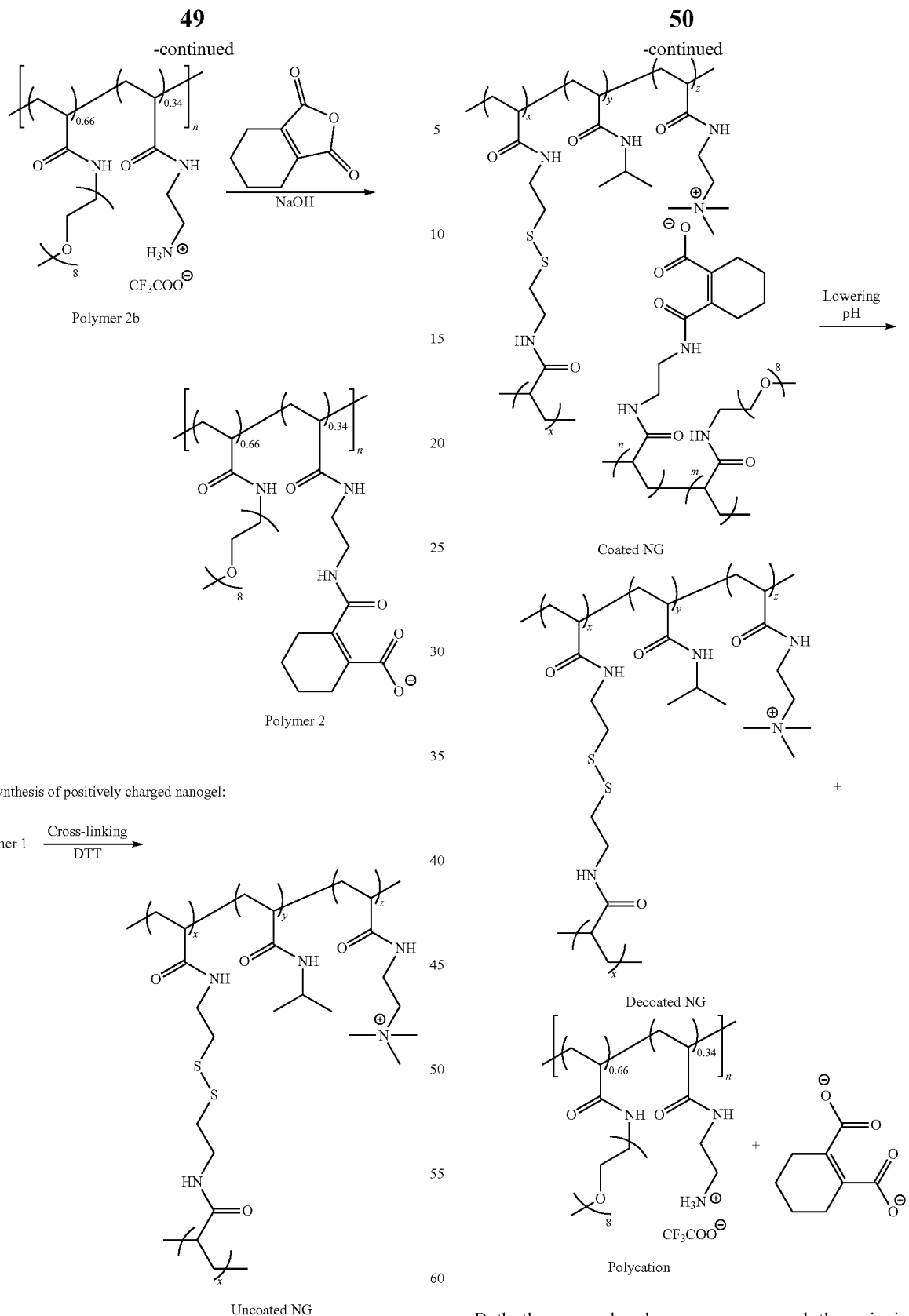

(b) Synthesis of positively charged nanogel:

(c) Electrostatic mediated coating and decoating:

Both the nanogel polymer precursor and the anionic polyelectrolyte were prepared through a simple substitution reaction of poly(pentafluorophenyl acrylate) (PPFPA) with appropriately functionalized primary amines (Scheme 5). The cationic nanogel was synthesized by treatment of activated acrylate ester PPFPA with isopropylamine (0.3 equiv.), pyridyldisulfide containing 2-aminoethanethiol (0.5 equiv.), and 2-aminoethyl-trimethylammonium chloride (0.2 equiv.). The targeted copolymer 1 was obtained in 85% yield. The percentage of the co-monomers in the polymer was assessed to be 0.42:0.39:0.19 using NMR, which shows that the ratio corresponds to the feed ratio of the monomers in the substitution reaction. The substitution reaction was found to be complete, as discerned from the C=O stretching bands in IR as reported before (FIG. 53) (Zhuang, et al. 2012 ACS Macro Lett. 1, 175-179.)

Figure 53:
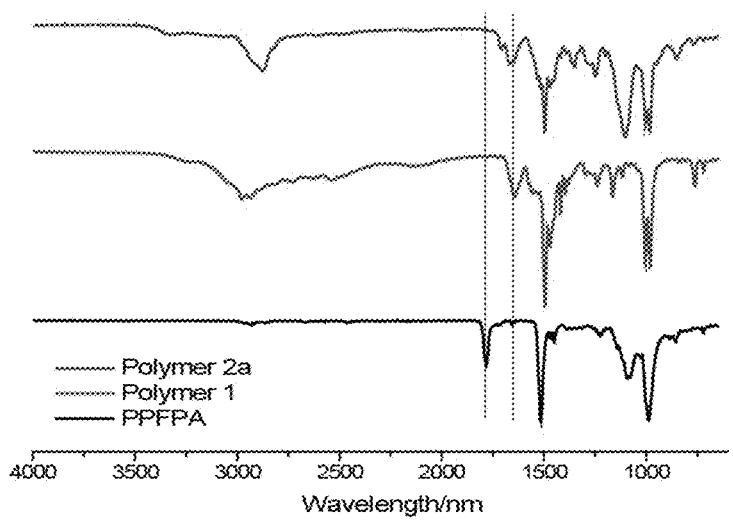
FIG. 53. Preparation of polymer precursors for cationic nanogel and anionic coating polymer monitored by FTIR.
Figure 60:
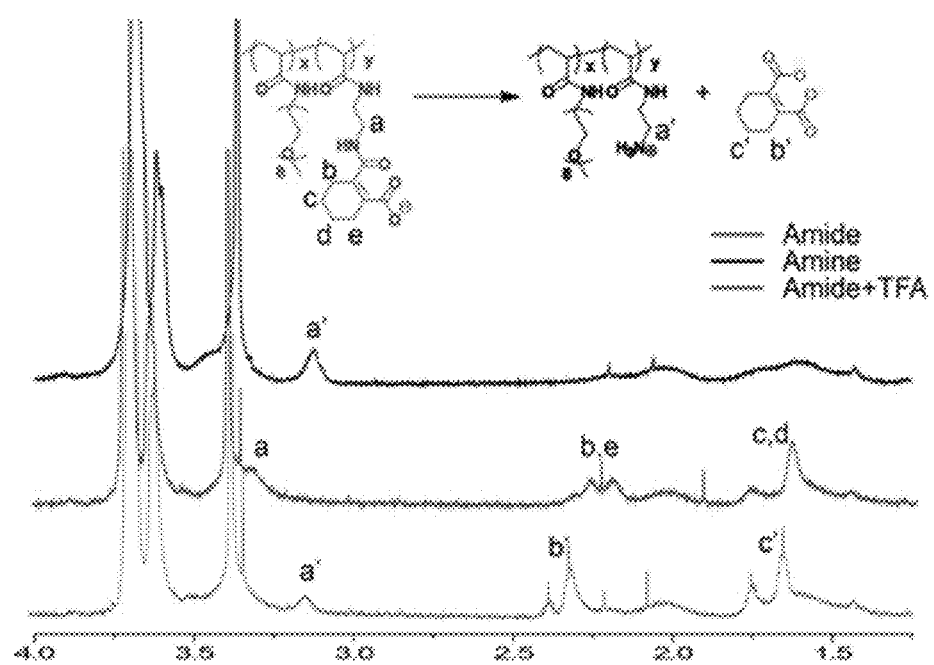
FIG. 60. Charge conversion of polymer 2 induced by the addition of TFA.

The polymer was then converted to the corresponding disulfide crosslinked nanogel by treating the polymer with dithiothreitol (DTT) based on the previously reported procedure (Ryu, et al. 2012 Biomacromolecules 13, 1515-1522; Ryu, et al. 2010 J. Am. Chem. Soc. 132, 8246-8247.). Similarly, the polyelectrolyte was synthesized by first treating PPFPA with mono-amino-oligoethyleneglycol and N-Boc-ethylenediamine in 0.7:0.3 ratio to afford polymer 2a. The ratio of the co-monomer in the polymer 2a was found to be 0.66:0.34 using NMR. As with the syntheses of the polymer nanogel precursor, quantitative substitution of the pentafluorophenyl moiety in this case was also ascertained using IR (FIG. 53). The Boc-protecting group was removed by treating the polymer with trifluoroacetic acid (TFA). The resulting primary amine polymer 2b was treated with 3,4,5,6-tetrahydrophthalic anhydride to convert this cationic polymer to the carboxylic acid containing anionic polymer 2. This substitution conversion reaction could conveniently be reversed, if the pH of the aqueous solution was lowered (FIG. 60). This reversal indeed formed the basis for the pH-induced charge conversion.

Preparation and Characterization of Polyelectrolyte-Nanogel Complex

The nanogel-polyanion complex was prepared through electrostatic interactions. To a polymer 2 solution with a concentration of 10 mg/mL at pH 9.0, a calculated amount of positively charged nanogel with a concentration of 1 mg/mL was added dropwise and the mixture was kept stirring for 30 min. Then, free polyanion was removed from the mixture by ultrafiltration to afford pure nanogel-polyanion complex.

Figure 54:
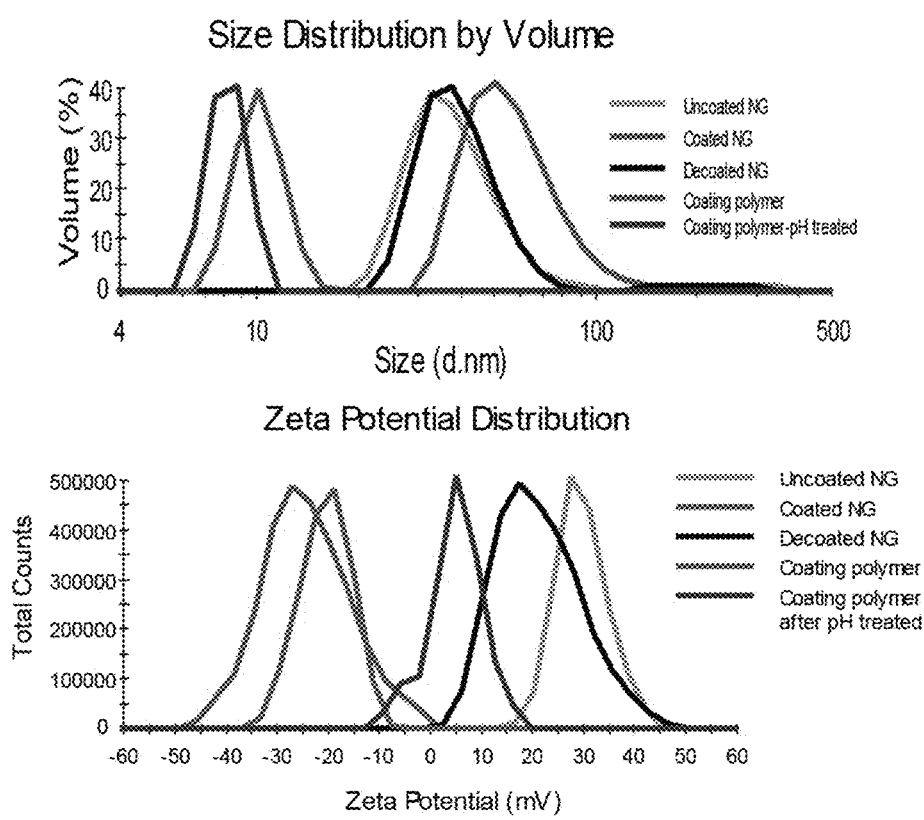
FIG. 54. Changes on (a) size and (b) zeta potential of cationic nanogel after coating and decoating.

The nanogel-polyelectrolyte complex was characterized using dynamic light scattering (DLS) and zeta potential measurements. The size of nanogel itself was found to be 30 nm as measured by DLS, as shown in FIG. 54a. After being coated by polymer 2, the size increased to 55 nm indicating the formation of nanogel-polyanion complex. Since the surface of the nanogel contained positively charged quaternary ammonium moieties, the nanogel was expected to be cationic and thus exhibit a positive zeta potential. Indeed the zeta potential of the nanogel was found +30 mV (FIG. 54b). A nanogel efficiently coated with the negatively charged polymer to form a nanogel-polyelectrolyte complex showed an anionic surface charge with a zeta potential of −30 mV.

pH-Induced Polyelectrolyte Dissociation

Figure 62:
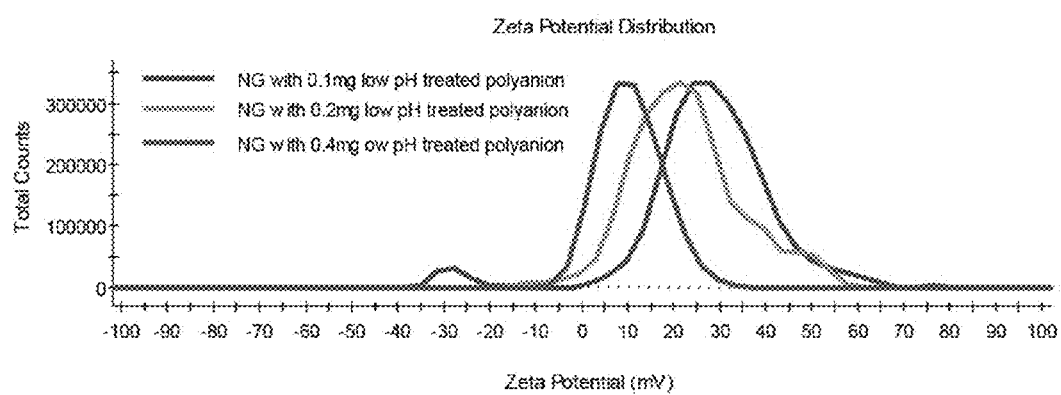
FIG. 62. Zeta potentials of mixture of low pH treated polymer 2 with positively charged nanogel.

The design approach was that the pH-induced conversion of the anionic coating polymer to a cationic polymer causes the polymer to dissociate from the nanogel due to electrostatic repulsion. The size and the zeta potential of the nanogel upon lowering the pH of the solution were observed. As shown in FIG. 54a, the size of the nanogel changed back to ~30 nm upon decreasing the pH of the solution to 4.4 for 30 min. This size corresponded to the uncoated nanogel suggesting that the polyelectrolyte had dissociated from the nanogel. This was further supported by the zeta potential measurements. As shown in FIG. 54b, lowering pH of the solution caused the zeta potential to positively shift to +18 mV. The fact that the charge did not fully recover to that of the cationic nanogel itself (+30 mV) might indicate that the dissociation was not complete. However, it was also possible that the smaller zeta potential (+5 mV) of the dissociated polymer contributed to make the overall zeta potential in the nanogel-polyelectrolyte mixture lower. This possibility was tested by mixing the low pH treated anionic polymer 2 and the cationic nanogel and measuring the zeta potential (FIG. 62). The fact that increasing concentrations of the polymer could reduce the overall zeta potential indicates that the latter possibility of the dissociated polymer contributing to the observed lower zeta potential indeed exists.

Size Modification

Figure 55:
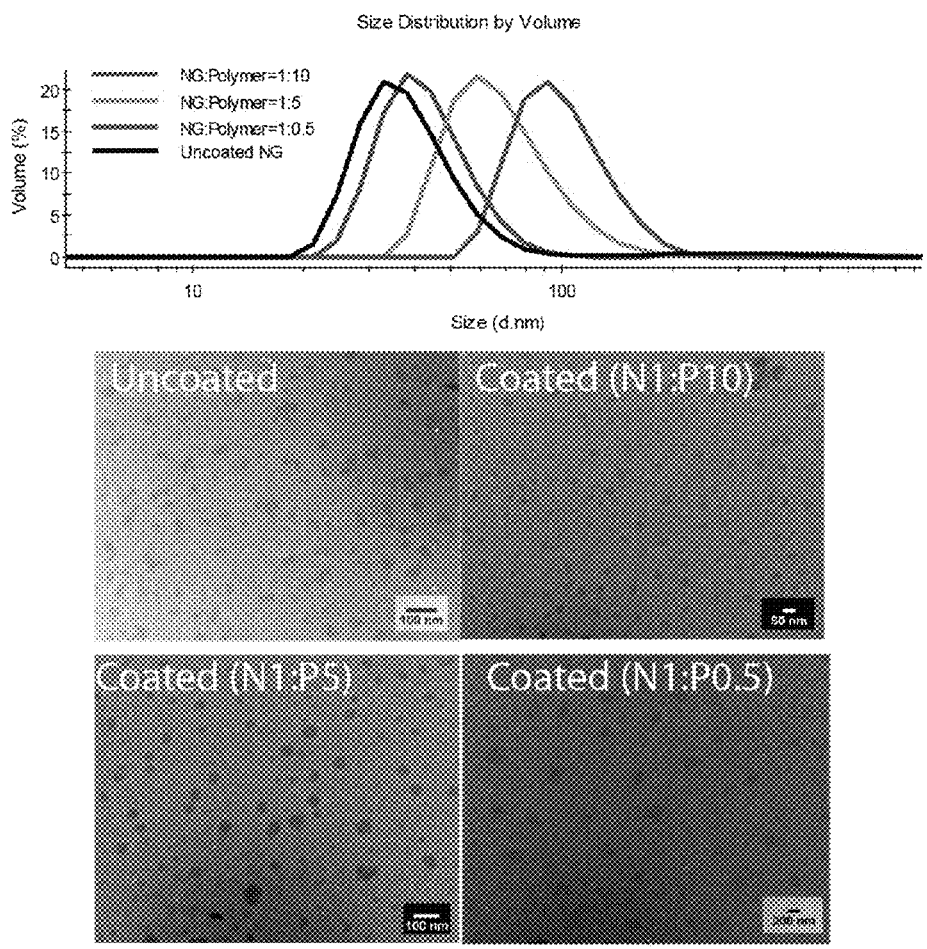
FIG. 55. Tunable size of nanogel/polyanion complex observed by DLS (top) and TEM (bottom).
Figure 61:
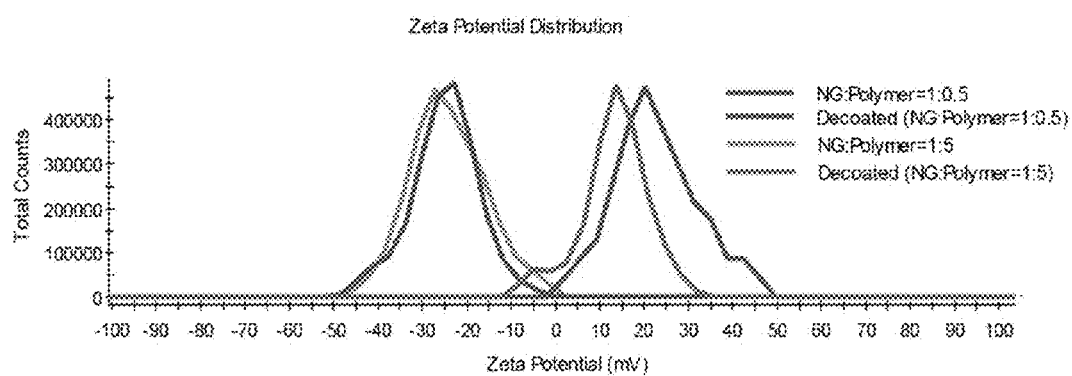
FIG. 61. Zeta potentials of nanogel-polyanion complexes before and after low pH treatment.

Tuning the size of these assemblies can be achieved by simply varying the ratio of the nanogel to the polyelectrolyte was investigated. When excess polyelectrolyte was used to form the complex, the polyelectrolyte may form more or less a monolayer coating on the surface of the nanogel without much nanogel aggregation. However, when the ratio of polyelectrolyte to the nanogel is smaller, nanogel aggregation should be possible. The complexes, studied above, were prepared using a 1:5 ratio of the nanogel to polyelectrolyte, where the complex size was 55 nm compared to the nanogel size of 30 nm. When this ratio was changed to 1:10, the size of the complex was only slightly increased or essentially unchanged from the original nanogel size (FIG. 55). To insure that the complexation had indeed occurred in this case, the zeta potential of the nanogel-polyanion complex was also investigated. The zeta potential of this complex had indeed changed to −30 mV (FIG. 61). The effect of changing the ratio to 2:1 was then evaluated and the size of the nanogel increased to ~100 nm (FIG. 55). Interestingly here too, the zeta potential of the nanogel was found to be −30 mV. These results were taken to suggest that 0.5 equivalent (in terms of weight %) was already sufficient to fully neutralize the positive charges on the surface of the nanogels and render the overall surface charge of the complex to be negative. All these nanogel complexes exhibited a pH-induced surface property change (FIG. 61).

Encapsulation and Guest Release of Polyelectrolyte-Nanogel Complex

The pH-sensitive features demonstrated an approach to alter the surface properties (surface charge) of a nanoassembly in response to the pH stimulus. The effect of the polyelectrolyte coating on the redox-sensitive nature of the nanogel was also investigated. Note that the nanogel is based on disulfide crosslinks; therefore, the encapsulated guest molecules could be released in response to the presence of thiol-based reducing agents such as glutathione (GSH). Accordingly, the effect of molecular release using Nile red as the guest molecule was examined.

Figure 56:
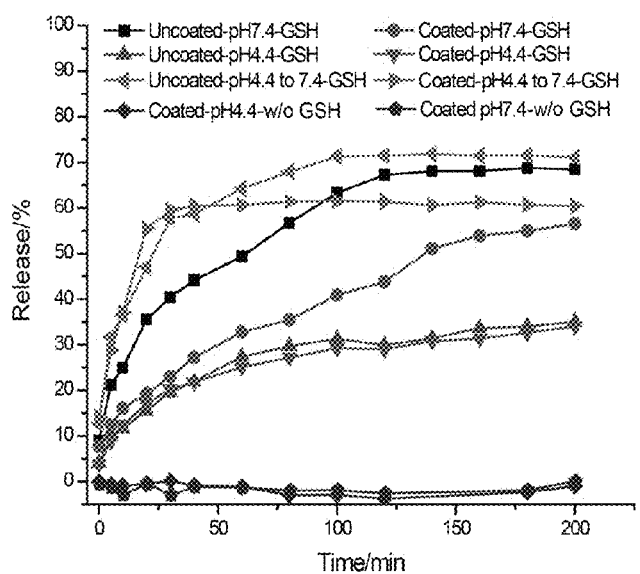
FIG. 56. Trigged release of Nile red from uncoated and coated nanogel in the presence of 1 mM GSH.
Figure 57:
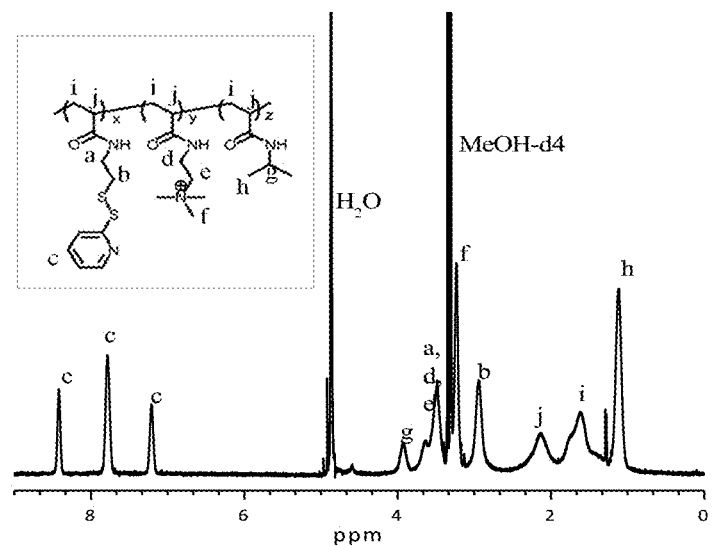
FIG. 57. $^1$HNMR of polymer 1 in MeOH-d4.
Figure 58:
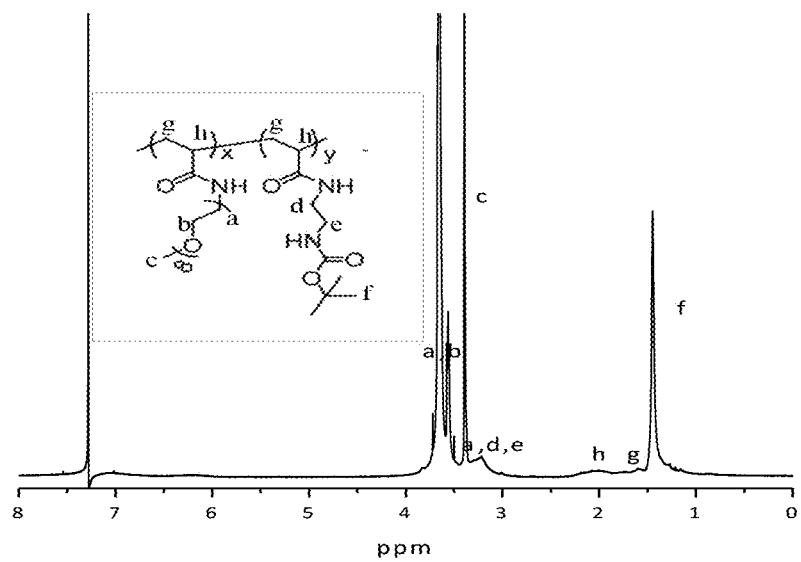
FIG. 58. $^1$HNMR of polymer 2a in CDCl$_3$.
Figure 59:
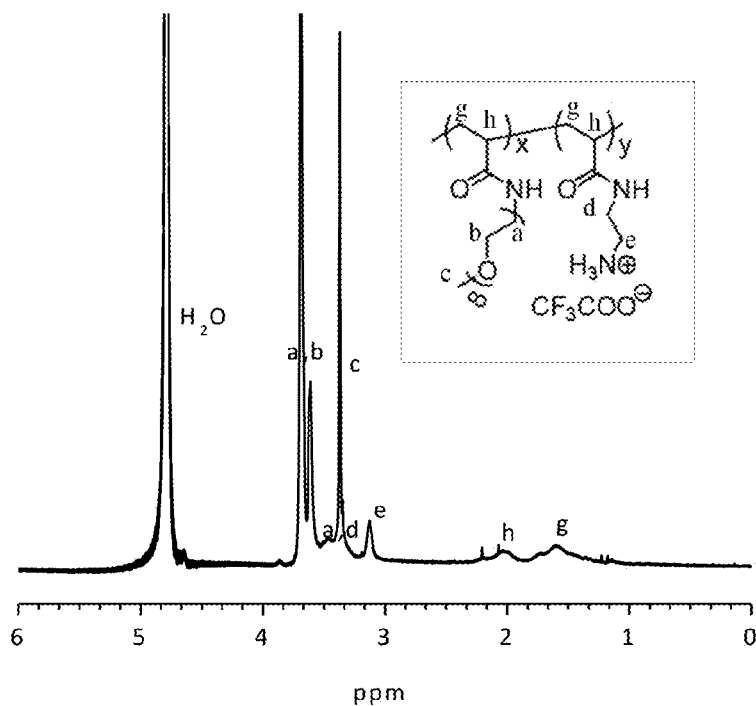
FIG. 59. $^1$HNMR of polymer 2b in D$_2$O.

First, to show that the pH and the redox stimuli could independently effect two different properties of the nanogel-polyelectrolyte complex, the effect of pH on the encapsulation stability of the nanogel was evaluated. As shown in FIG. 56, no guest release was observed with the nanogel-polyelectrolyte complex at pH 7.4 (where the polyelectrolyte coating was retained) and pH 4.4 (where the polyelectrolyte coating was rapidly removed due to charge conversion in the polyelectrolyte).

The guest release from the nanogel-polyelectrolyte complex was slower than that from the uncoated nanogel itself at pH 7.4, which suggested that the guest encapsulation was further stabilized by the polyelectrolyte coating. When the pH was lowered to 4.4, the pH at which the polyanion would be removed from the complex due to the charge conversion, the release from the nanogel-polyelectrolyte complex was substantially slower than the above two conditions. This observation was indeed surprising. However, it is important to note that GSH itself exhibits substantially different redox activity at lower pH. Therefore, the GSH-induced release of Nile red at pH 4.4 with the bare nanogel was compared. Indeed, the release profile was very similar to that of the nanogel-polyelectrolyte complex at this pH.

These results indicated that the polyelectrolyte was indeed removed from the nanogel to affect guest encapsulation as fast as that from uncoated nanogel. To insure that the redox-sensitive activity could be recovered after subjecting the nanogel complex to a pH change, the guest encapsulation stability of the nanogel-polyelectrolyte complex at pH 7.4 was investigated. Here the complex was first subjected to the pH-induced dissociation at pH 4.4 for 10 min; the pH of the solution then was raised to pH 7.4. The guest molecule was indeed rapidly released in the presence of GSH at this pH. The guest release profile was once again similar to that of the uncoated nanogel that was subjected to this pH cycling. Put together, these results suggested that the nanogel stably encapsulated the guest molecules at different pH, but differentially released the guest molecules due to polyelectrolyte complexation under the influence of the redox stimulus.

Thus, it has been demonstrated that: (i) a positively charged nanogel and a negatively charged polyelectrolyte can be conveniently coupled to make a nanogel-polyelectrolyte complex; (ii) since the polyelectrolyte undergoes a charge conversion at low pH, the nanogel-polyelectrolyte complex is dissociated under the influence of the pH stimulus; (iii) simple stoichiometric variations between the nanogel and the polyelectrolyte can be utilized to predictably vary the size of the complex; (iv) while the pH stimulus has a profound impact on the surface features of the nanogel-polyelectrolyte complex, it has no effect on the guest encapsulation; (v) on the contrary, redox stimulus does not affect the surface properties of the complex, but does influence the guest encapsulation in the nanoassembly; (vi) the polyelectrolyte complexation on the nanogel surface slightly higher encapsulation stability, compared to bare nanogel. In summary, it has been shown that the electrostatic driven complex between polymeric nanogels and polyelectrolytes can be utilized to design a nanoassembly that responds to two different stimuli, eliciting two diverse responses.

Experimental

Unless mentioned, all chemicals were used as received from Sigma-Aldrich. $^1$H-NMR spectra were recorded on a 400 MHz Bruker NMR spectrometer while $^{19}$F-NMR spectra were collected on a 300 MHz Bruker NMR spectrometer. Molecular weight of the polymers was measured by gel permeation chromatography (GPC, Waters) using a PMMA standard with a refractive index detector. THF was used as eluent with a flow rate of 1 mL/min. Dynamic light scattering (DLS) measurements were performed using a Malvern Nanozetasizer. FTIR spectra were recorded on a Perkin Elmer spectrometer.

Synthesis of PEG-NH$_2$

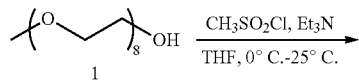

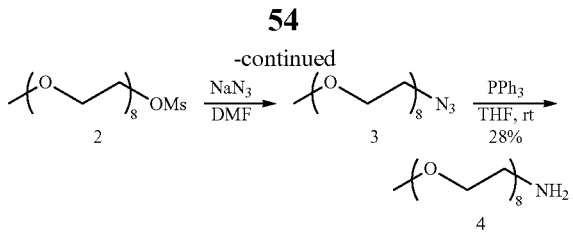

Synthesis of PEG-Ms 2

PEG-monomethyl ether 1 (35 g, 0.09 mol) was dissolved in 200 mL of anhydrous THF stirring it with triethylamine (12.14 g, 0.12 mol). Temperature of the mixture was lowered to 0° C. with an ice-salt bath. Mesyl chloride (13.75 g, 0.12 mol) was dissolved in 20 mL of anhydrous THF and added dropwise to the previous mixture at low temperature, stirring, and under argon atmosphere. The reaction mass got a milky aspect. The reaction was left overnight. Then, the solvent was evaporated and for the work up 100 mL of water was added to the remaining mass, to be extracted later with ethyl acetate (3×100 mL). The organic layers were collected on Na$_2$SO$_4$, filtered and concentrated to get the crude product 2, which was used without purification for the next step.

Synthesis of PEG-N$_3$ 3

The crude product 2 from the previous reaction was mixed with sodium azide (10.88 g, 0.17 mol) in anhydrous DMF (50 mL) and stirring with argon atmosphere, set to reflux. The reaction was left to react for 20 hours. Then, the DMF was distilled out. Water was added (300 mL) to the remaining mass, and then extracted with ethyl acetate (3×100 mL). The organic layers were reunited and washed with water (3×100 mL). The organic phase was dried over Na$_2$SO$_4$, filtered, and concentrated to get the crude product 3, which was used without purification for the next step.

Synthesis of PEG-NH$_2$ 4

The crude product 3 from the previous reaction was dissolved in anhydrous THF (100 mL) and mixed with triphenylphosphine (9.03 g, 0.03 mol). The reaction was left stirring and under argon atmosphere overnight. Then, water was added (100 mL) and stirred for 10 hours more. Then, the THF was evaporated and more water was added. A white solid formed was filtered out. The remaining solution was extracted with toluene (3×200 mL). Finally, the aqueous phase was extracted with dichloromethane (3×180 mL) collecting the organic layers to dry over Na$_2$SO$_4$. The solution was filtered and the solvent evaporated. The remaining mass was purified using Combiflash. The pure product 4 was collected as yellowish oil (9.8 g, yield 28% over three steps) and analyzed by $^1$H NMR. PEG$_{350}$-NH$_2$: $^1$H NMR (400 MHz, CDCl$_3$) δ 3.65-3.60 (m, 26H), 3.58-3.52 (m, 4H), 3.36 (s, 3H), 2.90 (t, J=5.1 Hz, 2H), 2.47 (s, NH$_2$).

Synthesis of 2-(2-Pyridyldithio)ethylamine Hydrochloride

Synthesis of PDS-NH$_2$

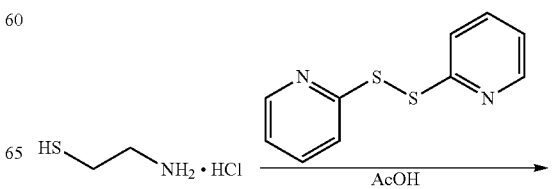

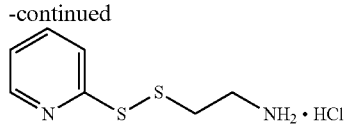

Pyridine disulfide (8.82 g, 0.040 mol) was dissolved in 100 mL of MeOH followed by the addition of 1 mL of glacial acetic acid. Then, the mixture was slowly added with 30 mL of 2-Mercaptoethylamine hydrochloride (2.28 g, 0.020 mol) solution in MeOH at 0° C. The reaction was kept for overnight. The reaction mixture was concentrated to afford yellow grease, which was dissolved in limited amount of MeOH and precipitated in cold ether. A colorless product was obtained after repeating the precipitation 4 times. Yield: 52%. $^1$H NMR (400 MHz, $D_2O$): 8.50-8.41 (m, 1H), 7.89-7.82 (m, 1H), 7.80-7.72 (m, 1H), 7.31-7.37 (m, 1H), 3.38-3.32 (t, 2H), 3.14-3.08 (t, 2H).

Synthesis of Pentafluorophenyl Acrylate PFPA

Synthesis of PFPA

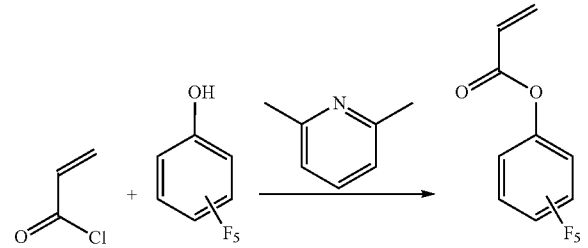

Monomer was synthesized by using a previously reported procedure. Briefly, pentafluorophenol (5.40 g, 29.3 mmol) and 2,6-lutidine (3.80 mL, 32.7 mmol) were dissolved in dry dichloromethane (50.0 mL). The above solution was cooled in an ice bath and then acryloyl chloride was added (2.65 mL, 32.7 mmol). After stirring at ambient temperature for 12 hours, the reaction mixture was washed with water. The organic layer was collected, and dried over anhydrous sodium sulfate. Crude product was further purified by flash chromatograph to afford pure product. Yield: 54%. 1H NMR (400 MHz, $CDCl_3$) δ: 6.74 (d, 1H), 6.36 (q, 1H), 6.19 (d, 1H). $^{19}$F NMR (300 MHz, $CDCl_3$) δ: −152.5 (2F, d), −157.9 (1F, t), −162.3 (2F, d).

Synthesis of Homopolymer PPFPA by RAFT

To a Schlenk-flask, pentafluorophenyl acrylate (1.0 g, 4.2 mmol), recrystallized azodiisobutyonitrile (AIBN) (3.44 mg, 0.021 mmol), and 2-(Dodecylthiocarbonothioylthio)-2-methylpropionic acid (15.32 mg, 0.042 mmol) were mixed in 1,4-dioxane (1 mL). The solution mixture was subjected to three freeze-pump-thaw cycles. The sealed flask was immersed in a preheated oil bath at 80° C. The polymerization reaction was allowed to proceed for 18 h. The polymerization was quenched by cooling down the flask in ice water. The reaction mixture was concentrated and then precipitated in methanol. Pure polymer was obtained after re-dissolve the precipitate in THF and precipitate in methanol for two more times. Yield 80%: $^1$H NMR (400 MHz, $CDCl_3$) δ: 3.25-1.85 (backbone). $^{19}$F NMR (300 MHz, $CDCl_3$) δ: −153.5 (2F), −157.0 (1F), −161.3 (2F). GPC (THF) Mn: 13.4 kDa. PDI: 1.26.

Synthesis of Homopolymer PPFPA by Conversional Radical Polymerization

Pentafluorophenyl acrylate (1.0 g, 4.2 mmol), recrystallized azodiisobutyonitrile (AIBN) (6.5 mg, 0.040 mmol) were dissolved in 5 mL dry benzene and placed in a Schlenk flask. Three freeze-pump-thaw cycles were applied before heating the reaction mixture in 80° C. Polymerization was stopped after 6 hours. The polymer was purified by precipitation in methanol for 3 times. Yield 85%: $^1$H NMR (400 MHz, $CDCl_3$) δ: 3.25-1.85 (backbone). $^{19}$F NMR (300 MHz, $CDCl_3$) δ: −153.0 (2F), −157.2 (1F), −161.1 (2F). GPC (THF) Mn: 60 kDa. PDI: 1.8.

Synthesis of Polymer 1

Synthesis of Polymer 1

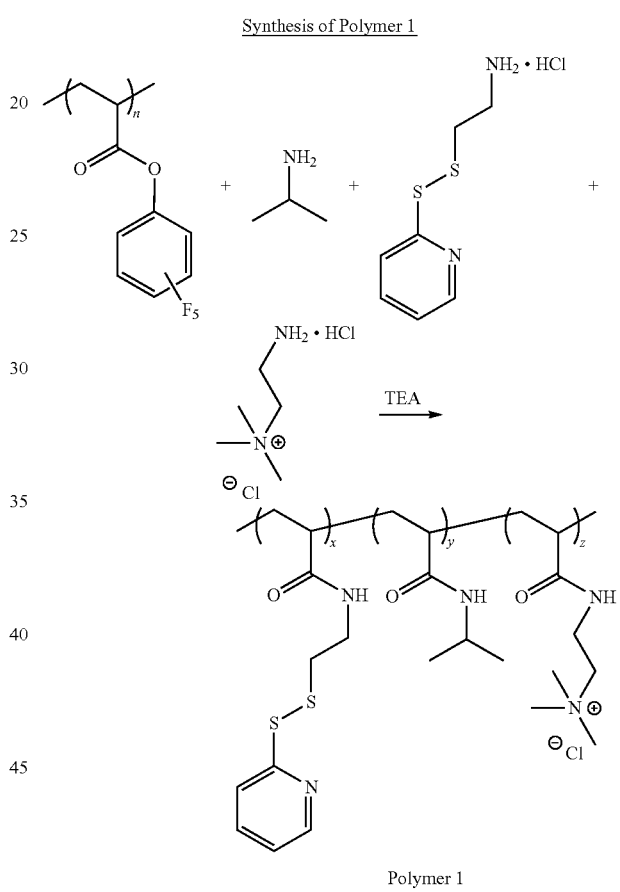

Polymer 1

PPFPA homopolymer (238 mg, 1 mmol repeat unit) was dissolved in 1 mL THF. Isopropyl amine (25.5 µL, 0.3 mmol), PDS amine (111.4 mg, 0.5 mmol), (2-aminoethyl)trimethylammonium chloride hydrochloride (35 mg, 0.2 mmol) and diisopropylethylamine (240 µL, 1.7 mmol) were dissolved in 1 mL MeOH. The mixed amine solution was added to polymer solution. The reaction was kept for 3 hours. Then, additional 0.2 equivalent of mixed amine was added to the reaction mixture to ensure the full substitution of PFP group. The reaction was monitored by FTIR. After the reaction complete, the polymer was purified by dialyze the mixture against DCM/MeOH mixture using dialysis membrane (MWCO: 3500 Da). Yield 85%. x/y/z=0.39/0.42/0.19 (calculated from $^1$HNMR)

Synthesis of Polymer 2

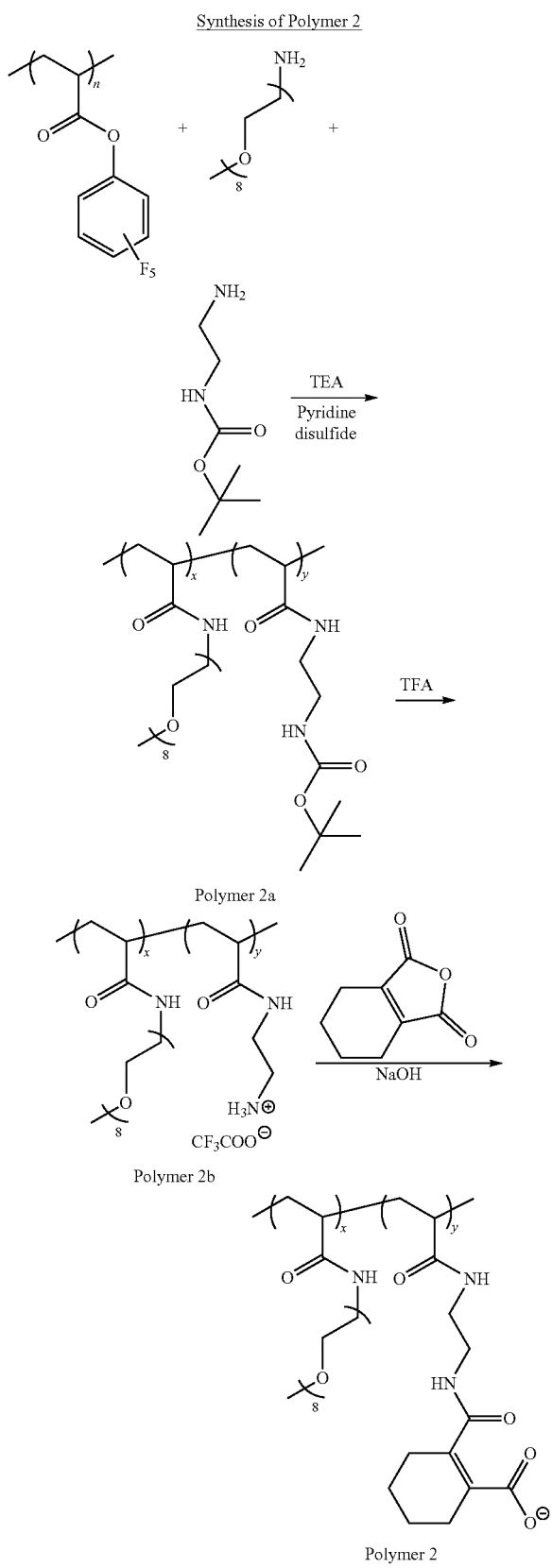

Synthesis of Polymer 2a

PPFPA homopolymer (400 mg, 1.68 mmol repeat unit) was dissolved in 2 mL THF. To the polymer solution, 2,2'-bipyridyldisulfide (37 mg, 0.168 mmol) was added. N-Boc-ethylenediamine (80.7 mg, 0.504 mmol) and PEG amine (449 mg, 1.176 mmol) and diisopropylethylamine (267 µL, 1.85 mmol) were dissolved in 1 mL THF. The mixed amine solution was added to polymer solution. After 3 hours, additional 0.2 equivalent of mixed amine was added to the reaction mixture to ensure the full substitution of PFP group. The completion of reaction was followed by FTIR. The polymer was purified by dialyzing the mixture against DCM/MeOH mixture using dialysis membrane (MWCO: 3500 Da). The polymer was afforded after concentrate and dry on vacuum. Yield 74%: x/y=0.66/0.34 (calculated from NMR).

Synthesis of Polymer 2b

To 1 mL DCM solution containing 300 mg of polymer 2a, 1 mL of TFA was added. The mixture was stirring overnight. The reaction mixture was concentrated before precipitation in cold ethyl ether. The precipitate was further rinsed with ethyl ether twice. The precipitate was vacuum dried to get pure polymer. Yield 90%.

Synthesis of Polymer 2

Triethylamine (900 µL, 6.435 mmol) was added to polymer 2b (150 mg, 0.429 mmol repeat unit) solution in 1 mL DMF followed by the addition of 3, 4, 5, 6-Tetrahydrophthalic anhydride (195.6 mg, 1.287 mmol). The reaction was kept overnight to be completed. The polymer was purified by dialysis against MeOH. Pure polymer 2 was obtained after concentrating and vacuum drying. Yield 90%

Nanogel Preparation and Nile Red Encapsulation

Polymer 1 was dissolved in water directly to make 10 mg/mL solution. 1 mL of polymer solution was placed in a glass vial. 1 wt % of Nile red solution (20 µL) in acetone was added to the vial, then 0.8 mg of DTT was added to polymer solution under stirring. The cross-linking reaction was allowed to proceed overnight. Then, the solution was dialyzed against water followed by filtrate through the syringe filter (0.4 µm). The final concentration of nanogel was fixed to 2.5 mg/mL by adding water.

Nanogel Covalently Labeled with Fluorescein

The prepared nanogel was added with calculated amount of thiol-functionalized fluorescein. The conjugation was evident by the release of pyridinethione by UV-vis spectroscopy. Then the unreacted dye was removed by dialysis.

Nanogel/Polyanion Complex Formation 400 uL of nanogel solution was diluted to make 1 mg/mL solution (pH 9) where desired volume of 10 mg/mL polyanion (pH 9) was added dropwise under stirring. The mixture was allowed to stir for 30 min. Excess polyanion was removed by ultrafiltration using membrane (MWCO. 100 kDa).

In this specification and the appended claims, the singular forms "a," "an," and "the" include plural reference, unless the context clearly dictates otherwise. Unless defined otherwise, all technical and scientific terms used herein have the same meaning as commonly understood too one of ordinary skill in the art. Unless defined otherwise, all technical and scientific terms used herein have the same meaning as commonly understood by one of ordinary skill in the art. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A method for modifying the release rate of an encapsulated guest in a polymer nanogel host, comprising preparing the polymer nanogel host in an aqueous environment having a kosmotropic or chaotropic agent, wherein the kosmotropic or chaotropic agent is present at a concentration suitable for achieving the desired guest release rate,
wherein the polymer nanogel host comprises a block co-polymer having the structural formula:

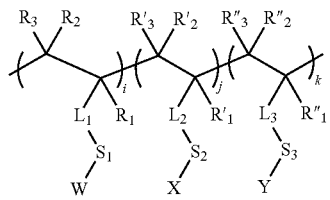

wherein
each of $R_1$, $R'_1$ and $R''_1$ is independently a hydrogen, $C_1$-$C_{12}$ alkyl group, or halogen;
each of $R_2$, $R'_2$, $R''_2$, $R_3$, $R'_3$ and $R''_3$ is independently a hydrogen, ($C_1$-$C_{16}$) alkyl, ($C_1$-$C_{16}$) alkyloxy, or halogen;
each of $L_1$, $L_2$ and $L_3$ is independently a linking group;
each of $S_1$, $S_2$ and $S_3$ is independently a single bond or a spacer group;
W is a hydrophilic group;
X is a group comprising a crosslinking moiety;
Y is a hydrophobic group; and
each of i, j and k is independently a positive number.

2. The method of claim 1, comprising preparing the polymer nanogel in an aqueous environment having a kosmotropic agent.

3. The method of claim 1, comprising preparing the polymer nanogel in an aqueous environment having a chaotropic agent.

4. The method of claim 2, wherein the kosmotropic agent is selected from the group consisting of sulfate ($SO_4^{2-}$), phosphate ($PO_4^{3-}$), hydrogenphosphates ($HPO_4^{2-}$), hydroxide ($OH^-$), magnesium ($Mg^{2+}$), calcium ($Ca^{2+}$), sodium ($Na^+$), lithium ($Li^+$), proton ($H^+$), trialkylamine oxide ($R_3N^+O^-$), proline, ectoine, glycine betaine, and trehalose.

5. The method of claim 4, wherein the kosmotropic agent is a sulfate ($SO_4^{2-}$).

6. The method of claim 3, wherein the chaotropic agent is selected from the group consisting of thiocyanates ($SCN^-$), dihydrogenphosphates ($H_2PO_4^-$), bisulfates ($HSO_4^-$), bicarbonates ($HCO_3^-$), iodides ($I^-$), bromides ($Br^-$), chlorides ($Cl^-$), nitrates ($NO_3^-$), ammonium ($NH_4^+$), cesium ($Cs^+$), potassium ($K^+$), guanidinium (($NH_2$)$_3C^+$), tetraalkylammonium ($R_4N^+$), and urea.

7. The method of claim 6, wherein the chaotropic agent is a thiocyanate ($SCN^-$).

8. The method of claim 2, wherein the kosmotropic agent is present at a concentration from about 1 mM to about 5 M.

9. The method of claim 3, wherein the chaotropic agent is present at a concentration from about 1 mM to about 5 M.

10. The method of claim 1, wherein the polymer nanogel comprises a crosslinked network of polymer molecules and non-covalently encapsulated therein a guest releasable upon partial or complete de-crosslinking of the crosslinked network of polymer molecules.

11. The method of claim 1, wherein each of $R_2$, $R'_2$, $R''_2$, $R_3$, $R'_3$ and $R''_3$ is a hydrogen, and each of $R_1$, $R'_1$ and $R''_1$ is a methyl group.

12. The method of claim 11, wherein each of $L_1$, $L_2$ and $L_3$ is

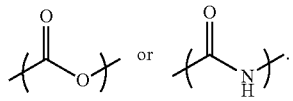

13. The method of claim 11, wherein W comprises a charged group and/or a zwitterionic group.

14. The method of claim 12, wherein W comprises

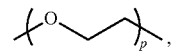

wherein p is an integer from about 1 to about 40.

15. The method of claim 12, wherein Y comprises a hydrocarbon chain.

16. The method of claim 15, wherein X comprises a disulfide moiety, an acetal moiety and/or an enzyme-sensitive linker.

17. The method of claim 16, wherein X comprises a disulfide moiety.

18. The method of claim 16, wherein X comprises an acetal moiety.

19. The method of claim 16, wherein X comprises an enzyme-sensitive linker.

* * * * *